(12) United States Patent
Hattersley

(10) Patent No.: US 12,263,141 B2
(45) Date of Patent: Apr. 1, 2025

(54) METHODS FOR TREATING CANCER

(71) Applicant: Radius Pharmaceuticals, Inc., Boston, MA (US)

(72) Inventor: Gary Hattersley, Stow, MA (US)

(73) Assignee: RADIUS PHARMACEUTICALS, INC., Boston, MA (US)

( * ) Notice: Subject to any disclaimer, the term of this patent is extended or adjusted under 35 U.S.C. 154(b) by 0 days.

(21) Appl. No.: 17/510,050

(22) Filed: Oct. 25, 2021

(65) Prior Publication Data

US 2022/0110890 A1   Apr. 14, 2022

Related U.S. Application Data

(63) Continuation of application No. 16/545,859, filed on Aug. 20, 2019, now abandoned, which is a continuation of application No. 15/794,910, filed on Oct. 26, 2017, now abandoned, which is a continuation of application No. PCT/US2016/030316, filed on Apr. 29, 2016.

(60) Provisional application No. 62/323,572, filed on Apr. 15, 2016, provisional application No. 62/323,576, filed on Apr. 15, 2016, provisional application No. 62/265,663, filed on Dec. 10, 2015, provisional application No. 62/265,658, filed on Dec. 10, 2015, provisional application No. 62/265,696, filed on Dec. 10, 2015, provisional application No. 62/265,774, filed on Dec. 10, 2015, provisional application No. 62/252,916, filed on Nov. 9, 2015, provisional application No. 62/252,085, filed on Nov. 6, 2015, provisional application No. 62/192,940, filed on Jul. 15, 2015, provisional application No. 62/192,944, filed on Jul. 15, 2015, provisional application No. 62/158,469, filed on May 7, 2015, provisional application No. 62/155,451, filed on Apr. 30, 2015, provisional application No. 62/154,699, filed on Apr. 29, 2015.

(51) Int. Cl.
| | | |
|---|---|---|
| *A61K 31/137* | (2006.01) | |
| *A61K 31/436* | (2006.01) | |
| *A61K 31/519* | (2006.01) | |
| *A61K 31/675* | (2006.01) | |
| *A61K 45/06* | (2006.01) | |
| *A61P 35/00* | (2006.01) | |
| *A61P 35/04* | (2006.01) | |

(52) U.S. Cl.
CPC .......... *A61K 31/137* (2013.01); *A61K 31/436* (2013.01); *A61K 31/519* (2013.01); *A61K 31/675* (2013.01); *A61K 45/06* (2013.01); *A61P 35/00* (2018.01); *A61P 35/04* (2018.01); *A61K 2300/00* (2013.01)

(58) Field of Classification Search
CPC .............. A61K 2300/00; A61K 31/137; A61K 31/436; A61K 31/519; A61K 31/675; A61K 45/06; A61K 31/138; A61P 35/00; A61P 35/04
See application file for complete search history.

(56) References Cited

U.S. PATENT DOCUMENTS

| | | |
|---|---|---|
| 5,589,452 A | 12/1996 | Krstenansky et al. |
| 5,691,312 A | 11/1997 | Paques |
| 5,693,616 A | 12/1997 | Krstenansky et al. |
| 5,695,955 A | 12/1997 | Krstenansky et al. |
| 5,723,577 A | 3/1998 | Dong |
| 5,798,225 A | 8/1998 | Krstenansky et al. |
| 5,807,823 A | 9/1998 | Krstenansky et al. |
| 5,821,225 A | 10/1998 | Vickery |
| 5,840,837 A | 11/1998 | Krstenansky et al. |
| 5,874,086 A | 2/1999 | Krstenansky et al. |
| 5,955,574 A | 9/1999 | Dong |
| 5,969,095 A | 10/1999 | Dong |
| 5,977,070 A | 11/1999 | Piazza et al. |
| 6,050,988 A | 4/2000 | Zuck |
| 6,051,686 A | 4/2000 | Krstenansky et al. |
| 6,083,196 A | 7/2000 | Trautman et al. |
| 6,091,975 A | 7/2000 | Daddona et al. |
| 6,120,761 A | 9/2000 | Yamazaki et al. |
| 6,136,784 A | 10/2000 | L'Italien et al. |
| 6,316,410 B1 | 11/2001 | Barbier et al. |

(Continued)

FOREIGN PATENT DOCUMENTS

| | | |
|---|---|---|
| CA | 2234724 | 10/1996 |
| CN | 104436194 A | 3/2007 |

(Continued)

OTHER PUBLICATIONS

Paplomata E, O'Regan R. New and emerging treatments for estrogen receptor-positive breast cancer: focus on everolimus. Therapeutics and clinical risk management. Jan. 14, 2013:27-36. (Year: 2013).*

(Continued)

*Primary Examiner* — Jeffrey S Lundgren
*Assistant Examiner* — Heather Dahlin
(74) *Attorney, Agent, or Firm* — Honigman LLP; Christopher C. Forbes

(57) ABSTRACT

Disclosed herein are methods of treating one or more tumors by administering to the subject a therapeutically effective amount of a combination of RAD1901 or solvates (e.g., hydrate) or salts thereof and one or more second therapeutic agent(s) (e.g., everolimus). The cancer is an estrogen-dependent cancer, such as breast cancer, ovarian cancer, colon cancer, endometrial cancer, or prostate cancer.

Figure 2A:
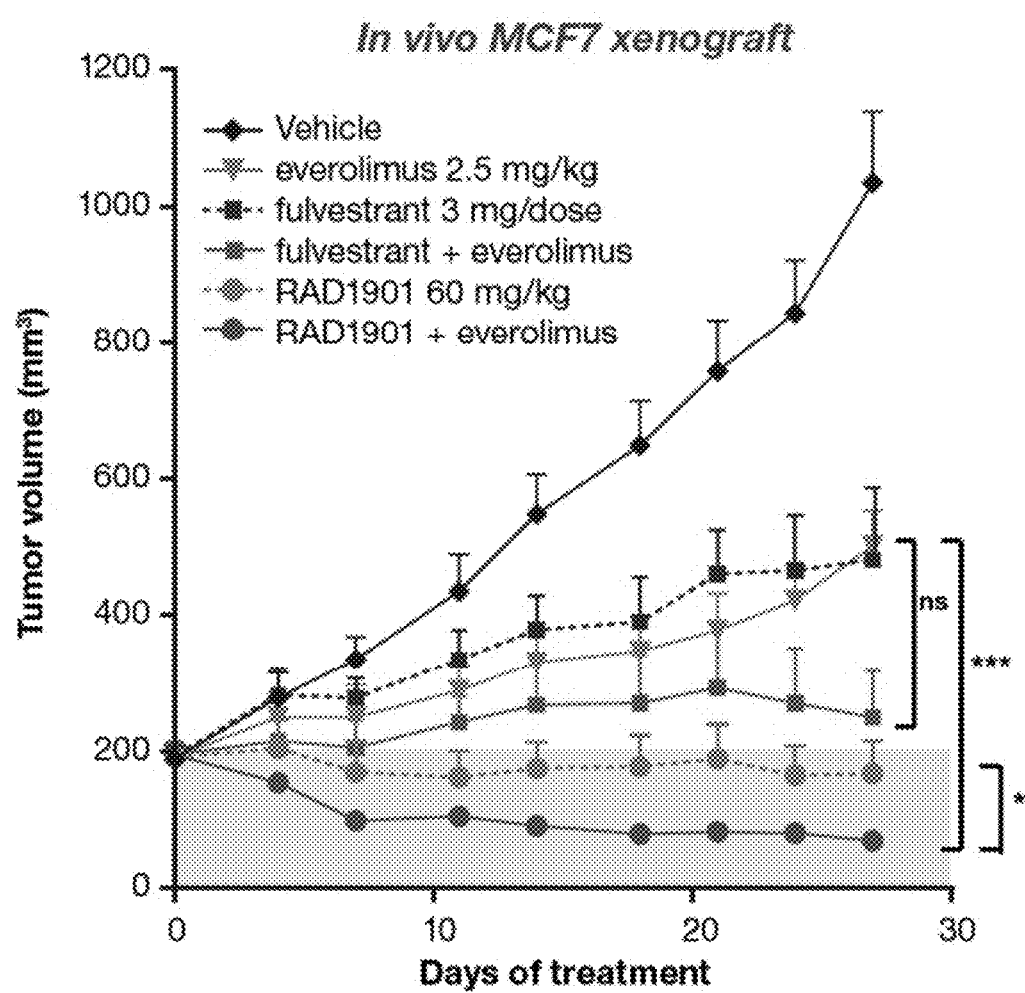

14 Claims, 57 Drawing Sheets
(55 of 57 Drawing Sheet(s) Filed in Color)

(56) References Cited

U.S. PATENT DOCUMENTS

| | | |
|---|---|---|
| 6,526,316 B2 | 2/2003 | Iga |
| 6,544,949 B1 | 4/2003 | Dong |
| 6,583,114 B2 | 6/2003 | Vickery |
| 6,740,522 B2 | 5/2004 | Anderson |
| 6,756,375 B2 | 6/2004 | Veeneman et al. |
| 6,756,480 B2 | 6/2004 | Kostenuik et al. |
| 6,770,623 B1 | 8/2004 | Chang et al. |
| 6,849,710 B1 | 2/2005 | Arzeno |
| 6,881,203 B2 | 4/2005 | Delmore et al. |
| 6,921,750 B2 | 7/2005 | Dong |
| 7,056,886 B2 | 6/2006 | Isaacs |
| 7,097,631 B2 | 8/2006 | Trautman et al. |
| 7,097,834 B1 | 8/2006 | Boyle |
| 7,141,544 B2 | 11/2006 | Somers et al. |
| 7,172,999 B2 | 2/2007 | Mattern et al. |
| 7,186,683 B2 | 3/2007 | Henriksen |
| 7,214,381 B2 | 5/2007 | Carrara |
| 7,244,709 B2 | 7/2007 | Quay et al. |
| 7,335,377 B2 | 2/2008 | Stern |
| 7,363,075 B2 | 4/2008 | Stern |
| 7,364,736 B2 | 4/2008 | Boyle et al. |
| 7,371,721 B2 | 5/2008 | Henriksen et al. |
| 7,383,084 B2 | 6/2008 | Stern |
| 7,410,948 B2 | 8/2008 | Dong |
| 7,411,050 B2 | 8/2008 | Anderson |
| 7,411,039 B2 | 10/2008 | Bhardwaj |
| 7,537,795 B2 | 5/2009 | Cormier |
| 7,556,821 B2 | 7/2009 | Ameri |
| 7,558,625 B2 | 7/2009 | Levin |
| 7,579,013 B2 | 8/2009 | Ameri |
| 7,612,114 B2 | 11/2009 | Hamaoka |
| 7,662,404 B2 | 2/2010 | Stern |
| 7,786,098 B2 | 8/2010 | Feng et al. |
| 7,799,757 B2 | 9/2010 | Chorev et al. |
| 7,803,770 B2 | 9/2010 | Dey |
| 7,846,488 B2 | 12/2010 | Johnson et al. |
| 7,906,137 B2 | 3/2011 | Byun et al. |
| 8,041,421 B2 | 10/2011 | Birchall |
| 8,133,505 B2 | 3/2012 | Stern |
| 8,148,333 B2 | 4/2012 | Dey |
| 8,329,649 B2 | 12/2012 | Asada et al. |
| 8,450,481 B2 | 5/2013 | Masliah et al. |
| 8,632,801 B2 | 1/2014 | Ameri et al. |
| 8,748,382 B2 | 6/2014 | Dey |
| 8,933,130 B2 | 1/2015 | Lytde |
| 8,980,272 B2 | 3/2015 | Nomiyama |
| 9,421,264 B2 | 8/2016 | Wardell et al. |
| 9,475,798 B2 | 10/2016 | Govek et al. |
| 9,549,746 B2 | 1/2017 | Woolfson et al. |
| 9,623,087 B2 | 4/2017 | Zhang et al. |
| 9,687,641 B2 | 6/2017 | Singh et al. |
| 9,693,950 B2 | 7/2017 | Determan et al. |
| 9,845,291 B2 | 12/2017 | Goodacre et al. |
| 10,010,706 B2 | 7/2018 | Gonzalez et al. |
| 10,238,848 B2 | 3/2019 | Singh et al. |
| 10,420,734 B2 * | 9/2019 | Wardell ............... A61K 31/137 |
| 11,819,480 B2 | 11/2023 | Garner et al. |
| 2002/0077281 A1 | 6/2002 | Vickery |
| 2002/0107505 A1 | 8/2002 | Holladay |
| 2002/0177839 A1 | 11/2002 | Cormier et al. |
| 2003/0039654 A1 | 2/2003 | Kostenuik et al. |
| 2003/0135150 A1 | 7/2003 | Kuribayashi |
| 2003/0181936 A1 | 9/2003 | Trautman et al. |
| 2004/0214996 A1 | 10/2004 | Kostenuik et al. |
| 2004/0265354 A1 | 12/2004 | Ameri et al. |
| 2004/0265365 A1 | 12/2004 | Daddona et al. |
| 2005/0009739 A1 | 1/2005 | Wang et al. |
| 2005/0032698 A1 | 2/2005 | Day et al. |
| 2005/0096586 A1 | 5/2005 | Trautman |
| 2005/0106209 A1 | 5/2005 | Ameri et al. |
| 2005/0106227 A1 | 5/2005 | Zalipsky et al. |
| 2005/0112135 A1 | 5/2005 | Cormier et al. |
| 2005/0124537 A1 | 6/2005 | Kostenuik et al. |
| 2005/0124625 A1 | 6/2005 | Salvati et al. |
| 2005/0209144 A1 | 9/2005 | Billger et al. |
| 2005/0222100 A1 | 10/2005 | Kloosterboer et al. |
| 2005/0250749 A1 | 11/2005 | Labrie |
| 2005/0261631 A1 | 11/2005 | Clarke et al. |
| 2005/0276823 A1 | 12/2005 | Cini et al. |
| 2005/0282749 A1 | 12/2005 | Henriksen et al. |
| 2006/0115472 A1 | 6/2006 | Li et al. |
| 2006/0116364 A1 | 6/2006 | Hamaoka et al. |
| 2006/0142387 A1 | 6/2006 | Cadilla et al. |
| 2006/0148893 A1 | 7/2006 | Blanc et al. |
| 2006/0188555 A1 | 8/2006 | Cormier et al. |
| 2006/0211608 A1 | 9/2006 | Holick |
| 2007/0021216 A1 | 1/2007 | Guruparan |
| 2007/0129409 A1 | 6/2007 | Hu et al. |
| 2007/0184096 A1 | 8/2007 | Ameri |
| 2007/0196395 A1 | 8/2007 | Mackerell et al. |
| 2007/0213543 A1 | 9/2007 | Rodriguez |
| 2007/0249520 A1 | 10/2007 | Gore et al. |
| 2007/0256736 A1 | 11/2007 | Tonkovich et al. |
| 2007/0287949 A1 | 12/2007 | Levin |
| 2007/0299009 A1 | 12/2007 | Dong |
| 2008/0027096 A1 | 1/2008 | Garg et al. |
| 2008/0039775 A1 | 2/2008 | Ameri et al. |
| 2008/0045504 A1 | 2/2008 | Gant et al. |
| 2008/0051699 A1 | 2/2008 | Choi et al. |
| 2008/0058383 A1 | 3/2008 | Jernstedt et al. |
| 2008/0119401 A1 | 5/2008 | Dong |
| 2008/0124402 A1 | 5/2008 | Kim et al. |
| 2008/0125399 A1 | 5/2008 | Wang et al. |
| 2008/0194536 A1 | 8/2008 | Hammond et al. |
| 2008/0269685 A1 | 10/2008 | Singh et al. |
| 2008/0318240 A1 | 12/2008 | Ejlersten et al. |
| 2009/0069226 A1 | 3/2009 | Ong et al. |
| 2009/0117158 A1 | 5/2009 | Ameri et al. |
| 2009/0170907 A1 | 7/2009 | Turnbull et al. |
| 2009/0198189 A1 | 8/2009 | Simons |
| 2009/0227498 A1 | 9/2009 | Dey et al. |
| 2009/0227571 A1 | 9/2009 | Loren et al. |
| 2009/0305965 A1 | 12/2009 | Kang et al. |
| 2010/0016223 A1 | 1/2010 | Gimona et al. |
| 2010/0030100 A1 | 2/2010 | Tokumoto et al. |
| 2010/0092566 A1 | 4/2010 | Alessi et al. |
| 2010/0119568 A1 | 5/2010 | Ameri |
| 2010/0151247 A1 | 6/2010 | Moore et al. |
| 2010/0152649 A1 | 6/2010 | Ameri |
| 2010/0160895 A1 | 6/2010 | Ameri |
| 2010/0203014 A1 | 8/2010 | Maggio |
| 2010/0221305 A1 | 9/2010 | Ameri |
| 2010/0226966 A1 | 9/2010 | Daddona |
| 2011/0006458 A1 | 1/2011 | Sagi et al. |
| 2011/0009387 A1 | 1/2011 | Basso-Porcaro |
| 2011/0046052 A1 | 2/2011 | Yang |
| 2011/0092425 A1 | 4/2011 | Dey |
| 2011/0124617 A1 | 5/2011 | Lyttle et al. |
| 2011/0172609 A1 | 7/2011 | Moga |
| 2011/0213335 A1 | 9/2011 | Burton et al. |
| 2011/0276028 A1 | 11/2011 | Singh et al. |
| 2011/0288485 A1 | 11/2011 | Tokumoto |
| 2012/0150023 A1 | 6/2012 | Kasper et al. |
| 2012/0219538 A1 | 8/2012 | Borchard et al. |
| 2013/0006217 A1 | 1/2013 | Hattersley |
| 2013/0085105 A1 | 4/2013 | Deasy |
| 2013/0123707 A1 | 5/2013 | Determan et al. |
| 2013/0157955 A1 | 6/2013 | Dey |
| 2014/0024582 A1 | 1/2014 | Yang |
| 2014/0046292 A1 | 2/2014 | Hattersley |
| 2014/0046293 A1 | 2/2014 | Hattersley |
| 2014/0228293 A1 | 8/2014 | Danishefsky et al. |
| 2014/0330198 A1 | 11/2014 | Zhang et al. |
| 2014/0343499 A1 | 11/2014 | Zhang |
| 2015/0211074 A1 | 7/2015 | Sowadski et al. |
| 2015/0231134 A1 | 8/2015 | Erichsen |
| 2015/0258080 A1 | 9/2015 | Hager et al. |
| 2015/0274640 A1 | 10/2015 | Wardell et al. |
| 2015/0320754 A1 | 11/2015 | Kutok et al. |
| 2016/0279142 A1 | 9/2016 | Friedman et al. |
| 2016/0324808 A1 | 11/2016 | Wardell et al. |
| 2018/0153828 A1 | 6/2018 | Garner et al. |

(56) References Cited

U.S. PATENT DOCUMENTS

| | | |
|---|---|---|
| 2018/0169101 A1 | 6/2018 | Hattersley |
| 2018/0214393 A1 | 8/2018 | Hattersley |
| 2021/0052705 A1 | 2/2021 | Hattersley et al. |

FOREIGN PATENT DOCUMENTS

| | | |
|---|---|---|
| CN | 1927815 A | 3/2015 |
| WO | 1996/035447 A1 | 11/1996 |
| WO | 2001/036039 A2 | 5/2001 |
| WO | WO2003063859 A1 | 8/2003 |
| WO | 2004/060386 A1 | 7/2004 |
| WO | WO2005000309 A2 | 1/2005 |
| WO | WO2007034846 A1 | 3/2007 |
| WO | WO2008008433 A2 | 1/2008 |
| WO | WO2008024456 A2 | 2/2008 |
| WO | WO2008044033 A1 | 4/2008 |
| WO | WO2008121602 A1 | 10/2008 |
| WO | WO2008124000 A2 | 10/2008 |
| WO | WO2008127717 A1 | 10/2008 |
| WO | WO 2008145125 A1 | 12/2008 |
| WO | 2009/053106 A1 | 4/2009 |
| WO | WO2009133861 A1 | 11/2009 |
| WO | 2010/022176 A1 | 2/2010 |
| WO | WO2010118287 A1 | 10/2010 |
| WO | 2012/075375 A1 | 6/2012 |
| WO | 2014/203129 A1 | 12/2014 |

OTHER PUBLICATIONS

Alluri PG, Speers C, Chinnaiyan AM. Estrogen receptor mutations and their role in breast cancer progression. Breast Cancer Research. Dec. 2014;16:1-8. (Year: 2014).*

Alluri, P.G., et al, Estrogen Receptor Mutations and Their Role in Breast Cancer Progression, Breast Cancer Research, 2014, 16:494.

Ameri, M., et al., (2010) "Parathyroid Hormone PTH(1-34) Formulation that Enables Uniform Coating on a Novel Transdermal Microprojection Delivery System," Pharmaceutical Res, 27(2):303-313; Feb. 2010 (published online Dec. 15, 2009).

Ameri, M., et al., "Demonstrated Solid-State Stability of Parathyroid Hormone PTH(1-34) Coated on a Novel Transdermal Microprojection Delivery System," Pharmaceutical Res, 26(11):2454-2463; Nov. 2009; (published online Sep. 3, 2009).

Amugongo, S. K., et al., (2014) "Effect of Sequential Treatments with Alendronate, Parathyroid Hormone (1-34) and Raloxifene on Cortical Bone Mass and Strength in Ovariectomized Rats," Bone 67:257-268.

Anonymous: Radius Announced today that it has Acquired The License to Develop and Market RAD1901 in Japan, MPM Globe Newswire, Mar. 10, 2015, pp. 1-5, XP055683544; retrieved from: url:https://www.mpmcaptial.com/press/radius-rdus-anounced-today-acquired-license-develop-market-rad1901-japan/; retrieved Apr. 7, 2020.

Augustine, M. et al., (2013) "Parathyroid Hormone and Parathyroid Hormone-related Protein Analogs as Therapies for Osteoporosis," Curr. Osteoporos. Rep. 11(4):400-406.

Australian Patent Office, Examination Report for SG20090240-1 and dated Nov. 18, 2010.

Australian Patent Office, International Search Report and Written Opinion for SG20090240-1 completed Apr. 1, 2010 and dated Apr. 20, 2010.

Bachelot, Thomas, et al. Randomized Phase II Trial of Everolimus in Combination with Tamoxifen in Patients with Hormone Receptor-positive, Human Epidermal Growth Factor receptor 2-Negative Metastatic Breast Cancer with Prior Exposure to Aromatase Inhibitors: A Gineco Study, J of Clinical Oncology, Vo.. 30, No. 22, pp. 2718-2724, publ date Aug. 1, 2012.

Baselga (Everolimus in Postmenopausal Hormone-Receptor—Positive Advanced Breast Cancer, N Engl J Med. Feb. 9, 2012; 366(6): 520-529 (renumbered pp. 1-16)).

Belikov, V.G., Pharmaceutical Chemistry, Moscow, High School, 1993, vol. 1, pp. 43-47; 1993.

Bellido, T. et al., (1999) "Estrogen Inhibit Apoptosis of Osteoblasts and Osteocytes through Rapid (Non-genomic) Activation of Extracellular Signal-Regulated Kinases (ERKs)," J Bone Mineral Res, 14(Supp 1)(Abstract SA135):S342.

Berge et al., "Pharmaceutical Salts," Journal of Pharmaceutical Sciences, 1977, 66(1):1-19.

Bodenner, D.L. et al., (1999) "Essential Requirement of the Estrogen Receptor α or β for (Non-Genomic) Anti-Apoptotic Effects of Estrogen," J Bone and Mineral Res, 14(Supp 1)(Abstract F071):S227.

Bonnick, S. L., et al., (2001) "Importance of Precision in Bone Density Measurements," J. Clin. Densitometry 4(2):105-110.

Bonnick, S., et al., (2006) "Comparison of Weekly Treatment of Postmenopausal Osteoporosis with Alendronate Versus Risedronate Over Two Years," J. Clin. Endocrinol. Metab. 91(7):2631-2637.

Bostrom, M.P.G. et al., (2000) "Parathyroid Hormone-Related Protein Analog RS-66271 is an Effective Therapy for Impaired Bone Healing in Rabbits on Corticosteroid Therapy," Bone, 26(5):437-442.

Burr, D. B., et al., (2001) "Intermittently Administered Human Parathyroid Hormone(1-34) Treatment Increases Intracortical Bone Turnover and Porosity Without Reducing Bone Strength in the Humerus of Ovariectomized Cynomolgus Monkeys," J. Bone Min. Res. 16(1):157-165.

Chang, Minsun, (Tamoxifen Resistance in Breast Cancer, Biomolecues & Therapeutics 20(3), Apr. 2012, pp. 256-267).

Chantasingh, D., et al., (2006) "Cloning, Expression, and Characterization of a Xylanase 10 from Aspergillus Terreus (BCC129) in Pichia Pastoris," Protein Expre Purif, 46(1): 143-149 (Abstract Only).

Chinese Patent Office, Chinese Patent Search Report for 201110220104.X dated Feb. 26, 2013.

Chinese Patent Office, Chinese Patent Search Report for 201280030749X dated Feb. 16, 2015.

Chou, T.C., et al., (1984) "Quantitative Analysis of Dose-Effect Relationships: The Combined Effects of Multiple Drugs or Enzyme Inhibitors," Adv. Enzyme Regul. 22:27-55.

Clinical trials.gov, "A Study for the Transdermal Application of Teriparatide," Retrieved from: http://www.clinicaltrials.gov/ct2/show/NCT01011556?term=pth+patch&rank=8, Date Retrieved: Sep. 18, 2012, 6 pages.

Clinical trials.gov, "Dose Ranging Study—Macroflux PTH in Postmenopausal Women With Osteoporosis," Retrieved from: http://www.clinicaltrials.gov/ct2/show/NCT00489918?term=pth+patch&rank=1, Date Retrieved: Sep. 18, 2012, 1 page.

Collier, Mary E.W. et al., Influence of Exogenous tissue Factor on Estrogen Receptor α Expression in Breast Cancer Cells: Involvement of β1-Ingerin, PAR2, and Mitogen-Activated Protein Kinase Activation, Mol Cancer Res, 2008, vol. 6, No. 12, p. 1807-1818.

Cosman, F., (2008) "Parathyroid Hormone Treatment for Osteoporosis," Curr. Opin. Endocrinol. Diabetes Obes. 15:495-501.

Cosman, F., et al., (2009) "Effect of Transdermal Teriparatide Administration on Bone Mineral Density in Postmenopausal Women," J Clin Endocrinol Metab, 95(1):151-158 (published online Oct. 26, 2009).

Culler, M.D. et al., (2001) "BIM-44058, a Novel Analog of PTHrP with Enhanced Bone Building Activity, but Decreased Calcium-Mobilization Potential," Twenty-Third Annual Meeting of the American Society of Bone and Mineral Research, Phoenix, Arizona, USA, Oct. 12-16, 2001, J Bone Miner Res, (Abstract M460), 16(Suppl. 1):S540.

Culler, M.D. et al., (2002) "A Novel PTHRP Analog with Decreased Calcium-Mobilization Potential, but with Enhanced Bone Building Activity," S19, Abstract for the World Congress on Osteoporosis meeting held on May 10-14, 2002, Lisbon, Portugal (Abstract P51SU), Osteoporos Int 13(1) (Apr. 2002).

Daddona, Peter E., et al., (2011) "Parathyroid Hormone (1-34)-Coated Microneedle Patch System: Clinical Pharmacokinetics and Pharmacodynamics for Treatment of Osteoporosis," Pharm Res, 28:159-165 (published online Jun. 22, 2010).

Dean, T., et al., (2006) "Mechanisms of Ligand Binding to the Parathyroid Hormone (PTH)/PTH-Related Protein Receptor: Selec-

(56) References Cited

OTHER PUBLICATIONS tivity of a Modified PTH(1-15) Radioligand for Gas-Coupled Receptor Conformations," Mol. Endocrinol. 20(4):931-943.
Dean, T., et al., (2008) "Altered Selectivity of Parathyroid Hormone (PTH) and PTH-Related Protein (PTHrP) for Distinct Conformations of the PTH/PTHrP Receptor", Molecular Endocrinology, 22(1):156-166.
Dempster, D.W. et al., (1993) "Anabolic Actions of Parathyroid Hormone on Bone," Endocr Rev, 14(6):690-709.
Dempster, D.W. et al., (2001) "Effects of Daily Treatment with Parathyroid Hormone on Bone Microarchitecture and Turnover in Patients with Osteoporosis: A Paired Biopsy Study," J Bone Miner Res, 16:1846-1853.
Dempster, D. W., et al., (2012) "Skeletal Histomorphometry in Subjects on Teriparatide or Zoledronic Acid Therapy (SHOTZ) Study: A Randomized Controlled Trial," J. Clin. Endocrinol. Metab. 97(8):2799-2808.
Deschamps, P., et al., (2005) "The Saga of Copper(II)-L-histidine," Coordination Chem Reviews, 249:895-909.
Dhainaut, A., et al., (2013) "Cortical Hand Bone Porosity and its Association with Distal Radius Fracture in Middle Aged and Elderly Women," PLoS One 8(7):e68405.
Dong, J.Z. et al., (1998) "Development of Highly Potent Human Parathyroid Hormone Analogs," Peptides: Biology and Chemistry, Proceedings of the Chinese Peptide Symposium, 4th, Chengdu, Peop. Rep. China, Jul. 21-25, 1996, pp. 173-175.
Dong, J.Z. et al., (1999) "Highly Potent Human Parathyroid Hormone Analogs," Peptides: Frontiers of Peptide Science, Proceedings of the American Peptide Symposium, 15th, Nashville, Jun. 14-19, 1997, pp. 541-542.
Dong, J.Z. et al., (2001) "Highly Potent Analogs of Human Parathyroid Hormone and Human Parathyroid Hormone-Related Protein," Peptides: The Wave of the Future, Proceedings of the Second International and the Seventeenth American Peptide Symposium, San Diego, CA USA, Jun. 9-14, 2001, pp. 668-669.
Doyle, N., et al., (2013) "Long Term Effect of BA058, a Novel Human PTHrP Analog, Restores Bone Mass in the Aged Osteopenic Ovariectomized Cynomolgus Monkey," J. Bone Miner. Res. 28(Suppl 1): Abstract.
Doyle, N., et al., (2013) "BA058, A Novel Human PTHrP Analog: Reverses Overiectomy-Induced Bone Lloss and Strength at the Lumbar Spine in Aged Cynomolgus Monkeys," J. Bone Miner. Res. 28(Suppl 1) Abstract.
Ellard SL, Clemons M, Gelmon KA, et al. Randomized phase II study comparing two schedules of everolimus in patients with recurrent/metastatic breast cancer: NCIC Clinical Trials Group IND. 163. *J Clin Oncol.* 2009;27:4536-4541.
European Patent Office, International Search Report and Written Opinion completed Sep. 17, 2008 and dated Jun. 4, 2009 for PCT/US2007/021216.
European Patent Office, International Search Report and Written Opinion completed Jul. 27, 2009 and dated Aug. 3, 2009 for PCT/US2009/002868.
European Patent Office, International Search Report and Written Opinion completed Aug. 14, 2009 and dated Sep. 10, 2010 for PCT/US2009/002885.
European Patent Office, International Search Report and Written Opinion completed Dec. 19, 2011 and dated Jan. 16, 2012 for PCT/US2011/053375.
European Patent Office, International Search Report for EP15176548 completed Sep. 30, 2015 and dated Oct. 7, 2015.
European Pharmacopoeia 5.0 (EP), Chapter 5.1.3 "Efficacy of Antimicrobial Preservation," 447-4493; 2005.
Everhart-Caye, M. et al., (1996) "Parathyroid Hormone (PTH)-Related Protein(1-36) is Equipotent to PTH(1-34) in Humans," J Clin Endocrinol Metab, 81(1):199-208.
Fanning et al., "Estrogen receptor alpha somatic mutations Y537S and D538G confer breast cancer endocrine resistance by stabilizing the activating function-2 binding conformation," eLife, Feb. 2, 2016, vol. 5; 5:e12792.

FDA Guidance for Industry (2003) "Q1A(R2) Stability Testing of New Drug Substances and Products."
FDA, Full Prescribing Information for FORTEO (teriparatide) injection (2002).
Ferrandon, S., et al., "Sustained cyclic AMP production by parathyroid hormone receptor endocytosis", Nature Chemical Biology, 5(10):734-742 (Oct. 2009).
Finn, Richard S., et al., The cyclin-dependent kinase 4/6 inhibitor palbociclib in combination with letrozole versus letrozole alone as first-line treatment of oestrogen receptor-positive, HER2-negative, advanced breast cancer (PALOMA-1/TRIO-18): a randomised phase 2 study, The Lancet, Oncology, England, vol. 16, Jan. 2015; doi: 10.1016/S1470-2045(14)71159-3 (Jan. 1, 2015), pp. 25-35; URL: http://www.thelancet.com/pdfs/journals/lanonc/PIIS1470-2045(14)71159-3pdf, XP055375445 [Y] 14,15, the whole document DOI: http://dx.doi.org/10.1016/S1470-2045(4)71159-3.
Fox, J., (2002) "Developments in Parathyroid Hormone and Related Peptides as Bone-Formation Agents," Curr Opin Pharmacology, 2:338-344.
Fraher, L.J. et al., (1992) "A Comparison of the in Vivo Biochemical Responses to Exogenous Parathyroid Hormone-(1-34) [PTH-(1-34)] and PTH-Related Peptide-(1-34) in Man," J Clin Endocrinol Metab, 75(2):417-423.
Fraher, L.J. et al., (1995) "Comparison of the Pharmacokinetics of Parenteral Parathyroid Hormone-(1-34) [PTH-(1-34)] and PTH-Related Peptide-(1-34) in Healthy Young Humans," J Clin Endocrinol Metab, 80(1):60-64 (1995).
Frolik, C.A. et al., (1999) "Comparison of Recombinant Human PTH(1-34) (LY333334) with a C-Terminally Substituted Analog of Human PTH-Related Protein (1-34) (RS-66271): In Vitro Activity and In Vivo Pharmacological Effects in Rats," J Bone Miner Res, 14(2):163-172.
Frolik, C.A. et al., (2000) "Reply: Further Data are Required to Assure that the Discrepant Binding Affinity is Explained by Different Receptor Conformations," J Bone Miner Res, 15(3):608.
Gallagher, J.C. et al., (1999) "PTHrP(1-34) Analog, Semparatide Acetate (RS-66271), Causes Sustained Increases in Spine in Postmanopausal Osteoporotic Women: Two Randomized Placebo-Controlled Trials," J Bone Mineral Res, 14(Supp 1)(Abstract 1018):S137.
Gallagher, J.C., et al., (2006) "Response Rate of Bone Mineral Density to Teriparatide in Postmenopausal Women with Osteoporosis," Bone 39:1268-1275.
Garland, M.J., et al., (2011) "Microneedle arrays as medical devices for enhanced transdermal drug delivery," Expert Rev Med Devices, 8(4):459-482.
Garner et al., "RAD1901: a novel, orally bioavailable selective estrogen receptor degrader that demonstrates antitumor activity in breast cancer xenograft models," Anti-Cancer Drugs, vol. 26, No. 9, Oct. 31, 2015, 9 pages.
Giessrigl et al., "Fulvestrant induces resistance by modulating GPER and CDK6 expression: Implication of methyltransferases, deacetylases and the hSWVSNF chromatin remodelling complex," British Journal of Cancer, 2013, 109:2751-2762.
Gill, H.S. and Prausnitz, M.R., (2007) "Coating Formulations for Microneedles," Pharmaceutical Res, 24(7):1369-1380.
Han, S.L., et al., (2012) "Effect of Teriparatide on Bone Mineral Density and Fracture in Postmenopausal Osteoporosis: Meta-Analysis of Randomized Controlled Trials," Int. J. Clin. Pract. 66(2): 199-209.
Hansen, S., et al., (2013) "Differing Effects of PTH 1-34, PTH 1-84, and Zoledronic Acid on Bone Microarchitecture and Estimated Strength in Postmenopausal Women with Osteoporosis: An 18-Month Open-Labeled Observational Study Using HR-pQCT," J. Bone Min. Res. 28(4):736-745.
Hattersley, G., et al., (2013), "SUN-200: BA058, A Novel Human PTHrP Analog, Restores Bone Density and Increases Bone Strength at the Spine and Femur in Osteopenic Rats," Endocr. Soc. 95th Annual Meeting and Expo, San Francisco, CA, Jun. 15-18, 2013.
Hattersley, G., et al. "OR31-5: Differential Binding Selectivity of Abaloparatide (BA058) Compared to PTH and PTHrP for PTH Type 1 Receptor Conformations," Endocrine Society's 96th Annual Meeting and Expo, Jun. 21-24, 2014, Chicago, IL.

(56) References Cited

OTHER PUBLICATIONS

Henry, J.G. et al., (1997) "Parathyroid Hormone-Related Protein-(1-36) is Biologically Active When Administered Subcutaneously to Humans," J Clin Endocrinol Metab, 82(3):900-906.

Hildebrand, T. et al., (1999) "Direct Three-Dimensional Morphometric Analysis of Human Cancellous Bone: Microstructural Data from Spine, Femur, Iliac Crest, and Calcaneus," J Bone Miner Res, 14(7): 1167-1174.

Hoare, S.R.J. and Usdin, T.B., (1999) "Quantitative Cell Membrane-Based Radioligand Binding Assays for Parathyroid Hormone Receptors," J Pharmacol Toxicol, 41:83-90.

Hoare, S.R.J. and Usdin, T.B., (2000) "Letter to the Editor: The Discrepancy Between the Binding Affinity of PTH (1-34) and RS 66271 is Explained by Interaction of the PTH/PTHrP Receptor with G-Protein," J Bone Miner Res, 15(3):605-607.

Hochberg, M. C., et al., (1999) "Larger Increases in Bone Mineral Density During Allendronate Therapy are Associated with a Lower Risk of New Vertebral Fractures in Women with Postmenopausal Osteoporosis," Arthritis & Rheumatism, 42(6):1246-1254.

Holford, N. H., et al., (1981) "Understanding the Dose-Effect Relationship: Clinical Application of Pharmacokinetic-Pharmacodynamic Models," Clin. Parmacokinet. 6:429-453.

Horwitz, M.J. et al., (2003) "Direct Comparison of Sustained Infusion of Human Parathyroid Hormone-Related Protein-(1-36) [hPTHrP-(1-36)] Versus hPTH-(1-34) on Serum Calcium, Plasma 1,25-Dihydroxyvitamin D Concentrations, and Fractional Calcium Excretion in Healthy Human Volunteers," J Clin Endocrinol Metab, 88(4):1603-1609.

Horwitz, M.J. et al., (2003) "Short-Term, High-Dose Parathyroid Hormone-Related Protein as a Skeletal Anabolic Agent for the Treatment of Postmenopausal Osteoporosis," J Clin Endocrinol Metab, 88(2):569-575.

Horwitz, M.J. et al., (2005) "Continuous PTH and PTHrP Infusion Causes Suppression of Bone Formation and Discordant Effects on 1,25(OH)2 Vitamin D," J Bone Miner Res, 20(10):1792-1803.

Horwitz, M.J. et al., (2006) "Safety and Tolerability of Subcutaneous PTHrP(1-36) in Healthy Human Volunteers: a Dose Escalation Study," Osteoporos Int, 17:225-230.

Horwitz, M. J., et al., (2010) "Parathyroid Hormone-Related Protein for the Treatment of Postmenopausal Osteoporosis: Defining the Maximal Tolerable Dose," J. Clin. Endocrinol. Metab. 95:1279-1287.

Horwitz, M. J., et al., (2013) "A Comparison of Parathyroid Hormone-Related Protein (1-36) and Parathyroid Hormone (1-34) on Markers of Bone Turnover and Bone Density in Postmenopausal Women: The PrOP Study," J. Bone Min. Res. 28(11):2266-2276.

International Union of Pure and Applied Chemistry (1984) "Nomenclature and Symbolism for Amino Acids and Peptides," Pure Appl Chem 56:595-624.

Jeselsohn, R., et al., (2015) "ESR1 Mutations as a Mechanism for Acquired Endocrine Resistance in Breast Cancer," Nat. Rev. Clin. Oncol. 12:573-583.

Jorgensen, L., et al., (2009) "Recent trends in stabilising peptides and proteins in pharmaceutical formulation—consideration in the choice of excipients," Expert Opin Drug Delivery, 6(11):1219-1230.

Kalluri, H. and Banga, A. K., "Transdermal Delivery of Proteins," AAPS PharmSciTech, 12(1) 431-441 (published online Mar. 3, 2011).

Kamberi, M., (2005) The effects of sucrose on stability of human brain natriuretic peptide [hBNP(1-32)] and human parathyroid hormone (hPTH(1-34)], J Peptide Res, 66:348-356.

Katikaneni, S., et al., (2010) "Transdermal delivery of ~13 kDa protein—an in vivo comparison of physical enhancement methods", J Drug Targeting, 18(2):141-147.

Keaveny, T.M., et al., (2012) "Femoral Strength in Osteoporotic women Treated With Teriparatide or Alendronate," Bone 50:165-170.

Kenan, Y., et al., "Comparison of Transdermal and Subcutaneous Teriparatide Pharmacokinetics and Pharmacodynamics of Bone Markers in Postmenopausal Women," Poster Session, Presentation No. FR0376 of the ASBMR 2010 Annual Meeting, (Oct. 15-16, 2010).

Kharkevich, D.A., Pharmacotherapeutic effect as a function of properties . . . ; Pharmacology, Tenth Edition, 2008, pp. 66-67 and English Translation.

Kharkevich, D.A., Pharmacology: Textbook 2010, 10th Edition, pp. 72-82.

Kronenberg, H. M., (2006) "PTHrP and Skeletal Development," Ann. N.Y. Acad. Sci. 1068:1-13.

Krstenansky, J.L. et al., (1995) "RS-66271: Molecular Design and in vivo Bone Anabolic Activity," Peptides 1994, Proceedings of the European Peptide Symposium, 23rd, Braga, Port., Sept. 4-10, 1994:133-134.

Lamb, R., et al., (2013) "Cell Cycle Regulators Cyclin D1 and CDk4/6 Have Estrogen Receptor-Dependent Divergent Functions in Breast Cancer Migration and Stem Cell-Like Activity," Cell Cycle 12(15):2384-2394.

Lange, U., et al., "(2005) Increase in Bone Mineral Density of Patients with Rheumatoid Arthritis Treated with Anti-TNF-Alpha Antibody: A Prospective Open-Label Pilot Study," Rheumatol. 44:1546-1548.

Lanter, J.C., et al., (2007) "The Discovery of a Potent Orally Efficacious Indole Androgen Receptor Antagonist Through in vivo Screening," Bioorganic & Medicinal Chem Letters, 17:123-126.

Lazaridis (Strahlentherapie and Onkologie 7 • 2014, pp. 636-645).

Leder, B. Z., et al., (2013) "Two Years of Denosumab and Teriparatide Administration n Postmenopausal Women with Osteoporosis (The Data Extension Study): A Randomized Controlled Trial," Lancet 382(9886):50-56.

Legrand, J.J. et al., (2001) "BIM-44058, a Novel PTHrP Analog, Does Not Increase Total Plasma Calcium in Cynomolgus Monkeys at an Effective Pharmacological Dose," Twenty-Third Annual Meeting of the American Society of Bone and Mineral Research, Phoenix, Arizona, USA, Oct. 12-16, 2001, J Bone Miner Res, (Abstract M454) 16 (Suppl. 1):S539.

Legrand, J.J. et al., (2001) "BIM-44058, a Novel PTHrP Analog, Increases Bone Formation But Not Bone Resorption Histomorphometric Parameters in Old Ovariectomized Osteopenic Cynomolgus Monkeys," Twenty-Third Annual Meeting of the American Society of Bone and Mineral Research, Phoenix, Arizona, USA, Oct. 12-16, 2001, J Bone Miner Res, (Abstract M455) 16 (Suppl. 1):S539.

Legrand, J.J. et al., (2001) "BIM-44058, a Novel PTHrP Analog, Restores in Vivo Spinal Bone Mineral Density in Old Ovariectomized Osteopenic Cynomolgus Monkeys," Twenty-Third Annual Meeting of the American Society of Bone and Mineral Research, Phoenix, Arizona, USA, Oct. 12-16, 2001, J Bone Miner Res, (Abstract M453) 16 (Suppl. 1):S539.

Legrand, J.J. et al., (2002) "BIM-44058, A Novel PTHrP Analog, Restores BMD by Selectively Increasing Bone Formation in Old Ovariectomized, Osteopenic Cynomolgus Monkeys," S20, Abstract for the World Congress on Osteoporosis meeting held on May 10-14, 2002, Lisbon, Portugal (Abstract P53SA), Osteoporos Int 13(1).

Legrand, J.J., et al., (2003) "Use of Biochemical Markers to Monitor Changes in Bone Turnover in Cynomolgus Monkeys," Biomarkers, 8(1):63-77.

Li, Ying, et al., Advances in treatment of breast cancer with combined endocrine therapy and novel target agents, Academic Journal of Chinese PLA Medical School, 2013, Vo.. 34, No. 10, pp. 1092-1094, publ date Apr. 9, 2013.

Lloyd, M.E., et al., (1996) "Relation Between Insulin-Like Growth Factor-I Concentrations, Osteoarthritis, Bone Density, and Fractures in the General Population: the Chingford Study," Ann Rheum Dis, 55:870-874.

Ma, Y. L., et al., (2011) "Comparative Effects of Teriparatide and Strontium Ranelate in the Periosteum of Iliac Crest Biopsies in Postmenopausal Women with Osteoporosis," Bone 48:972-978.

Ma, Y.L., et al., (2014) Effects of Teriparatide on Cortical Histomorphometric Variables in Postmenopausal Women With or Without Prior Alendronate Treatment. Bone 59:139-147.

(56) References Cited

OTHER PUBLICATIONS

MacLean, C., et al., (2008) "Systematic Review: Comparative Effectiveness of Treatments to Prevent Fractures n Men and Women with Low Bone Density or Osteoporosis," Ann. Intern. Med. 148:197-213.
Mannstadt, M. et al., (1999) "Receptors for PTH and PTHrP: Their Biological Importance and Functional Properties," American Physiological Society: Invited Review:F665-F675.
Manolagas, S.C. et al., (1999) "Opposite Effects of Estrogen on the Life Span of Osteoblasts/Osteocytes Versus Osteoclasts In Vitro: An Explanation of the Imbalance between Formation and Resorption in Estrogen Deficiency," J Bone Mineral Res, 14(Supp 1)(Abstract 1147):S169.
Manolagas, S.C., (1999) "Activators of Non-Genomic Estrogen-Like Signalling (ANGELS): a Novel Class of Small Molecules with Bone Anabolic Properties," J Bone Mineral Res, 14(Supp 1)(Abstract 1191):S180.
Marino, M. et al., "Estrogen Signaling Multiple Pathways to Impact Gene Transcription," Current Genomics, 2006, 7, 497-508.
Martin, T.J., (2005) "Osteoblast-derived PTHrP is a Physiological Regulator of Bone Formation," J Clin Invest, 115(9):2322-2324.
Medi, B.M. and Singh, J., (2003) "Electronically Facilitated Transdermal Delivery of Human Parathyroid Hormone (1-34)," International J Pharmaceutics, 263:25-33.
Merenbakh-Lamin et al., "D538 G Mutation in Estrogen Receptor-a: A Novel Mechanism for Acquired Endocrine Resistance in Breast Cancer," Cancer Res, 2013, 73(23):6856-6864.
Mesu, J. G., et al., (2005) "Infrared and Raman Spectroscopic Study of pH-induced Structural Changes of L-histidine in Aqueous Environment," Vibrational Spectroscopy, 39:114-125.
Miao, D., et al., (2004) "Skeletal Abnormalities in Pth-Null Mice are Influenced by Dietary Calcium," Endocrinology 145:2046-2053.
Miao, D., et al., (2005) "Osteoblast-derived PTHrP is a Potent Endogenous Bone Anabolic Agent that Modifies the Therapeutic Efficacy of Administered PTH 1-34," J Clin Invest, 115(9):2402-2411.
Miller, P. D., et al., (2005) "Monthyl Oral Ibandronate Therapy in Postmenopausal Osteoporosis: 1-Year Results from the Mobile Study," J. Bone Min. Res. 20(8):1315-1322.
Morris, J.J., et al., (1991) "Non-steroidal Antiandrogens. Design of Novel Compounds Based on an Infrared Study of the Dominant Conformation and Hydrogen-Bonding Properties of a Series of Anilide Antiandrogens," J Med Chem, 34:447-455.
Moser, C.L., and Meyer, B.K., (2011) "Comparison of Compendial Antimicrobial Effectiveness Tests: A Review," AAPS PharmaSciTech, 12:222-226.
Murrills, R.J. et al., (2004) "In vitro and in vivo Activities of C-Terminally Tuncated PTH Peptides Reveal a Disconnect Between cAMP Signaling and Functional Activity," Bone, 35:1263-1272.
Narayanan, R., et al., (2008) "Selective Androgen Receptor Modulators in Preclinical and Clinical Development," Nuclear Receptor Signaling, 6:e010.
Neer, R.M. et al., (2001) "Effect of Parathyroid Hormone (1-34) on Fractures and Bone Mineral Density in Postmenopausal Women with Osteoporosis," N Engl J Med, 344(19):1434-1441.
Nishiyama, K. K., et al., (2014) "Teriparatide Increases Strength of the Peripheral Skeleton in Premenopausal Women with Idiopathic Osteoporosis: A Pilot HR-pQCT Study," J. Clin. Endocronol. Metab. 99:2418-2425.
O'Dea, L.S., et al., "BA058, a Novel Analog of Human Parathyroid Hormone-Related Peptide (PTHrP), Induces Evidence of Bone Formation without Evidence of Bone Resorption over 7 Days of Exposure," The Endocrine Society's 89th Annual Meeting held on Jun. 2-5, 2007, (Abstract) P2-137:361 (published on May 11, 2007).
Obaidi, M., et al., (2010) "Pharmacokinetics and Pharmacodynamic of Subcutaneously (SC) Administered Doses of BA058, A Bone Mass Density Restoring Agent in Healthy Postmenopausal Women," AAPS(abstract): W5385.

Odgaard, A. and Gundersen, H.J.G., (1993) "Quantification of Connectivity in Cancellous Bone, with Special Emphasis on 3-D Reconstructions," Bone, 14:173-182.
Odgaard, A., (1997) "Three-Dimensional Methods for Quantification of Cancellous Bone Arhitecture," Bone, 20(4):315-328.
Oei, L., et al. (2013) "High Bone Mineral Density and Fracture Risk in Type 2 Diabetes as Skeletal Complications of Inadequate Glucose Control," Diabetes Care 36:1619-1628.
Okazaki, M., et al., (2008) "Prolonged signaling at the parathyroid hormone receptor by peptide ligands targeted to a specific receptor conformation," PNAS, 105(43):16525-16530.
Papapoulos, S. E., (2011) "Use of Biophosphonates in the management of postmenopausal osteoporosis," Ann. N.Y. Acad. Sci. 1218:15-32.
Patel, R.M., (2010) "Parenteral Suspension: An Overview," Int J Curr Pharm Res, 2(3):4-13.
Patsch, J. M., et al., (2013) "Increased Cortical Porosity in Type-2 Diabetic Postmenopausal Women with Fragility Fractures," J. Bone Miner. Res. 28(2):313-324.
Paudel, K.S., et al., (2010) "Challenges and opportunities in dermal/transdermal delivery," Ther Deliv, 1(1):109-131.
Pellegrini, M. et al., (1997) "Conformational Studies of RS-66271, an Analog of Parathyroid Hormone-Related Protein with Pronounced Bone Anabolic Activity," J Med Chem, 40(19):3025-3031.
Pellegrini, M. et al., (1998) "Addressing the Tertiary Structure of Human Parathyroid Hormone-(1-34)," J Biol Chem, 273(17):10420-10427.
Pellegrini, M. et al., (1999) "RS-66271, a Clinical Candidate Derived from Parathyroid Hormone Related Protein: the Role of Enhanced Amphiphilic Helicity," Peptipes: Frontiers of Peptide Science, Proceedings of the American Peptide Symposium, 15th, Nashville, Jun. 14-19, 1997, 392-393.
Perumal, O., et al., (2013) "Turning Theory into Practice: The Development of Modern Transdermal Drug Delivery systems and Future Trends," Skin Pharmacol Physiol, 26:331-342.
Pioszak, A. A., et al., (2009) "Structural Basis for Parathyroid Hormone-Related Protein Binding to the Parathyroid Hormone Receptor and Design of Conformation-Selective Peptides," J. Biol. Chem. 284(41):28382-28391.
Plotkin, H. et al., (1998) "Dissociation of Bone Formation from Resorption during 2-Week Treatment with Human Parathyroid Hormone-Related Peptide-(1-36) in Humans: Potential as an Anabolic Therapy for Osteoporosis," J Clin Endocrinol Metab, 83(8):2786-2791.
Recker, R. R., et al., (2009) "Comparative Effects of Teriparatide and Strontium Ranelate on Bone Biopsies and Biochemical Markers of Bone Turnover in Postmenopausal Women with Osteoporosis," J. Bone Min. Res. 24(8):1358-1368.
Rochira, V., et al., (2006) "Osteoporosis and Male Age-Related Hypogonadism: Role of Sex Steroids on Bone (patho)Physiology," Eur J Endocrinol, 154:175-185.
Roe, E.B. et al., (1999) "Parathyroid Hormone 1-34 (hPTH 1-34) and Estrogen Produce Dramatic Bone Density Increases in Postmenopausal Osteoporosis—Results from a Placebo-Controlled Randomized Trial," J Bone and Mineral Res, 14(Supp 1)(Abstract 1019):S137.
Rogol, A. D., "Causes of Short Stature," UptoDate, pp. 1-15, accessed May 2, 2016 at http://www.uptodate.com/contents/causes-of-short-stature?topicKey=PEDS%2F5832&elaps . . . .
Rosen, C.J., (2005) "Clinical Practice. Postmenopausal Osteoporosis," N. Engl. J. Med. 353(6):595-603.
Rosenblatt, M., (2009) "When Two Keys Fit One Lock, Surprises Follow", Nature Chem. Biol. 5(10):707-708.
Saji, S. and Sasaki, Y, Sequential Endocrine Therapy Based on Aromatase Inhibitor in Postmenopausal Women with Breast Cancer, Jpn J Breast Cancer, 2010, 25(2), 109-116.
Sebba, A. I., et al., (2004) "Response to Therapy with Once-Weekly Alendronate 70 mg Compared to Once-Weekly Risedronate 35 mg in the Treatment of Postmenopausal Osteoporosis," Curr. Med. Res. Opin. 20(12):2031-2041.
Sebba, A. I., (2008) "Significance of a Decline in Bone Mineral Density While Receiving Oral Biphosphonate Treatment," Clin. Ther. 30(3):443-452.

(56) References Cited

OTHER PUBLICATIONS

Sharon Laboratories data Sheet "Parabens.".
Silva, B. C., et al., (2014) "Trabecular Bone Score: A Noninvasive Analytical Method Based Upon the DXA Image," J. Bone Min. Res. 29(3):518-530.
Silverman, S.L., et al., (2008) "Recommendations for the Clinical Evaluation of Agents for Treatment of Osteoporosis: Conscensus of an Expert Panel Representing the American Society for Bone and Mineral Research (ASBMR), the International Society for Clinical Densitometry (ISCD), and the National Osteoporosis Foundation (NOF)," J. Bone Miner. Res. 23(1):159-165.
Singapore Intellectual Property Office, Search Report and Written Opinion for 2013078324 completed Jul. 15, 2015.
Singapore Intellectual Property Office, Written Opinion for 2013078324 completed Mar. 5, 2016.
Smith, S. Y., et al., (2013) "Eldecalcitol, a Vitamin D Analog, Reduces Bone Turnover and Increases Tabecular and Cortical Bone Mass, Density, and Strength in Ovariectomized Cynomolgus Monkeys," Bone 57:116-122.
Stellman, J.T., (2009) "Development, Production and Characterization of Plastic Hypodermic Needles," MS Thesis, Georgia Institute of Technology, pp. 1-150.
Stemke-Hale, K., et al. an Integrative Genomic and Proteomic Analysis of PIK3CA, PTEN, and AKT Mutations in Breast Cancer, Cancer Res 2008; 68: (15), Aug. 1, 2008.
Storage Conditions—Peptides International, pepnet.com/ShoppingUsers/StorageStability.aspx; Aug. 20, 2012.
Suzuki, Y., et al. (2001) "Iontophoretic Pulsatile Transdermal Delivery of Human Parathyroid Hormone (1-34)," J Pharmacy and Pharmacology, 53(9):1227-1234.
Toniolo, C., (1993) "Cα,α-Symmetrically Disubstituted Glycines: Useful Building Blocks in the Design of Conformationally Restricted Peptides", Janssen Chim. Acta, 11:10-16.
Tsai, J.N., et al., (2015) "Comparative Effects of Teriparatide, Denosumab, and Combination Therapy on Peripheral Compartmental Bone Density, Microarchitecture, and Estimated Strength: the Data-HRpQCT Study," J. Bone Miner. Res. 30(1):39-45.
Tsai, J.N., et al., (2013) "Comparative Effects of Teriparatide, Denosumab, and Combination Therapy on Peripheral Compartmental Bone Density, Microarchitecture: the Data-HRpQCT Study," Annual Meeting of the American Society of Bone and Mineral Research, Baltimore, MD.
Tucker, H., et al., (1988) "Nonsterodial Antiandrogens, Synthesis and Structure-Activity Relationships of 3-Substituted Derivatives of 2-Hydroxypropionanilides," J Med Chem, 31:954-959.
United States Patent and Trademark Office, International Search Report and Written Opinion for PCT/US16/20787 dated Jul. 22, 2016.
United States Patent and Trademark Office, International Search Report and Written Opinion for PCT/US2012/34510 completed Aug. 11, 2012 and dated Aug. 31, 2012.
United States Patent and Trademark Office, International Search Report and Written Opinion for PCT/US17/26462 completed Jun. 6, 2017 and dated Jul. 3, 2017.
United States Patent and Trademark Office, International Search Report and Written Opinion for PCT/US2016/030321 completed Jun. 27, 2016 and dated Aug. 4, 2016.
United States Patent and Trademark Office, International Search Report and Written Opinion for PCT/US2016/030316 completed Jun. 27, 2016 and dated Aug. 4, 2016.
United States Patent and Trademark Office, International Search Report and Written Opinion for PCT/US2016/030317 completed Jun. 27, 2016 and dated Aug. 4, 2016.
United States Patent and Trademark Office, International Search Report and Written Opinion for PCT/US17/53834 dated Nov. 3, 2017.
Unnanumtana, A., et al., (2010) "Current Concepts Review: The Assessment of Fracture Risk," J. Bone Joint Surg. Am. 92:743-753.
U.S. Department of Health and Human Services, Bone Health and Oseoporosis: A Report of the Surgeon General, Rockville, MD (2004).
Van Der Maaden, K., et al., (2012) "Microneedle technologies for (trans)dermal drug and vaccine delivery", J Controlled Release, 161:645-655.
Vickery, B.H. et al., (1996) "RS-66271, a C-Terminally Substituted Analog of Human Parathyroid Hormone-Related Protein (1-34), Increases Trabecular and Cortical Bone in Ovariectomized, Osteopenic Rats," J Bone Miner Res, 11(12):1943-1951.
Wright, P., "Transdermal Drug Delivery Looks for New Frontiers," Pharmaceutical Commerce, Feb. 26, 2013.
Yates, J. et al., (2014) "OR22-4: A Transdermal Patch Delivering the PTHrP1-34 Analog, Abaloparatide (BA058), Dose-Dependently Increases Spine and hip BMD Compared to Placebo," Endocrine Society's 96th Annual Meeting and Expo, Chicago, IL Jun. 21-24, 2014.
Zhang, Y., et al., (2009) "Inhibition of Peptide Acylation in PLGA Microspheres with Water-Soluble Divalent Cationic Salts," Pharm. Res. 26(8):1986-1994.
Zizic, T.M., et al., (2004) "Pharmacologic Prevention of Osteoporotic Fractures," Am Fam Physician, 70:1293-1300.
Clinical trials.gov, archive; History of Changes for Study NCT02028507; Phase III Study of Palbociclib (PD-0332991) I Combination with Endocrine therapy (Exemestane or fulvestrant) Versus Chemotherapy (Capecitaine) in Hormonal receptor (HR) Positive/HER2 Negative Metastatic Breast Cancer (MBC) Patients with Resistance to Aromatase Inhibitors, Sep. 5, 2018.
FDA Accepts IND Application for Radius Health's Investigational Drug RAD1901 Being Developed for Potential Use in Metastatic Breast Cancer, [online], Dec. 19, 2014, [search date: Mar. 4, 2020], internet: <URL: https://ir.radiuspharm.com/static-files/a1f4834f-ce20-4045-892b-da963b826cb2.
Gan Bunshi-Hyouteki CHIRYO (Molecular Targeting Therapy of Cancer), Apr. 3, 2015, 13(1), 79-84.
European Patent Office Notice of Opposition for Application No. 15769394.6 dated Oct. 10, 2023.
European Patent Office Notice of Opposition for Application No. 15769394.6 dated Oct. 24, 2023.
Robertson et al., "Comparison of the Short-Term Biological Effects of 7a[9-4,4,5,5,5-pentafluoropentylsulfinyl)-nonyl] estra-1,3,5, (1 0)-triene-3, 1713-diol (Faslodex) versus Tamoxifen in Postmenopausal Women with Primary Breast Cancer," Cancer Res, 2001, 61(18): 6739-6756.
Y.L. Wu et al., Structural Basis for an Unexpected Mode of SERM-Mediated ER Antagonism, Molecular Cell, 2005, 18, 413-424.
A.D. Leo et al., Results of the Confirm Phase III Trial Comparing Fulvestrant 250 mg With Fulvestrant 500 mg in Postmenopausal Women with Estrogen Receptor-Positive Advanced Breast Cancer, J Clin Oncol, 2010, 28(30), 4594-4600.
K.J. Kieser et al., Characterization of the Pharmacophore Properties of Novel Selective Estrogen Receptor Downregulator (SERDs), Journal of Medicinal Chemistry, 2010, 53(8), 3320-3329.
B.S. Komm et al., An overview of current emerging SERMs, Journal of Steroid Biochemistry and Molecular Biology, 2014, 143, 207-222.
A. Morikawa et al., Clinical Trials for Breast Cancer Reports, 2013, 5(4), 293-301.
WHO Durg Information, vol. 30, No. 2, 2016.
Duke University, Gruenecker, in the prosecution of EP application 15 769 394.6, May 22, 2017.
Duke University, Gruenecker, in the prosecution of EP applicatino 15 769 394.6, Sep. 1, 2020.
Kondo, N., et al., CDK4/6 Inhibitors in the Treatment of Breast Cancer, Cancer Molecular Targeted Therapy, Cancer Biology and New Seeds, vol. 13, No. 1, Medical Review Co, Ltd., Apr. 3, 2015.

\* cited by examiner

Fig. 1

| | Model | Rx-history | ER | PR | Her2 | RAD1901 |
|---|---|---|---|---|---|---|
| ER+/Her2Low | PDx-1* | Rx-naïve | + | - | + | |
| | PDx-2* | Rx-naïve | ++ | ++ | + | |
| | PDx-3* | Rx-naïve | +++ | +++ | + | |
| | PDx-4* | Rx-naïve | +++ | +++ | - | |
| ESR1 mutant | PDx-5 | AI | Y537S, ++ | +++ | + | |
| | PDx-6 | tam, AI, fulvestrant | Y537S, ++ | +++ | + | |
| ER+/Her2High | PDx-7 | Rx-naïve | ++ | - | ++ | |
| | PDx-8 | Her2i, tam, bevacizumab, chemo | + | - | +++ | |
| | PDx-9 | tam, AI, chemo | + | - | +++ | |
| | PDx-10 | AI, rituximab, chemo | ++ | - | ++ | |
| | PDx-11 | AI, fulvestrant, chemo | +++ | +++ | ++ | |
| | PDx-12* | Rx-naïve | ++ | ++ | ++ | |

(a) (b) (c)

Fig. 34A
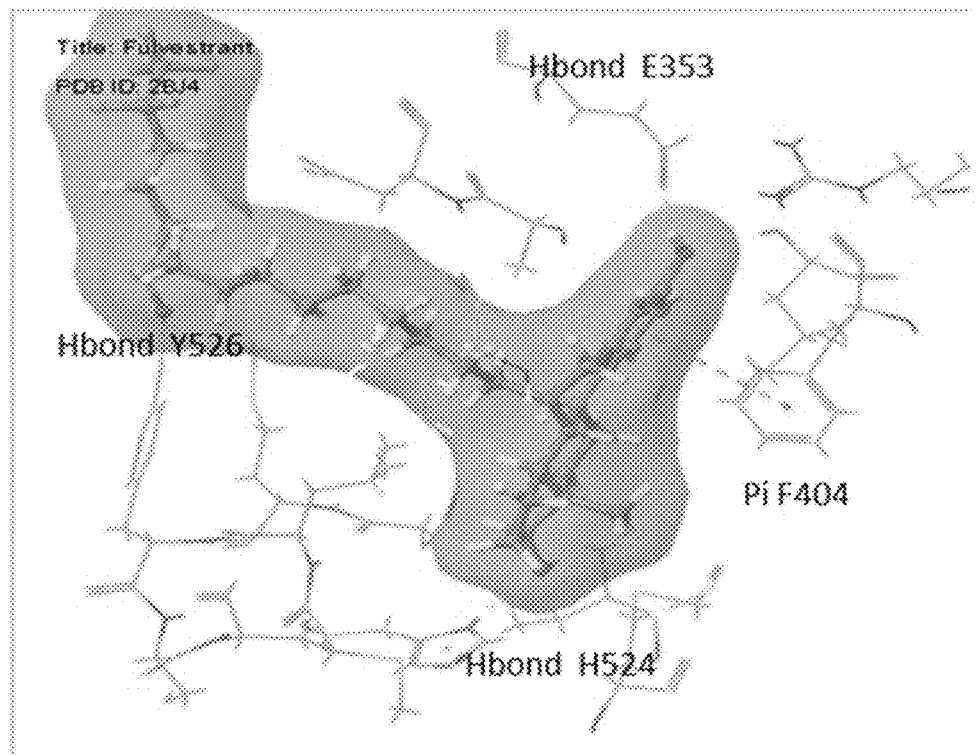
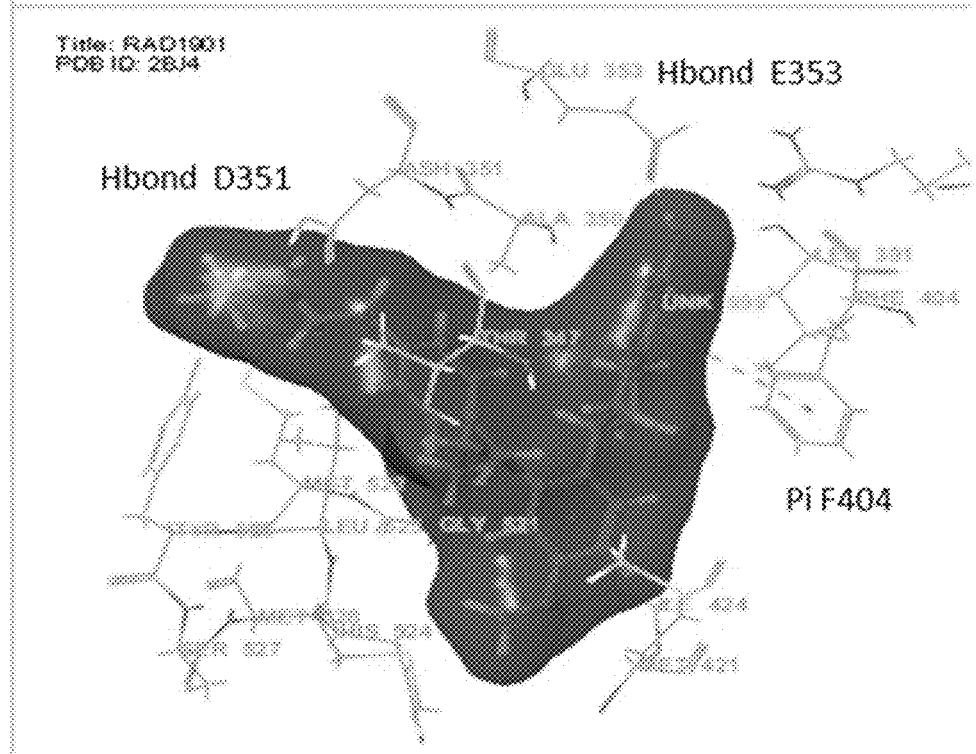
Fig. 34B

METHODS FOR TREATING CANCER

CROSS REFERENCE TO RELATED APPLICATION

This application is a continuation application of U.S. patent application Ser. No. 16/545,859, filed Aug. 20, 2019, which is a continuation application of U.S. patent application Ser. No. 15/794,910, filed Oct. 26, 2017, which is a continuation of International Application No. PCT/US2016/030316, filed Apr. 29, 2016, which claims the benefit under 35 U.S.C. § 119 of U.S. Provisional Application No. 62/154,699, filed Apr. 29, 2015, U.S. Provisional Application No. 62/155,451, filed Apr. 30, 2015, U.S. Provisional Application No. 62/252,085, filed Nov. 6, 2015, U.S. Provisional Application No. 62/265,696, filed Dec. 10, 2015, U.S. Provisional Application No. 62/158,469, filed May 7, 2015, U.S. Provisional Application No. 62/252,916, filed Nov. 9, 2015, U.S. Provisional Application No. 62/265,774, filed Dec. 10, 2015, U.S. Provisional Application No. 62/192,940, filed Jul. 15, 2015, U.S. Provisional Application No. 62/265,658, filed Dec. 10, 2015, U.S. Provisional Application No. 62/323,572, filed Apr. 15, 2016, U.S. Provisional Application No. 62/192,944, filed Jul. 15, 2015, U.S. Provisional Application No. 62/265,663, filed Dec. 10, 2015, and U.S. Provisional Application No. 62/323,576, filed Apr. 15, 2016. The entire contents of the aforementioned applications are hereby incorporated by reference herein in their entirety, including drawings.

BACKGROUND

Breast cancer is divided into three subtypes based on expression of three receptors: estrogen receptor (ER), progesterone receptor (PR), and human epidermal growth factor receptor-2 (Her2). Overexpression of ERs is found in many breast cancer patients. ER-positive (ER+) breast cancers comprise two-thirds of all breast cancers. Other than breast cancer, estrogen and ERs are associated with, for example, ovarian cancer, colon cancer, prostate cancer and endometrial cancer.

ERs can be activated by estrogen and translocate into the nucleus to bind to DNA, thereby regulating the activity of various genes. See, e.g., Marino et al., "Estrogen Signaling Multiple Pathways to Impact Gene Transcription," *Curr. Genomics* 7(8): 497-508 (2006); and Heldring et al., "Estrogen Receptors: How Do They Signal and What Are Their Targets," *Physiol. Rev.* 87(3): 905-931 (2007).

Agents that inhibit estrogen production, such as aromatase inhibitors (AIs, e.g., letrozole, anastrozole and aromasin), or those that directly block ER activity, such as selective estrogen receptor modulators (SERMs, e.g., tamoxifen, toremifene, droloxifene, idoxifene, raloxifene, lasofoxifene, arzoxifene, miproxifene, levormeloxifene, and EM-652 (SCH 57068)) and selective estrogen receptor degraders (SERDs, e.g., fulvestrant, TAS-108 (SR16234), ZK191703, RU58668, GDC-0810 (ARN-810), GW5638/DPC974, SRN-927, ICI182782 and AZD9496), have been used previously or are being developed in the treatment of ER-positive breast cancers.

SERMs (e.g., tamoxifen) and AIs are often used as a first-line adjuvant systemic therapy for ER-positive breast cancer. Tamoxifen is commonly used for ER-positive breast cancer. AIs suppress estrogen production in peripheral tissues by blocking the activity of aromatase, which turns androgen into estrogen in the body. However, AIs cannot stop the ovaries from making estrogen, Thus, AIs are mainly used to treat postmenopausal women. Furthermore, as AIs are much more effective than tamoxifen with fewer serious side effects, AIs may also be used to treat premenopausal women with their ovarian function suppressed. See, e.g., Francis et al., "Adjuvant Ovarian Suppression in Premenopausal Breast Cancer," *N. Engl. J. Med.*, 372:436-446 (2015).

While initial treatment with these agents may be successful, many patients eventually relapse with drug-resistant breast cancers. Mutations affecting the ER have emerged as one potential mechanism for the development of this resistance. See, e.g., Robinson et al., "Activating ESR1 mutations in hormone-resistant metastatic breast cancer," *Nat. Genet.* 45:1446-51 (2013). Mutations in the ligand-binding domain (LBD) of ER are found in 21% metastatic ER-positive breast tumor samples from patients who received at least one line of endocrine treatment. Jeselsohn, et al., "ESR1 mutations—a mechanism for acquired endocrine resistance in breast cancer," *Nat. Rev. Clin. Oncol.*, 12:573-83 (2015).

Fulvestrant is currently the only SERD approved for the treatment of ER-positive metastatic breast cancers with disease progression following antiestrogen therapy. Despite its clinical efficacy, the utility of fulvestrant has been limited by the amount of drug that can be administered in a single injection and by reduced bioavailability. Imaging studies using 18F-fluoroestradiol positron emission tomography (FES-PET) suggest that even at the 500 mg dose level, some patients may not have complete ER inhibition, and insufficient dosing may be a reason for therapeutic failure.

Another challenge associated with estrogen-directed therapies is that they may have undesirable effects on uterine, bone, and other tissues. The ER directs transcription of estrogen-responsive genes in a wide variety of tissues and cell types. These effects can be particularly pronounced as endogenous levels of estrogen and other ovarian hormones diminish during menopause. For example, tamoxifen can cause bone thinning in premenopausal women and increase the risk of endometrial cancer because it acts as a partial agonist on the endometrium. In postmenopausal women, AIs can cause more bone loss and more broken bones than tamoxifen. Patients treated with fulvestrant may also be exposed to the risk of osteoporosis due to its mechanism of action.

The phosphoinositide 3-kinase (PI3K)/protein kinase B (AKT)/mammalian target of rapamycin (mTOR) pathway is an intracellular signaling pathway important in regulating the cell cycle. The frequent activation of the PI3K/AKT/mTOR pathway in cancer and its crucial role in cell growth and survival provide a challenge in finding an appropriate amount of proliferation versus differentiation in order to utilize this balance in the development of various therapies. See, e.g., Gitto et al., "Recent insights into the pathophysiology of mTOR pathway dysregulation," *Res. Rep. Bio.*, 2:1-16 (2015).

Inhibitors of the PI3K pathway have shown the most promise when given in combination with other therapies. For example, everolimus, an allosteric mTOR inhibitor, was approved in 2012 for use in combination with the AI exemestane for treating post-menopausal women with advanced hormone receptor positive (HR+), HER2– breast cancer (BOLERO-2 study). Agents targeting other components of the PI3K pathway are under development for treating HR+ cancer, e.g., ATP-competitive dual inhibitors of PI3K and mTOR (e.g., BEZ235, GDC-0980), pan-PI3K inhibitors which inhibit all four isoforms of class I PI3K (e.g., BKM120, GDC-0941), isoform-specific inhibitors of the various PI3K isoforms (e.g., BYL719, GDC-0032), allosteric and catalytic inhibitors of AKT (MK2206, GDC-0068, GSK2110183, GSK2141795, AZD5363), and ATP-competitive inhibitors of mTOR only (AZD2014, MLN0128, and CC-223). Dienstmann et al., "Picking the point of inhibition: a comparative review of PI3K/AKT/mTOR pathway inhibitors," *Mol. Cancer Ther.*, 13(5):1021-31 (2014).

Despite their great potential, undesirable side effects associated with mTOR inhibitors have hindered their development as effective cancer therapies. Kaplan et al., "Strategies for the management of adverse events associated with mTOR inhibitors," *Transplant Rev (Orlando)*, 28(3): 126-133 (2014); and Pallet et al., "Adverse events associated with mTOR inhibitors," *Expert Opin. Drug Saf.* 12(2): 177-186 (2013).

There remains a need for more durable and effective ER-targeted therapies that can overcome challenges associated with the current endocrine therapies, while providing additional benefits by combining with second therapeutic agents (e.g., everolimus and other agents targeting the PI3K/AKT/mTOR pathway) to combat cancer in advanced stage and/or with resistance to prior treatments.

BRIEF SUMMARY OF THE INVENTION

One aspect of the invention relates to a method for treating one or more cancers and/or tumors in a subject comprising administering to the subject a therapeutically effective amount of a combination of RAD1901 or solvates (e.g., hydrate) or salts thereof and one or more second therapeutic agent(s) (e.g., everolimus) as described herein.

In some embodiments, the cancer is an estrogen-dependent cancer, such as breast cancer, ovarian cancer, colon cancer, endometrial cancer, or prostate cancer. In some embodiments, the cancer is ER-positive breast cancer.

RAD1901 or solvates (e.g., hydrate) or salts thereof and the second therapeutic agent(s) (e.g., everolimus) are administered in combination to a subject in need. The phrase "in combination" means that RAD1901 or solvates (e.g., hydrate) or salts thereof may be administered before, during, or after the administration of the second therapeutic agent(s) (e.g., everolimus). For example, RAD1901 or solvates (e.g., hydrate) or salts thereof and the second therapeutic agent(s) can be administered about one week apart, about 6 days apart, about 5 days apart, about 4 days apart, about 3 days apart, about 2 days apart, about 24 hours apart, about 23 hours apart, about 22 hours apart, about 21 hours apart, about 20 hours apart, about 19 hours apart, about 18 hours apart, about 17 hours apart, about 16 hours apart, about 15 hours apart, about 14 hours apart, about 13 hours apart, about 12 hours apart, about 11 hours apart, about 10 hours apart, about 9 hours apart, about 8 hours apart, about 7 hours apart, about 6 hours apart, about 5 hours apart, about 4 hours apart, about 3 hours apart, about 2 hours apart, about 1 hour apart, about 55 minutes apart, about 50 minutes apart, about 45 minutes apart, about 40 minutes apart, about 35 minutes apart, about 30 minutes apart, about 25 minutes apart, about 20 minutes apart, about 15 minutes apart, about 10 minutes apart, or about 5 minutes apart. In other embodiments, RAD1901 or solvates (e.g., hydrate) or salts thereof and the second therapeutic agent(s) are administered to the subject simultaneously or substantially simultaneously. In certain of these embodiments, the compounds may be administered as part of a single formulation.

In some embodiments, RAD1901 or solvates (e.g., hydrate) or salts thereof and the second therapeutic agent(s) are administered in separate formulations. In certain of these embodiments, the formulations may be of the same type. For example, both formulations may be designed for oral administration (e.g., via two separate pills) or for injection (e.g., via two separate injectable formulations). In other embodiments, RAD1901 or solvates (e.g., hydrate) or salts thereof and the second therapeutic agent(s) may be formulated in different types of formulations. For example, one compound may be in a formulation designed for oral administration, while the other is in a formulation designed for injection.

In other embodiments, RAD1901 or solvates (e.g., hydrate) or salts thereof and the second therapeutic agent(s) are administered as part of a single formulation. For example, RAD1901 or solvates (e.g., hydrate) or salts thereof and the second therapeutic agent(s) are formulated in a single pill for oral administration or in a single dose for injection. Accordingly, provided herein in certain embodiments are formulations comprising RAD1901 or solvates (e.g., hydrate) or salts thereof and one or more second therapeutic agents.

Administration routes of RAD1901 or solvates (e.g., hydrate) or salts thereof and/or the second therapeutic agent(s) include but are not limited to topical administration, oral administration, intradermal administration, intramuscular administration, intraperitoneal administration, intravenous administration, intravesical infusion, subcutaneous administration, transdermal administration, and transmucosal administration.

BRIEF DESCRIPTION OF DRAWINGS AND TABLES

This application contains at least one drawing executed in color. Copies of this application with color drawing(s) will be provided by the Office upon request and payment of the necessary fees.

FIG. 1: RAD1901 inhibited tumor growth in various patient-derived xenograft (PDx) models regardless of ESR1 status and prior endocrine therapy. Percentage of tumor growth inhibition (TGI) in PDx models treated with RAD1901 is shown.

Figure 2B:
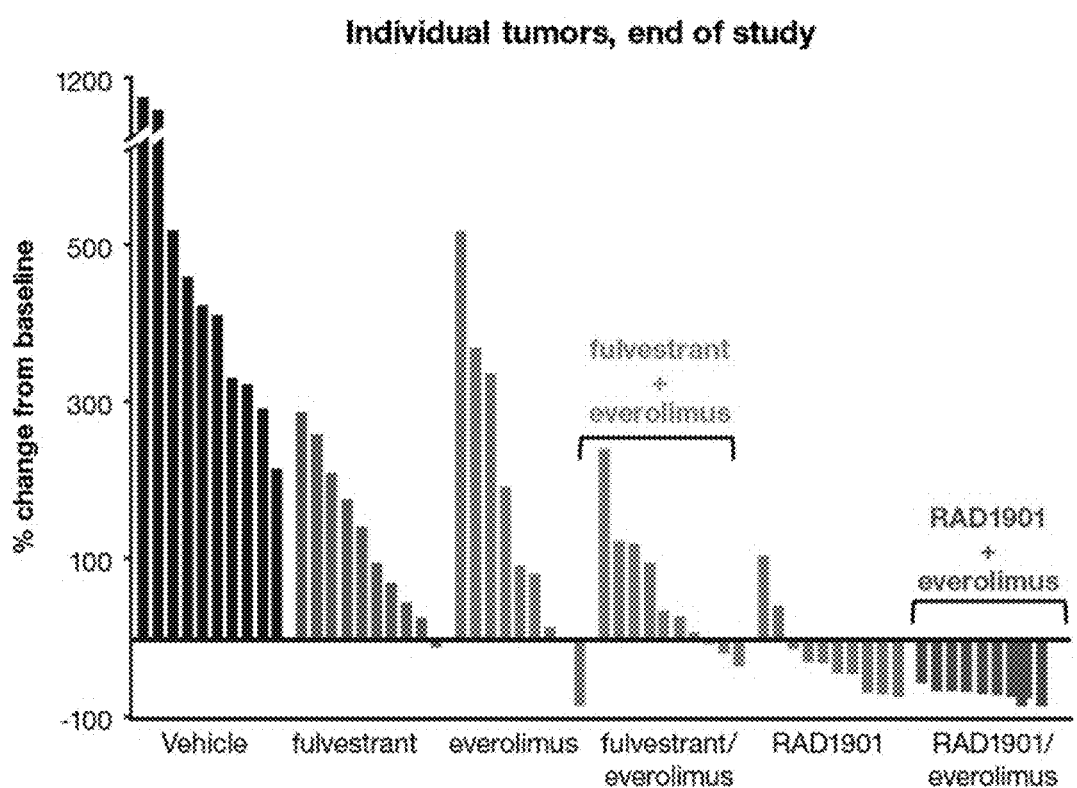
Figure 2C:
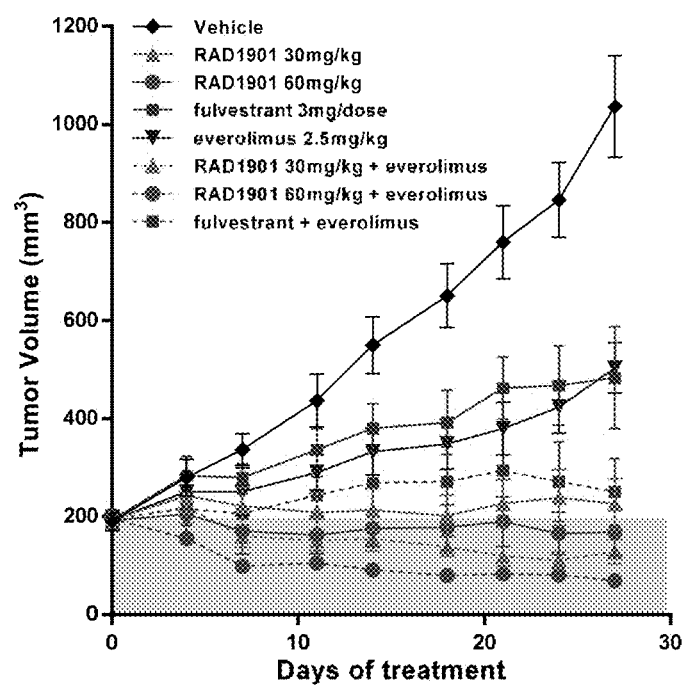

FIGS. 2A-C: The combination of RAD1901 and everolimus demonstrated tumor growth inhibition and regression in wild-type (WT) ERα MCF-7 xenograft models (PR+, HER2−). (A): Tumor growth of MCF-7 xenograft models treated with vehicle control, everolimus (2.5 mg/kg, p.o., q.d), fulvestrant (3 mg/dose, s.c., qwk), a combination of fulvestrant (3 mg/dose, s.c., qwk) and everolimus (2.5 mg/kg, p.o., q.d), RAD1901 (60 mg/kg, p.o., q.d.), and a combination of RAD1901 (60 mg/kg, p.o., q.d.) and everolimus (2.5 mg/kg, p.o., q.d); One-way ANOVA, "ns" is not significant, *p-value<0.05, and ***p-value<0.001; (B): Change in individual tumor size from baseline to end of study of MCF-7 xenograft models treated with vehicle control, everolimus (2.5 mg/kg, p.o., q.d), fulvestrant (3 mg/dose, s.c., qwk), a combination of fulvestrant (3 mg/dose, s.c., qwk) and everolimus (2.5 mg/kg, p.o., q.d), RAD1901 (60 mg/kg, p.o., q.d.), and combinations of RAD1901 (60 mg/kg, p.o., q.d.) and everolimus (2.5 mg/kg, p.o., q.d); (C): Tumor growth of MCF-7 xenograft models treated with vehicle control, everolimus (2.5 mg/kg, p.o., q.d), fulvestrant (3 mg/dose, s.c., qwk), a combination of fulvestrant (3 mg/dose, s.c., qwk) and everolimus (2.5 mg/kg, p.o., q.d), RAD1901 (30 or 60 mg/kg, p.o., q.d.), and a combination of RAD1901 (30 or 60 mg/kg, p.o., q.d.) and everolimus (2.5 mg/kg, p.o., q.d).

Figure 3A:
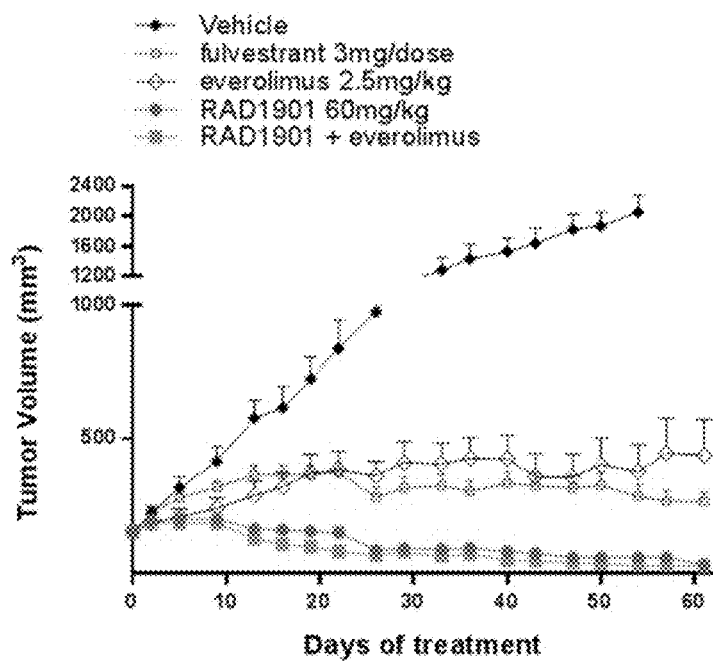
Figure 3B:
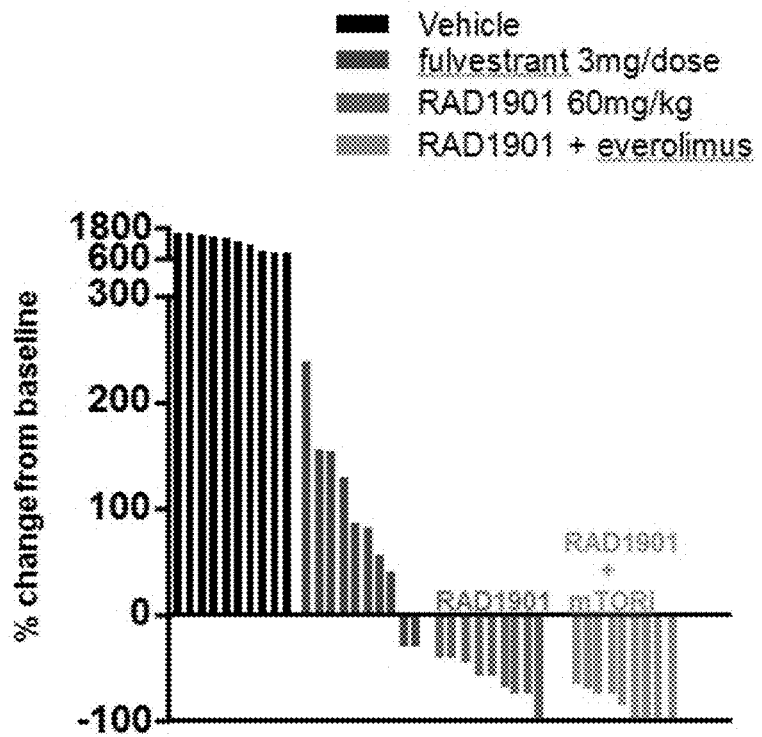

FIGS. 3A-B: The combination of RAD1901 and everolimus demonstrated tumor growth inhibition and regression in WT ERα PDx-11 models (PR+, Her2+, previously treated with aromatase inhibitor, fulvestrant, and chemotherapy). (A): Tumor growth of PDx-11 models treated with vehicle control, fulvestrant (3 mg/dose, s.c., qwk), everolimus (2.5 mg/kg, p.o., q.d), RAD1901 (60 mg/kg, p.o., q.d.), and a combination of RAD1901 (60 mg/kg, p.o., q.d.) and everolimus (2.5 mg/kg, p.o., q.d); (B): Change in individual tumor size from baseline to end of study in PDx-11 models treated with vehicle control, fulvestrant (3 mg/dose, s.c., qwk), RAD1901 (60 mg/kg, p.o., q.d.), and a combination of RAD1901 (60 mg/kg, p.o., q.d.) and everolimus (2.5 mg/kg, p.o., q.d). n=8-10/group.

Figure 4A:
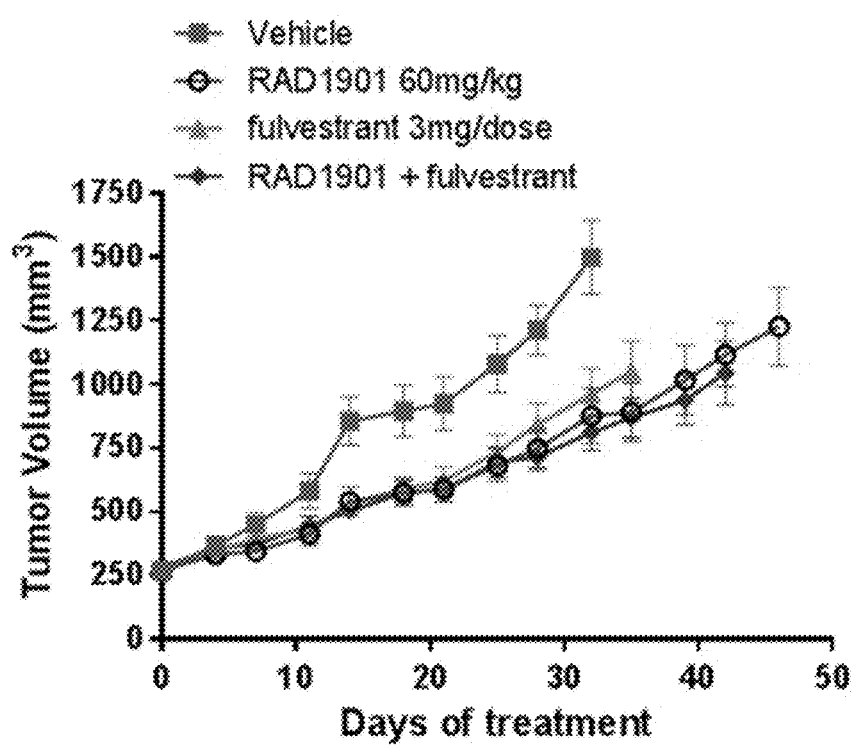
Figure 4B:
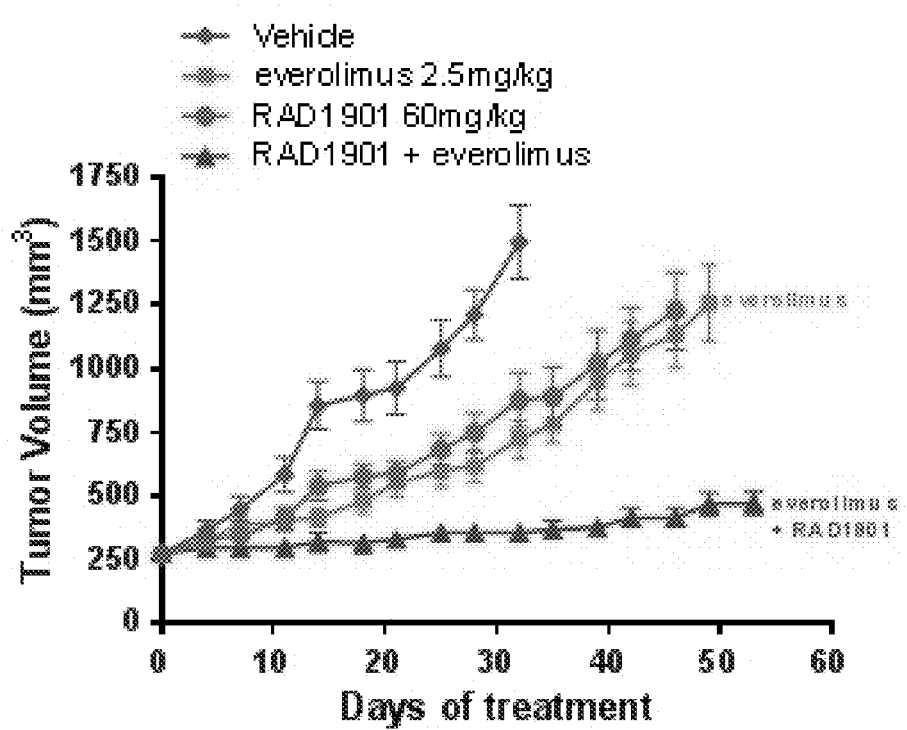

FIGS. 4A-B: The combination of RAD1901 and everolimus demonstrated tumor growth inhibition in WT ER+ PDx-2 models (PR+, Her2+, treatment naïve). (A): Tumor growth of PDx-2 models treated with vehicle control, RAD1901 (60 mg/kg, p.o., q.d.), fulvestrant (3 mg/dose, s.c., qwk), and a combination of RAD1901 (60 mg/kg, p.o., q.d.) and fulvestrant (3 mg/dose, s.c., qwk); (B): Tumor growth of PDx-2 models treated with vehicle control, everolimus (2.5 mg/kg, p.o., q.d), RAD1901 (60 mg/kg, p.o., q.d.), and a combination of RAD1901 (60 mg/kg, p.o., q.d.) and everolimus (2.5 mg/kg, p.o., q.d). n=8-10/group.

Figure 5:
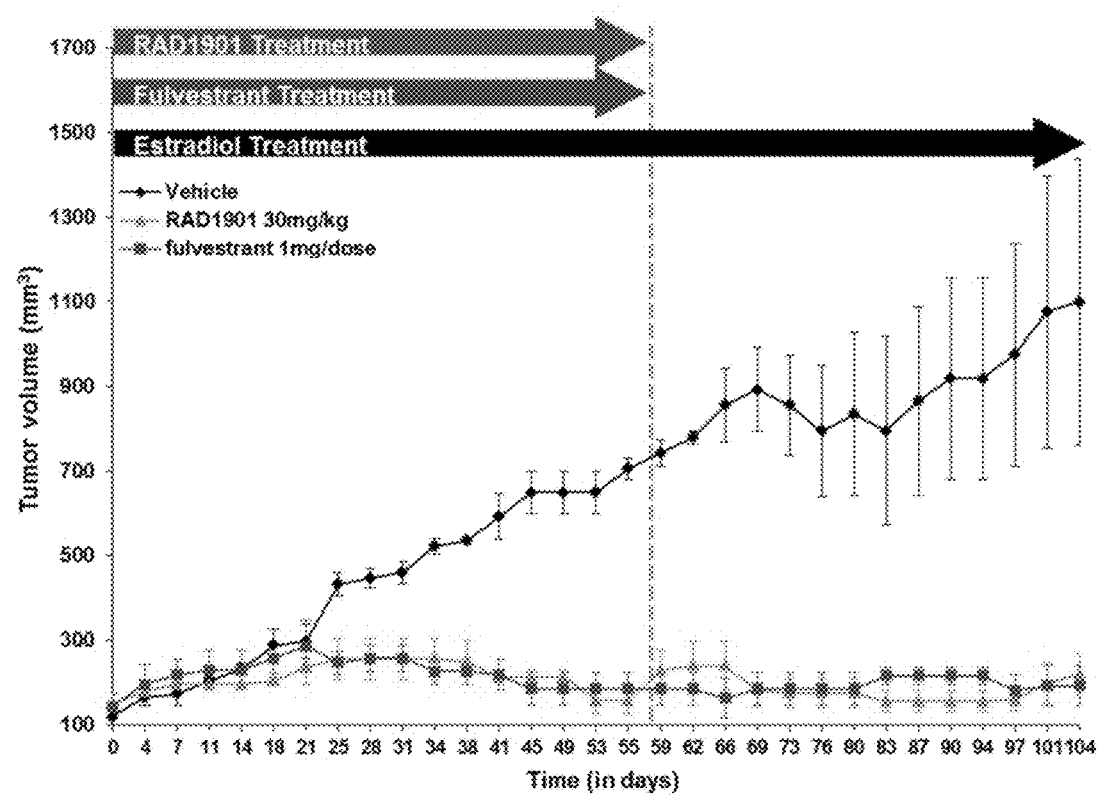

FIG. 5: Efficacy of RAD1901 sustained at least two months after RAD1901 treatment ended while estradiol treatment continued in WT ERα PDx-4 models (PR+, Her2+, treatment naïve).

Figure 6A:
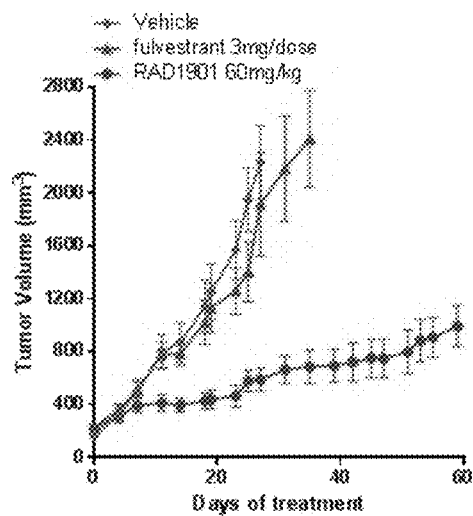
Figure 6B:
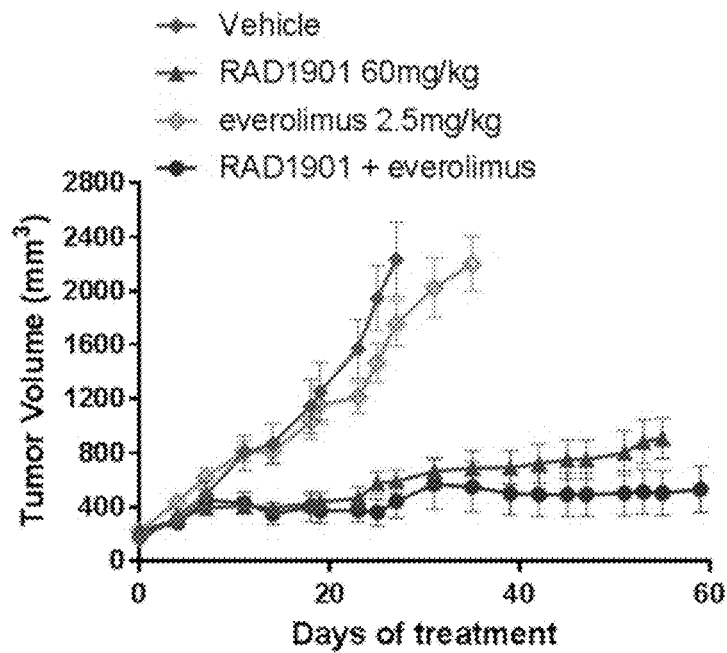

FIGS. 6A-B: The combination of RAD1901 and everolimus demonstrated tumor growth inhibition in mutant (Y537S) ERα PDx-5 models (PR+, Her2+, previously treated with aromatase inhibitors). (A): Tumor growth of PDx-5 models treated with vehicle control, RAD1901 (60 mg/kg, p.o., q.d.), and fulvestrant (3 mg/kg, s.c., qwk); (B): Tumor growth of PDx-5 models treated with vehicle control, RAD1901 (60 mg/kg, p.o., q.d.), everolimus (2.5 mg/kg, p.o., q.d), and a combination of RAD1901 (60 mg/kg, p.o., q.d.) and everolimus (2.5 mg/kg, p.o., q.d). n=8-10/group.

Figure 7:
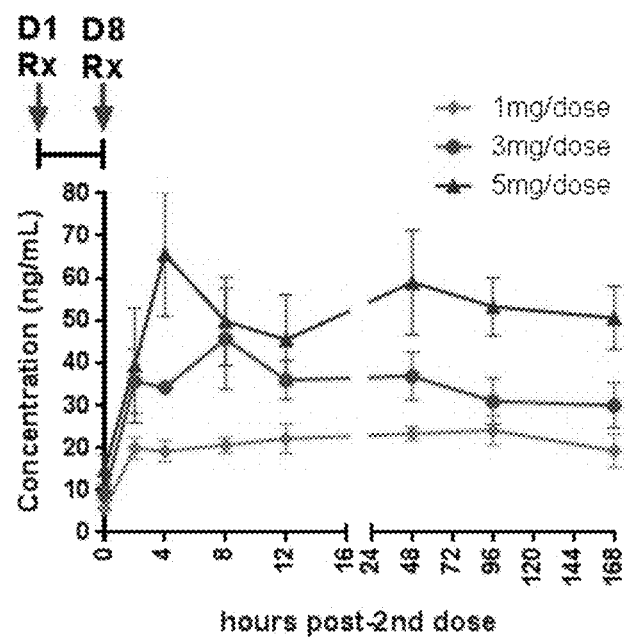

FIG. 7: Pharmacokinetic analysis of fulvestrant in nude mice. The plasma concentration of fulvestrant at 1 mg/dose (solid diamond), 3 mg/dose (solid circle), and 5 mg/dose (solid triangle) is shown. The nude mice were dosed subcutaneously with fulvestrant on Day 1 and the second dose on Day 8. The plasma concentration of fulvestrant was monitored at the indicated time points for up to 168 hours after the second dose.

Figure 8:
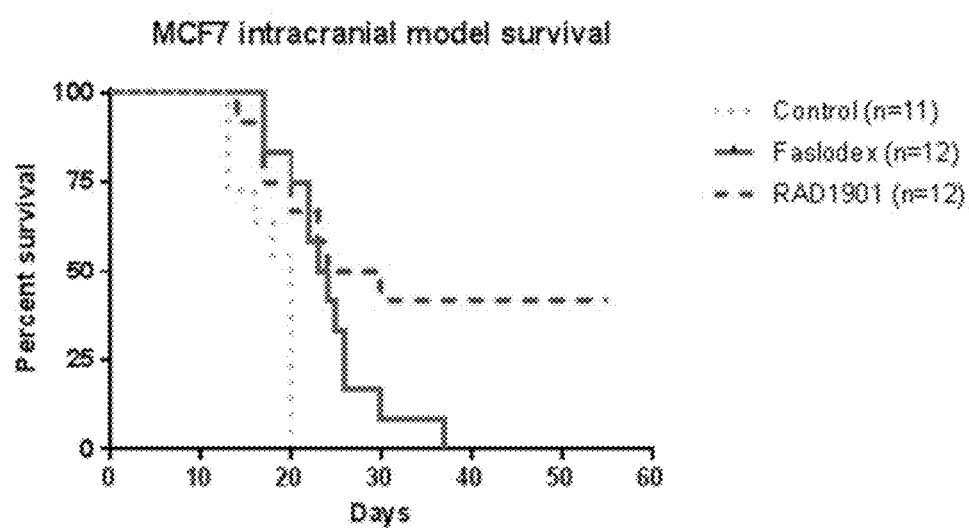

FIG. 8: Effect of RAD1901 and fulvestrant (Faslodex) on mouse survival in an intracranial MCF-7 tumor model.

Figure 9A:
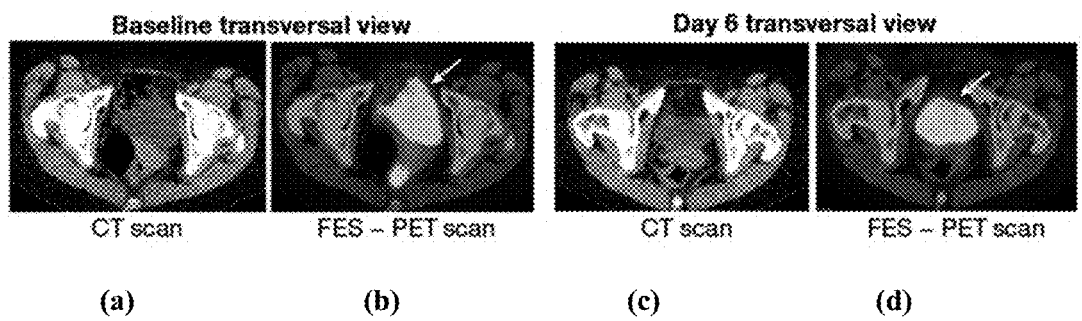
Figure 9B:
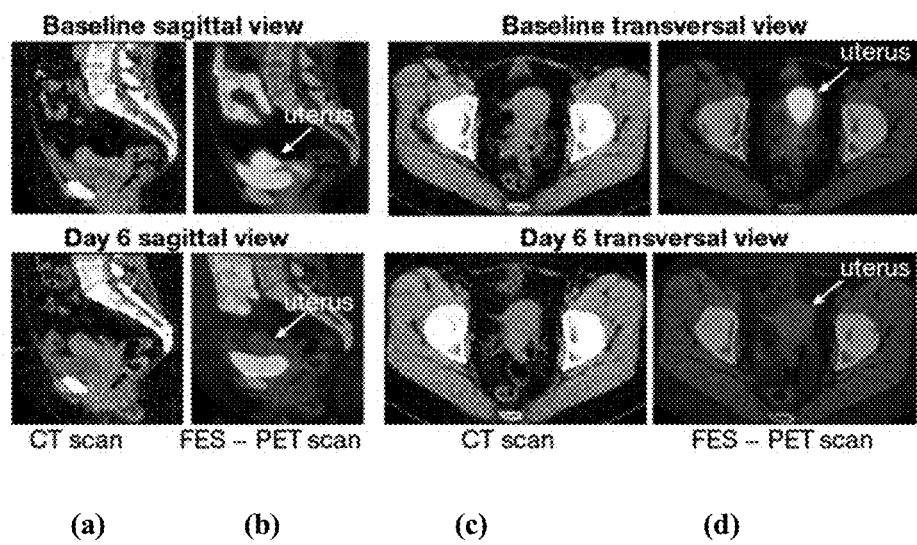
Figure 9C:
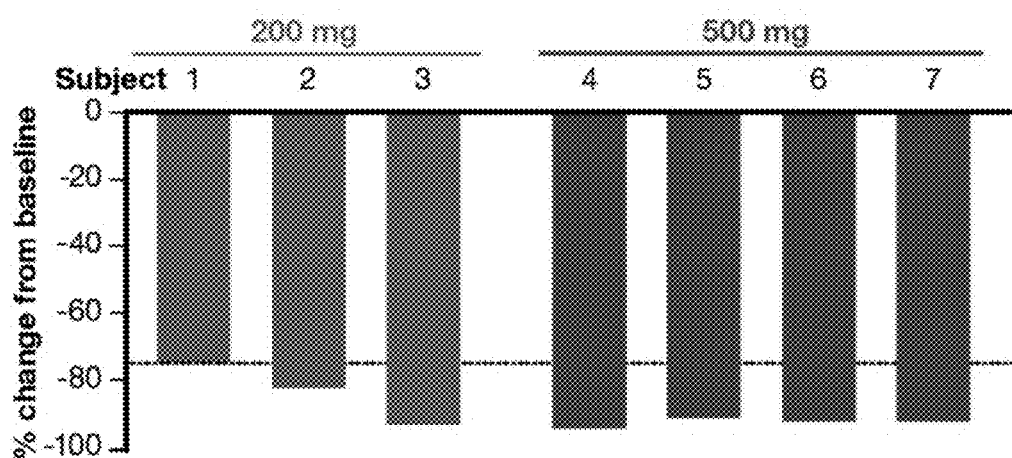

FIGS. 9A-C: A representative image of FES-PET scan of the uterus of a subject treated with 200 and 500 mg RAD1901 p.o., q.d., and change of the ER engagement after the RAD1901 treatments. (A): Transversal view of uterus CT scan before 200 mg RAD1901 treatment (a) and after (c), and transversal view of uterus FES-PET scan before the RAD1901 treatment (b) and after (d); (B): Sagittal view of uterus CT scan before 500 mg RAD1901 treatment (top (a) panel) and after (bottom (a) panel), sagittal view of uterus FES-PET scan before the RAD1901 treatment (top (b) panel) and after (bottom (b) panel), transversal view of uterus CT scan before the RAD1901 treatment (top (c) panel) and after (bottom (c) panel), transversal view of uterus FES-PET scan before the RAD1901 treatment (top (d) panel) and after (bottom (d) panel); (C): % change of ER engagement after the RAD1901 treatments of Subjects 1-3 (200 mg) and Subjects 4-7 (500 mg) compared to baseline (before RAD1901 treatment).

Figure 10A:
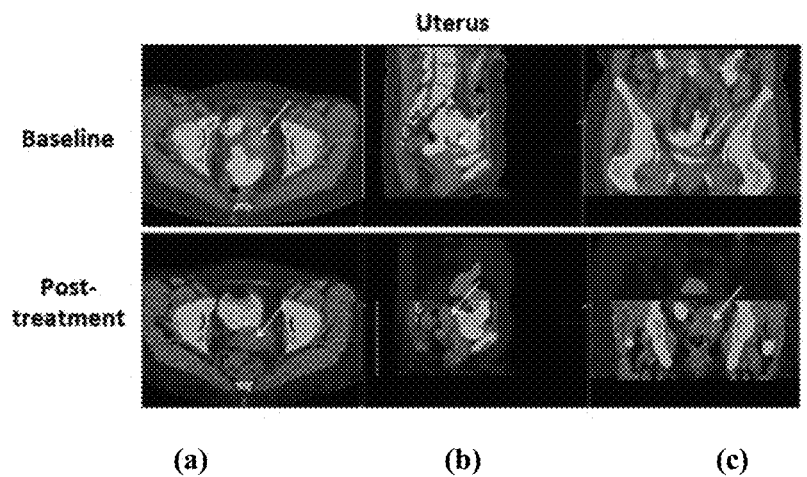
Figure 10B:
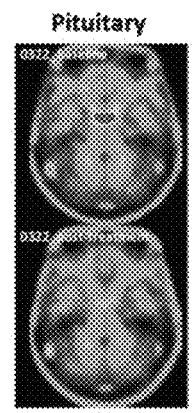

FIGS. 10A-B: A representative image of FES-PET scan of the uterus (A) and pituitary (B) before (Baseline) and after (Post-treatment) RAD1901 treatment (500 mg). (a) Lateral cross-section; (b) longitude cross-section; and (c) longitude cross-section.

Figure 11:
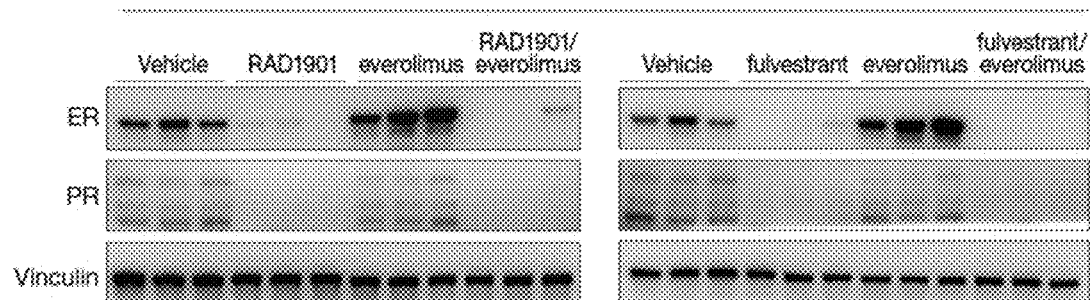

FIG. 11: PR and ER expression in MCF-7 xenograft models treated with vehicle control, RAD1901, everolimus, a combination of RAD1901 and everolimus, fulvestrant, and a combination of fulvestrant and everolimus.

Figure 12A:
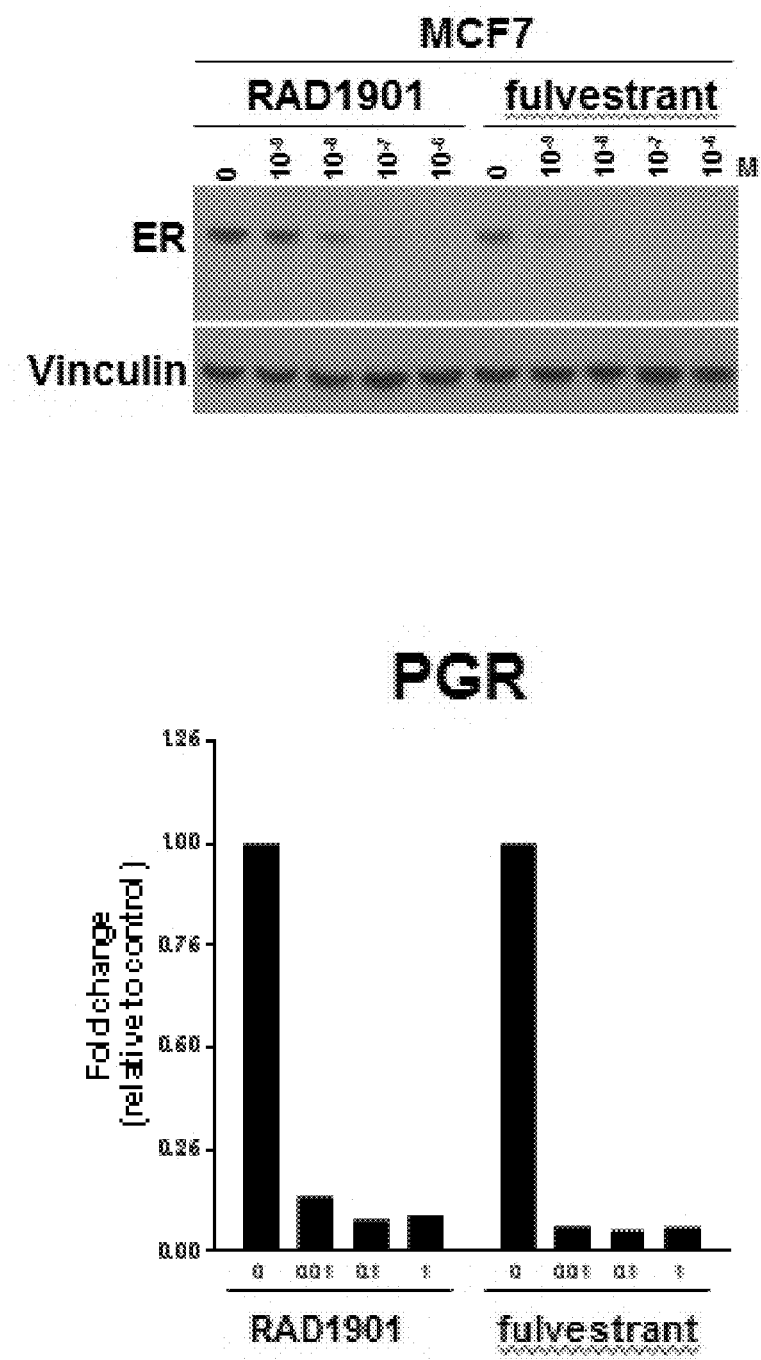
Figure 12A:
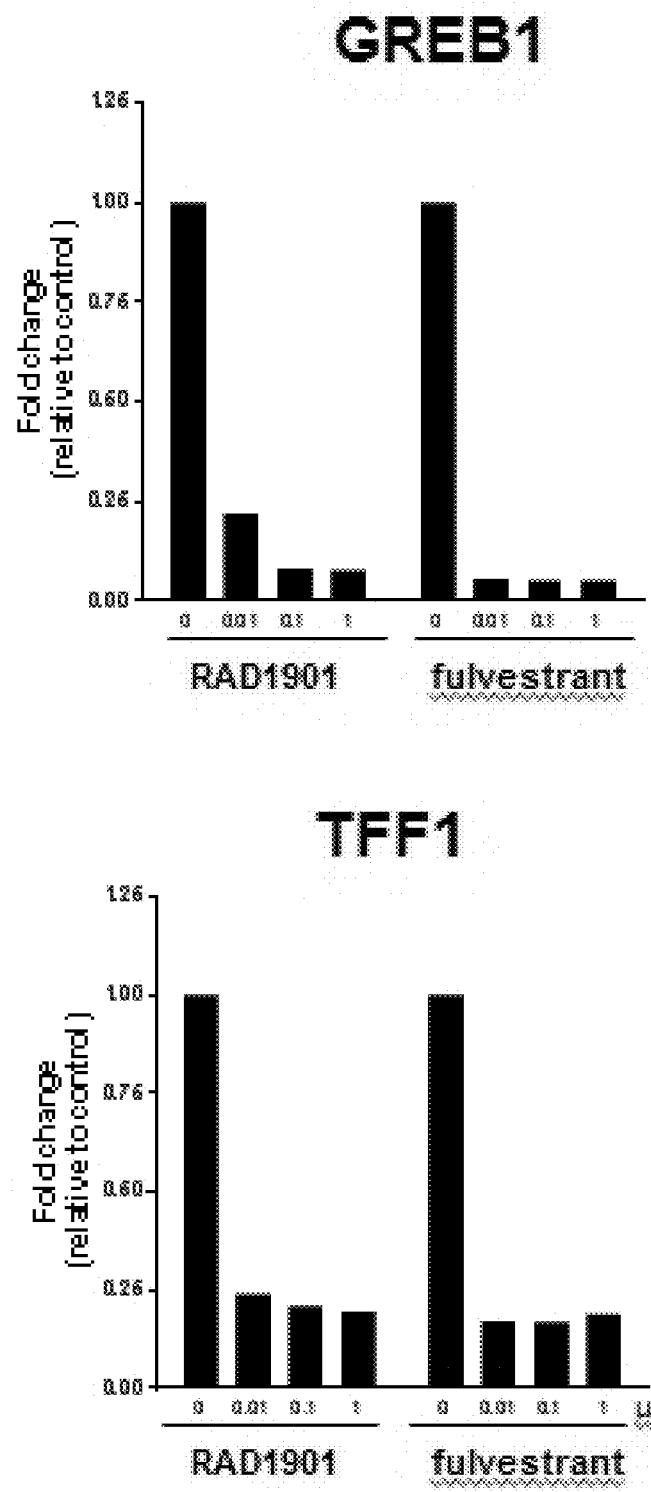
Figure 12B:
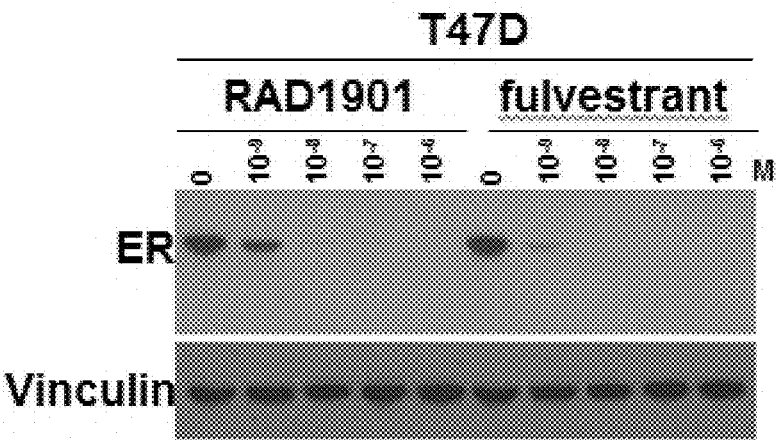
Figure 12B:
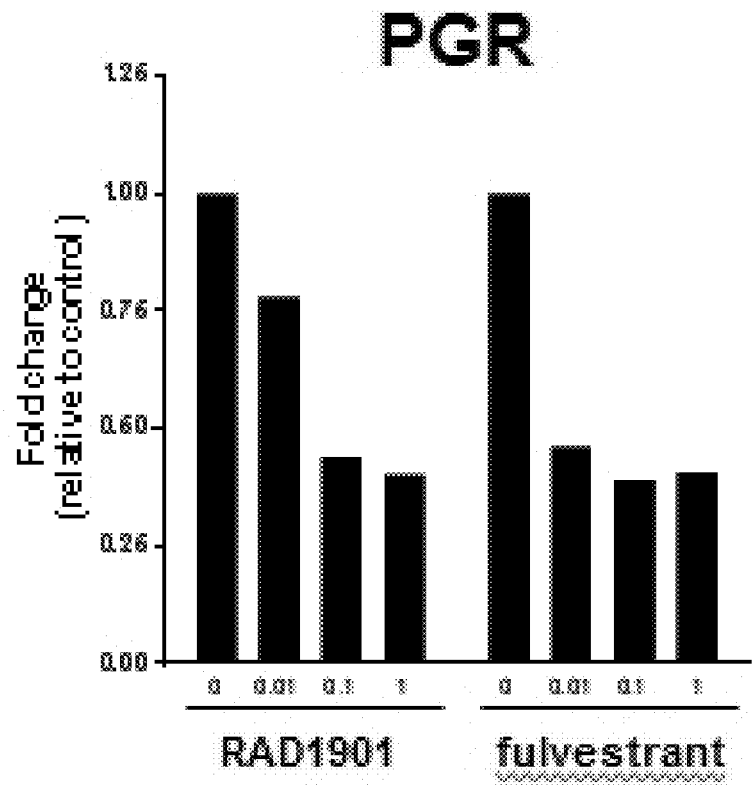
Figure 12B:
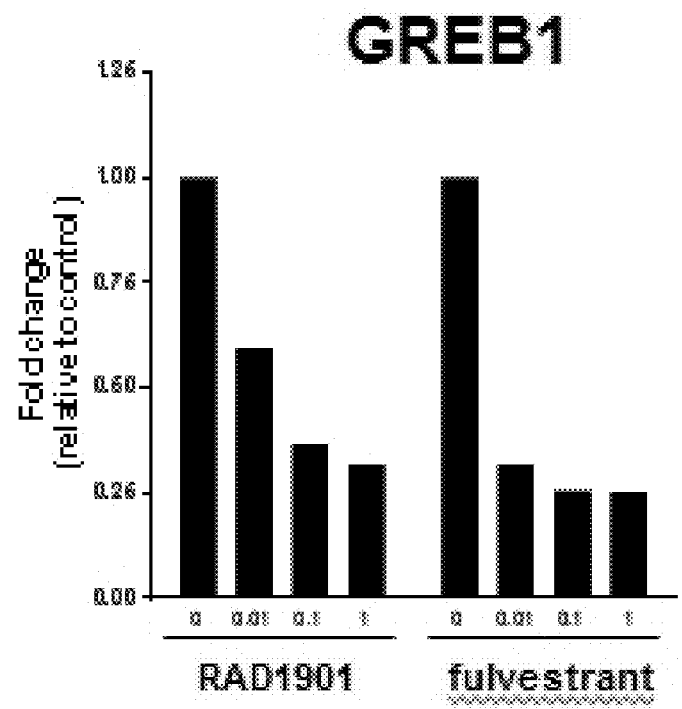
Figure 12B:
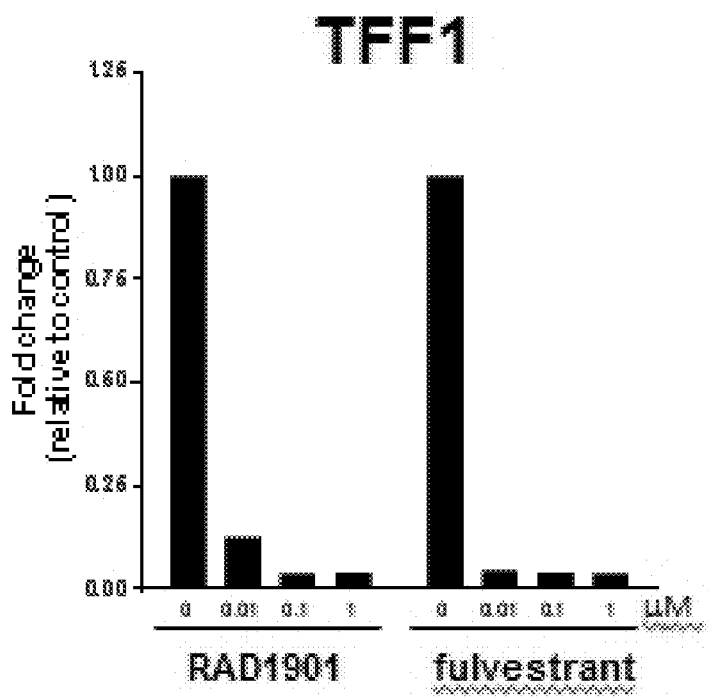

FIGS. 12A-B: RAD1901 treatment resulted in complete ER degradation and inhibited ER signaling in MCF-7 cell lines (A) and T47D cell lines (B) in vitro. The ER expression was shown in both cell lines treated with RAD1901 and fulvestrant at various concentrations of 0.001 µM, 0.01 µM, 0.1 µM and 1 µM, respectively. ER signaling was shown by three ER target genes tested: PGR, GREB1 and TFF1.

Figure 13A:
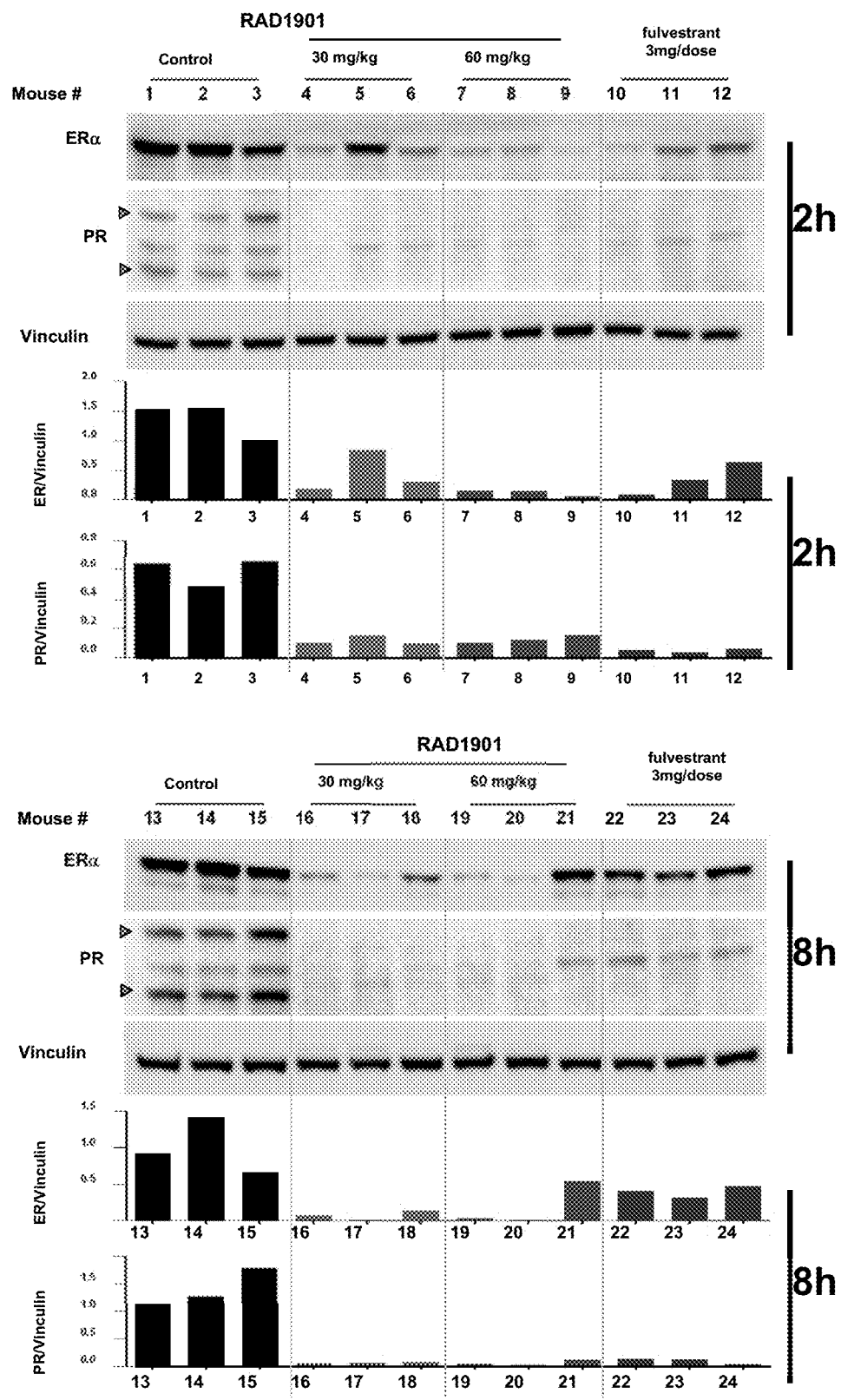
Figure 13B:
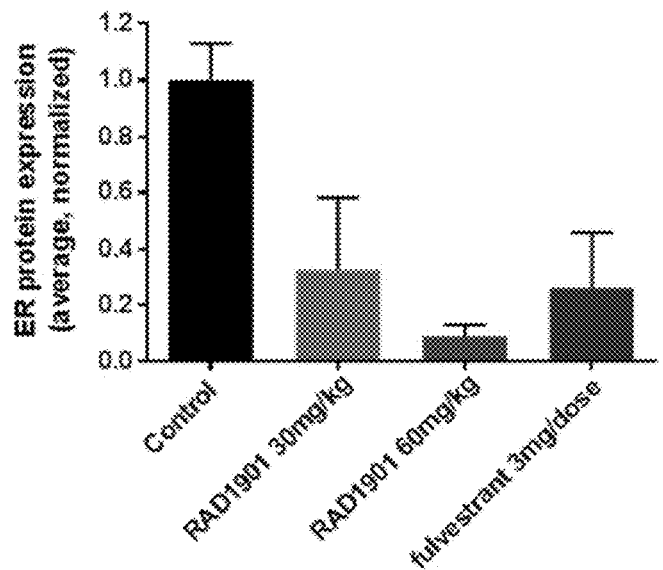
Figure 13C:
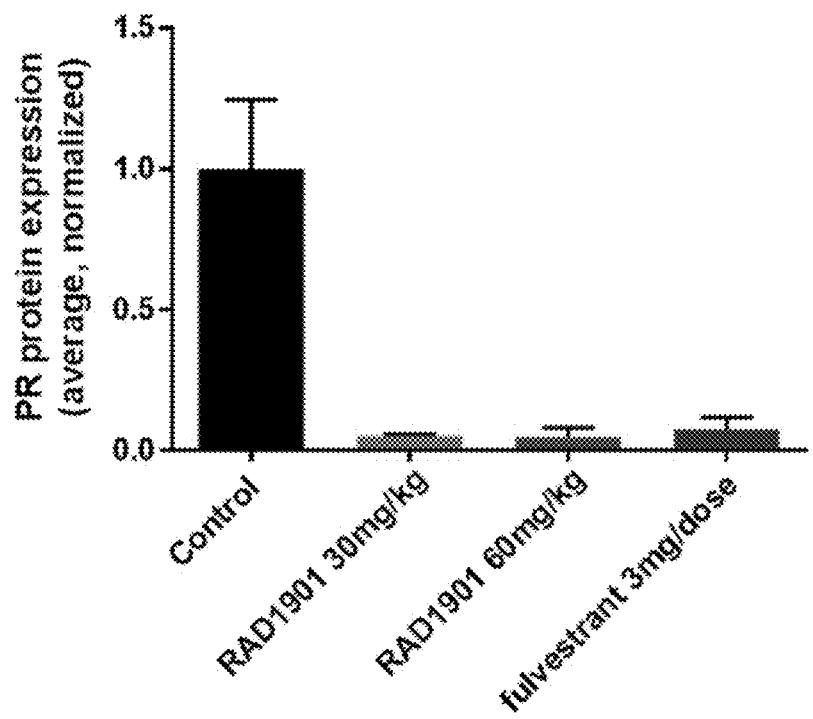

FIGS. 13A-C: RAD1901 treatment resulted in ER degradation and abrogation of ER signaling in MCF-7 xenograft models. (A): Western blot showing PR and ER expression in the MCF-7 xenograft models treated with vehicle control, RAD1901 at 30 and 60 mg/kg, and fulvestrant at 3 mg/dose, 2 hour or 8 hour after the last dose; (B): ER protein expression in the MCF-7 xenograft models treated with vehicle control, RAD1901 at 30 and 60 mg/kg, and fulvestrant at 3 mg/dose, 2 hour after the last dose; (C): PR protein expression in the MCF-7 xenograft models treated with vehicle control, RAD1901 at 30 and 60 mg/kg, and fulvestrant at 3 mg/dose, 8 hour after last dose.

Figure 14A:
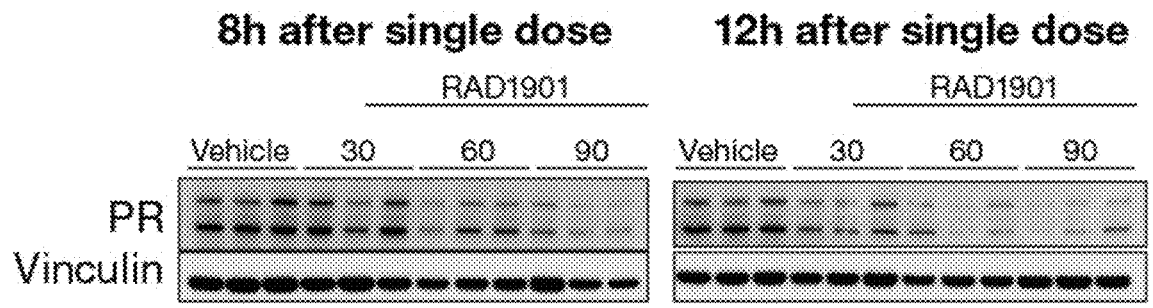
Figure 14B:
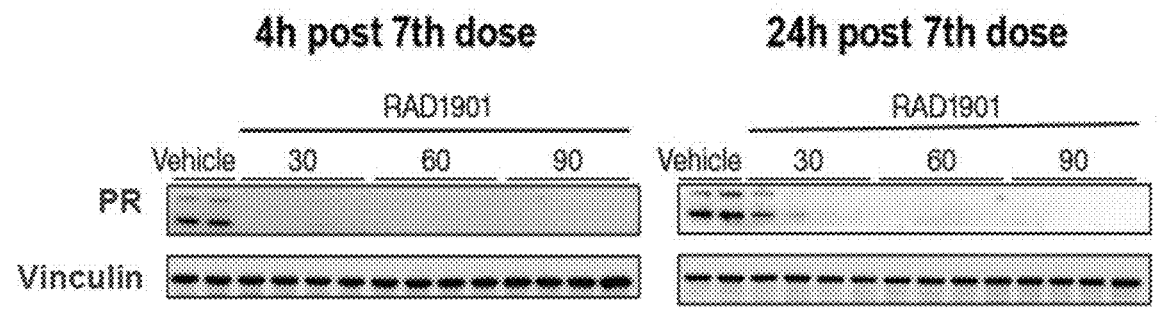
Figure 14C:
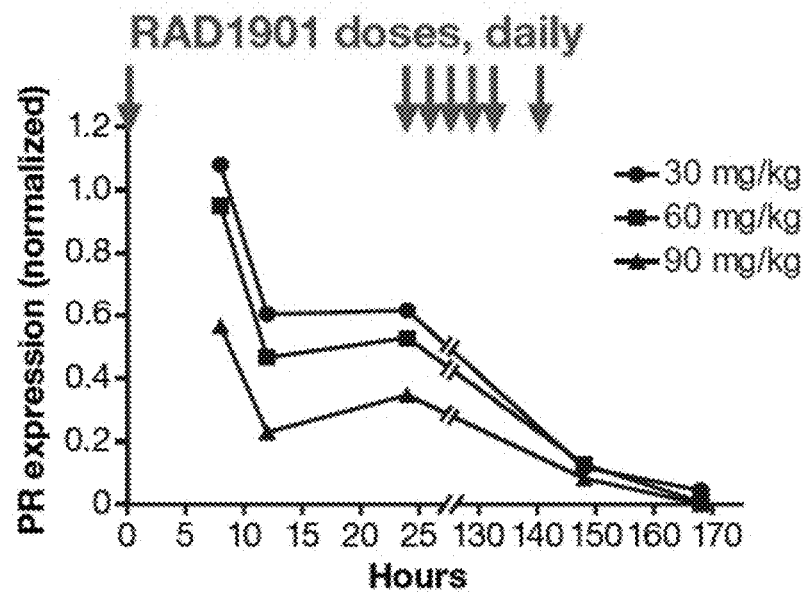

FIGS. 14A-C: RAD1901 treatment resulted in a rapid decrease in PR in MCF-7 xenograft models. (A): Western blot showing PR expression in MCF-7 xenograft models treated with vehicle control and RAD1901 at 30, 60, and 90 mg/kg, at 8 hours or 12 hours after single dose; (B): Western blot showing PR expression in MCF-7 xenograft models treated with vehicle control and RAD1901 at 30, 60, and 90 mg/kg, at 4 hours or 24 hours after the 7th dose; (C): Dose-dependent decrease in PR expression in MCF-7 xenograft models treated with RAD1901 at 30, 60, and 90 mg/kg.

Figure 15A:
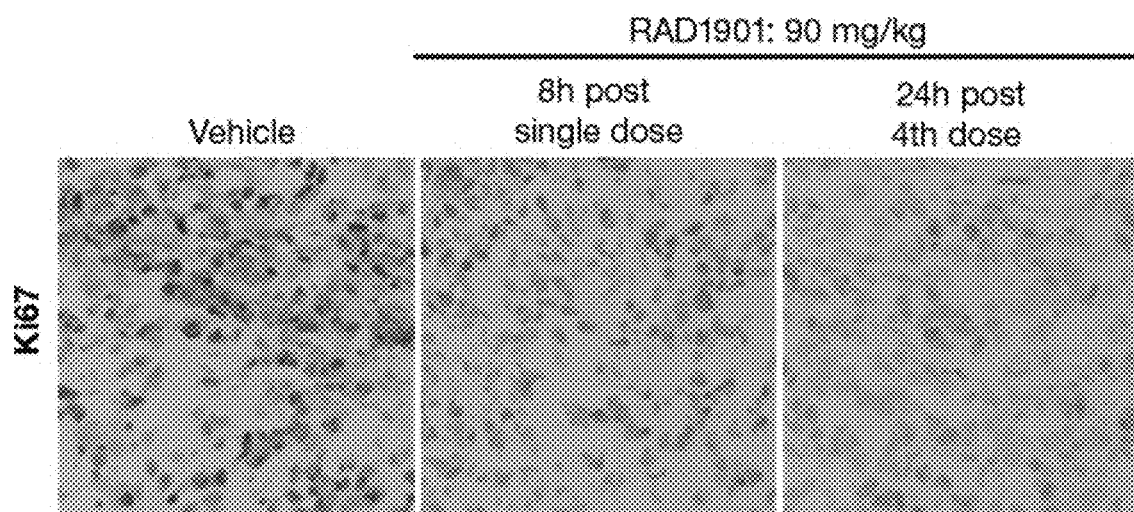
Figure 15B:
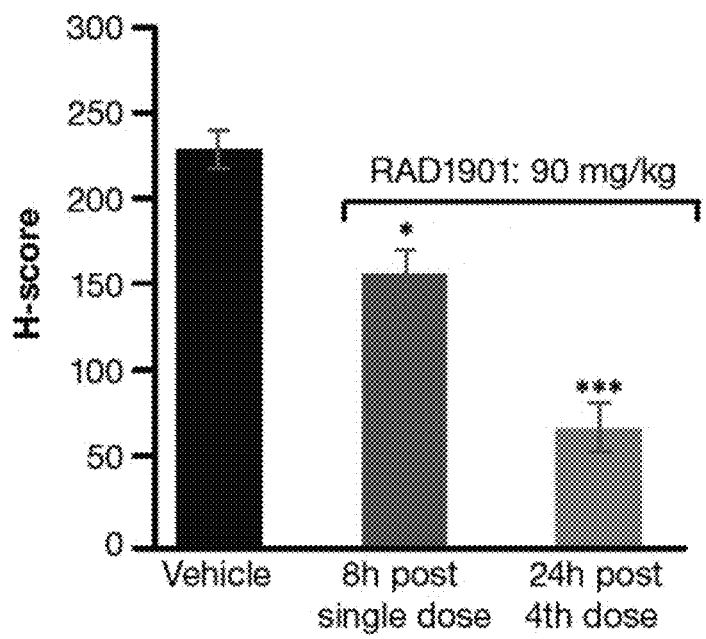

FIGS. 15A-B: RAD1901 treatment resulted in a rapid decrease in proliferation in MCF-7 xenograft models. (A): A representative photograph of a sectioned tumor harvested from MCF-7 xenograft models treated with vehicle control and RAD1901 at 90 mg/kg, 8 hours after single dose and 24 hours after the 4th dose, stained for proliferation marker Ki-67; (B): Histogram showing decrease of proliferation marker Ki-67 in MCF-7 xenograft models treated with vehicle control and RAD1901 at 90 mg/kg, 8 hours after single dose and 24 hours after the 4th dose.

Figure 16:
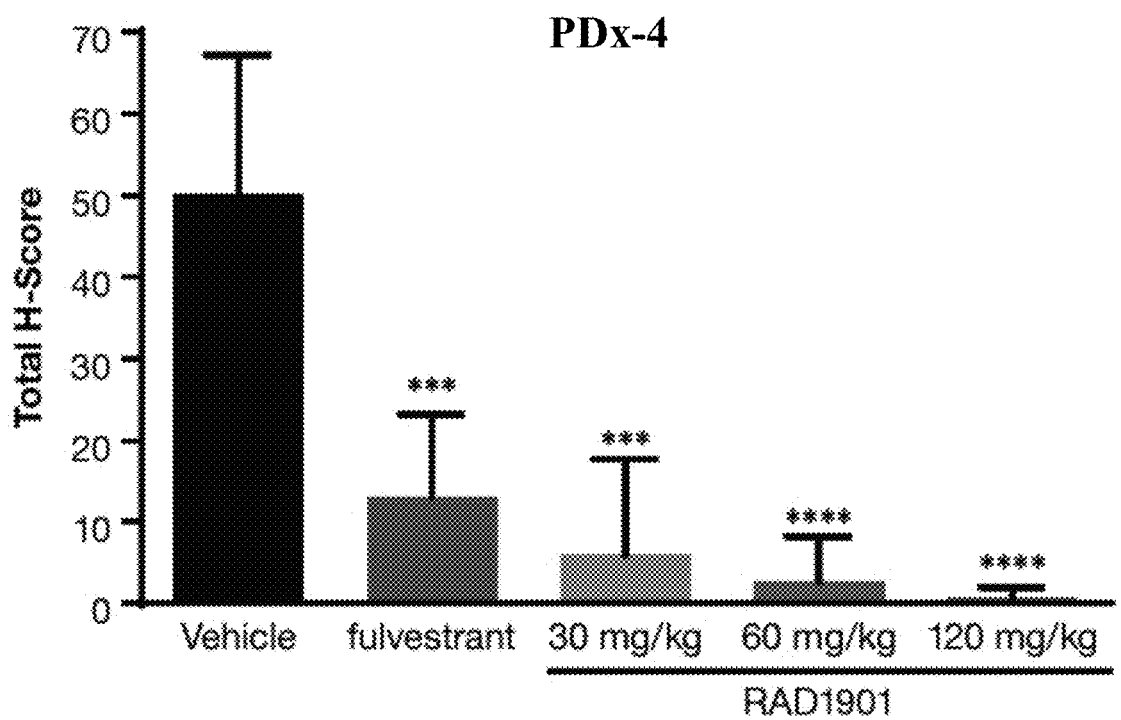

FIG. 16: RAD1901 treatment at 30, 60, and 120 mg/kg decreased Ki67 more significantly than fulvestrant (1 mg/animal) in end of study tumors of PDx-4 models four hours on the last day of a 56 day efficacy study.

Figure 17:
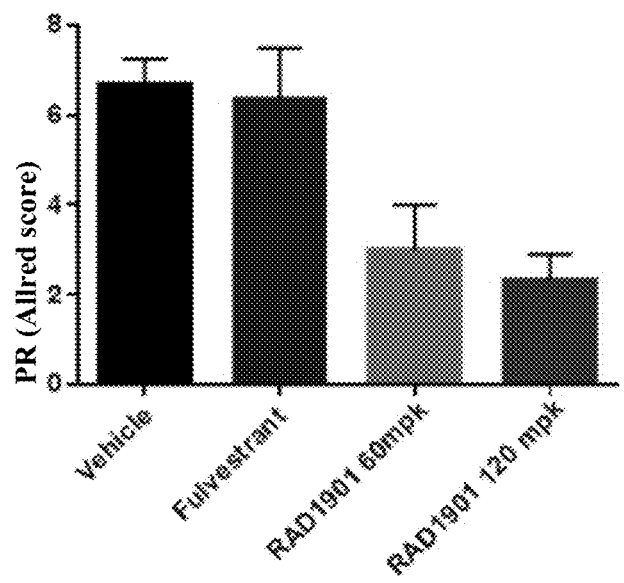

FIG. 17: RAD1901 treatment at 60 and 120 mg/kg resulted in reduced ER signaling in vivo in PDx-5 models with decreased PR expression.

FIGS. 18A-D: Effect of RAD1901 on uterine tissue in newly weaned female Sprague-Dawley rats. (A): Uterine wet weights of rats euthanized 24 hours after the final dose; (B): Epithelial height in tissue sections of the uterus; (C): Representative sections of Toluidine Blue O-stained uterine tissue at 400× magnification, arrows indicate uterine epithelium; (D): Total RNA extracted from uterine tissue and analyzed by quantitative RT-PCR for the level of complement C3 expression relative to the 18S ribosomal RNA housekeeping gene.

Figure 19:
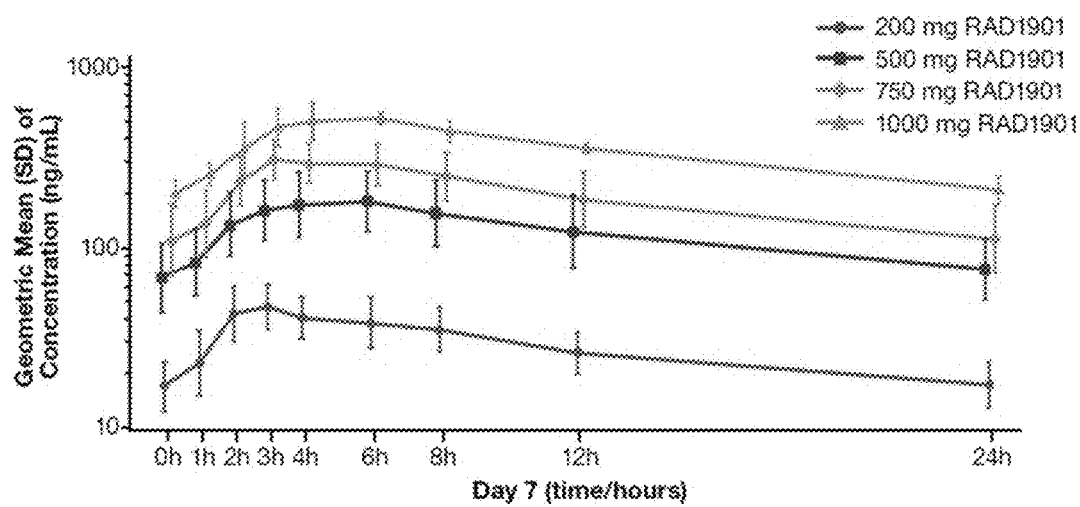

FIG. 19: Plasma pharmacokinetic results of RAD1901 at 200, 500, 750, and 1000 mg/kg after dosing on Day 7.

Figure 20:
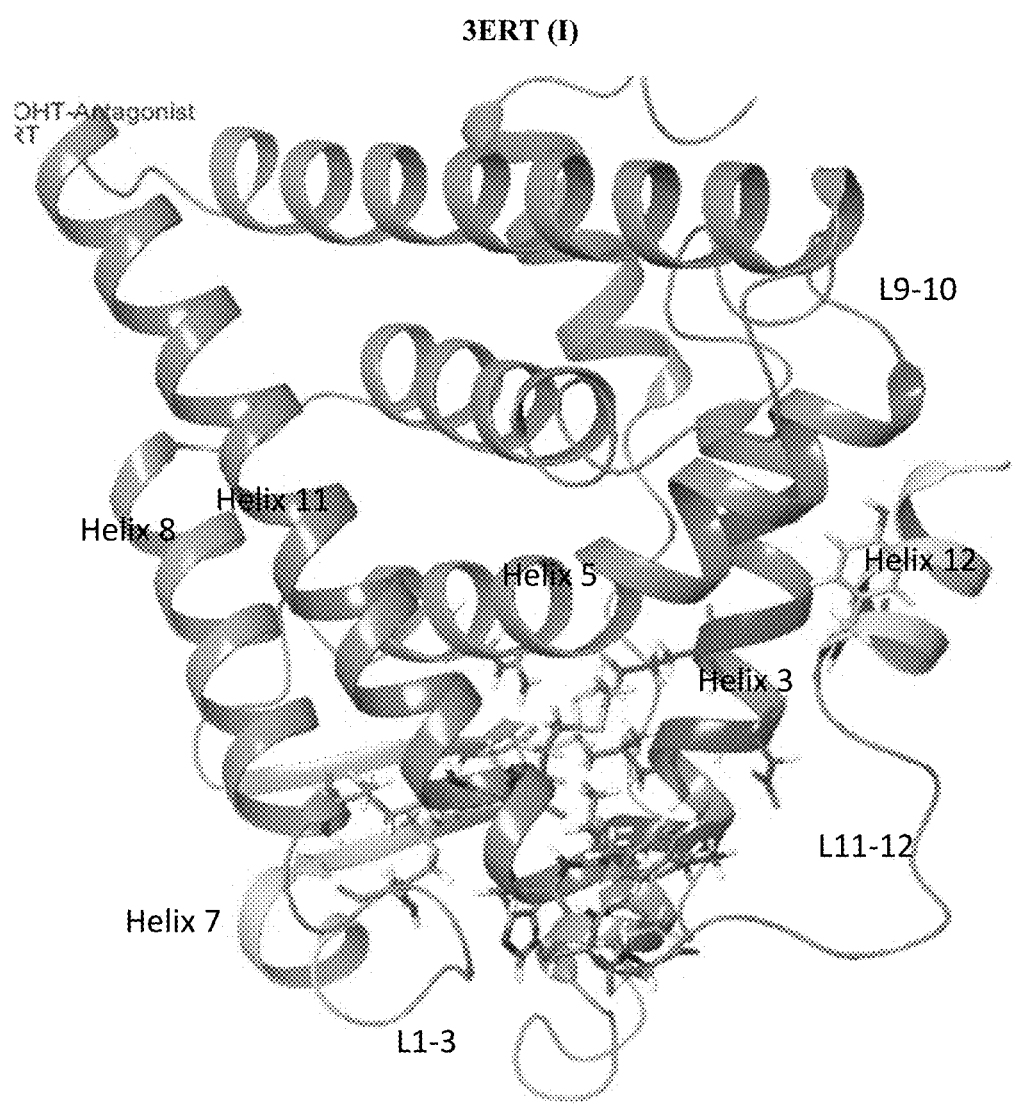
Figure 21:
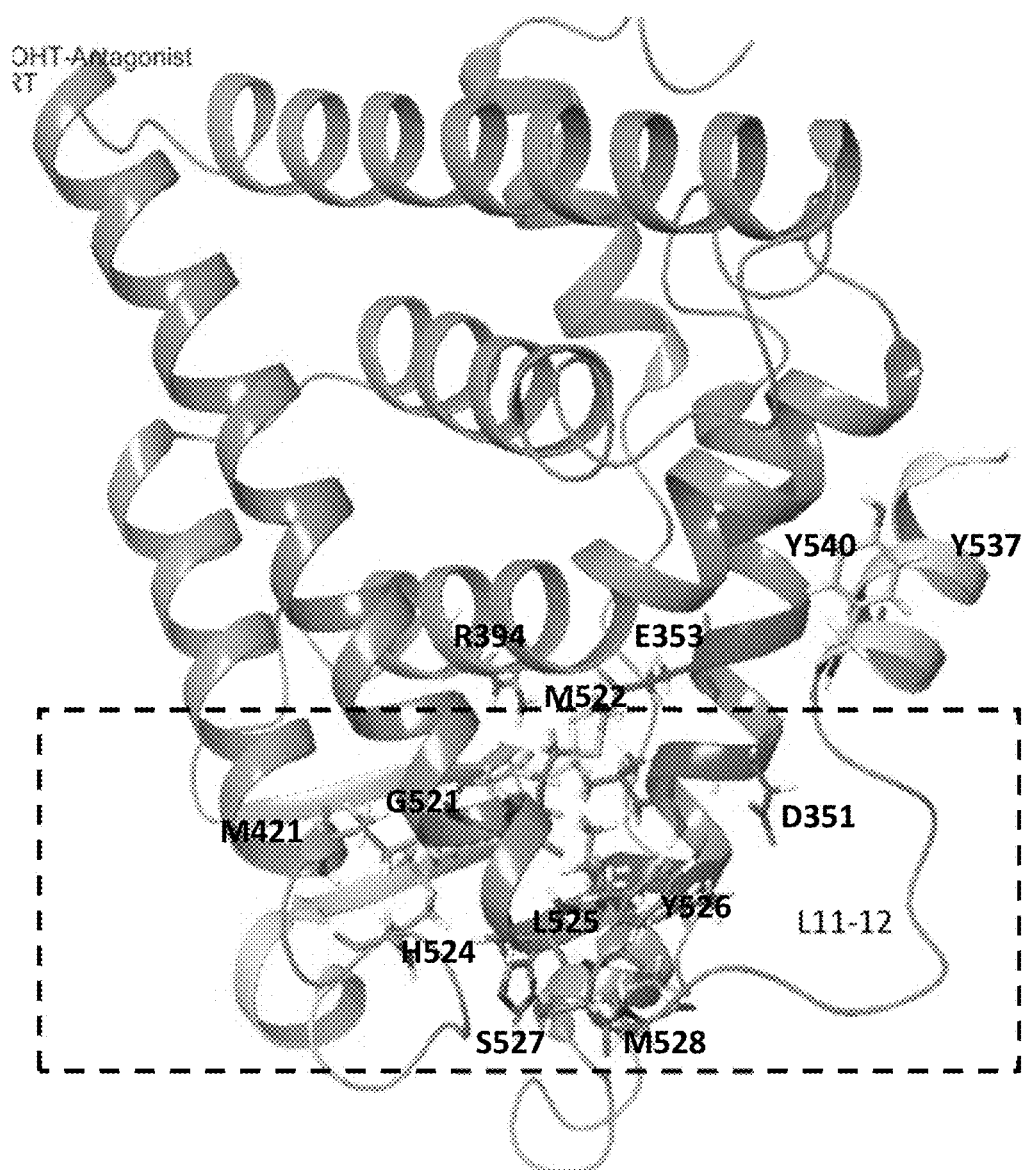
Figure 22:
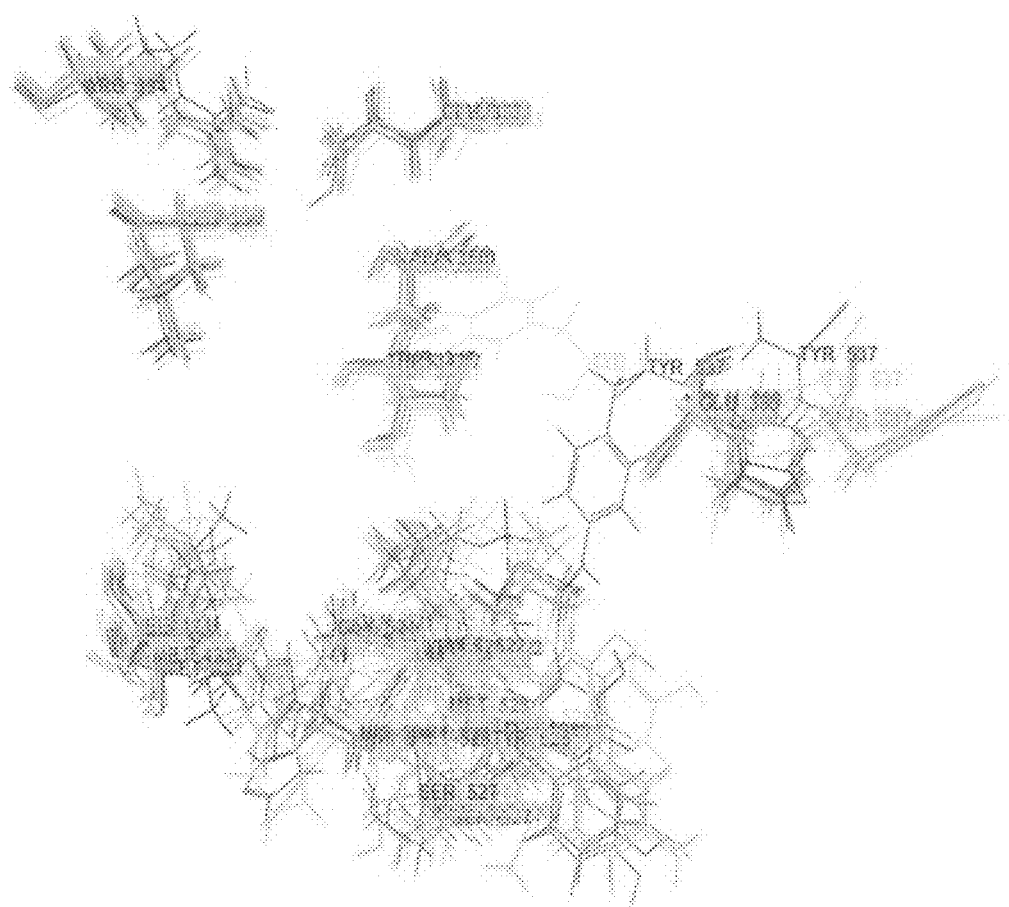
Figure 23A:
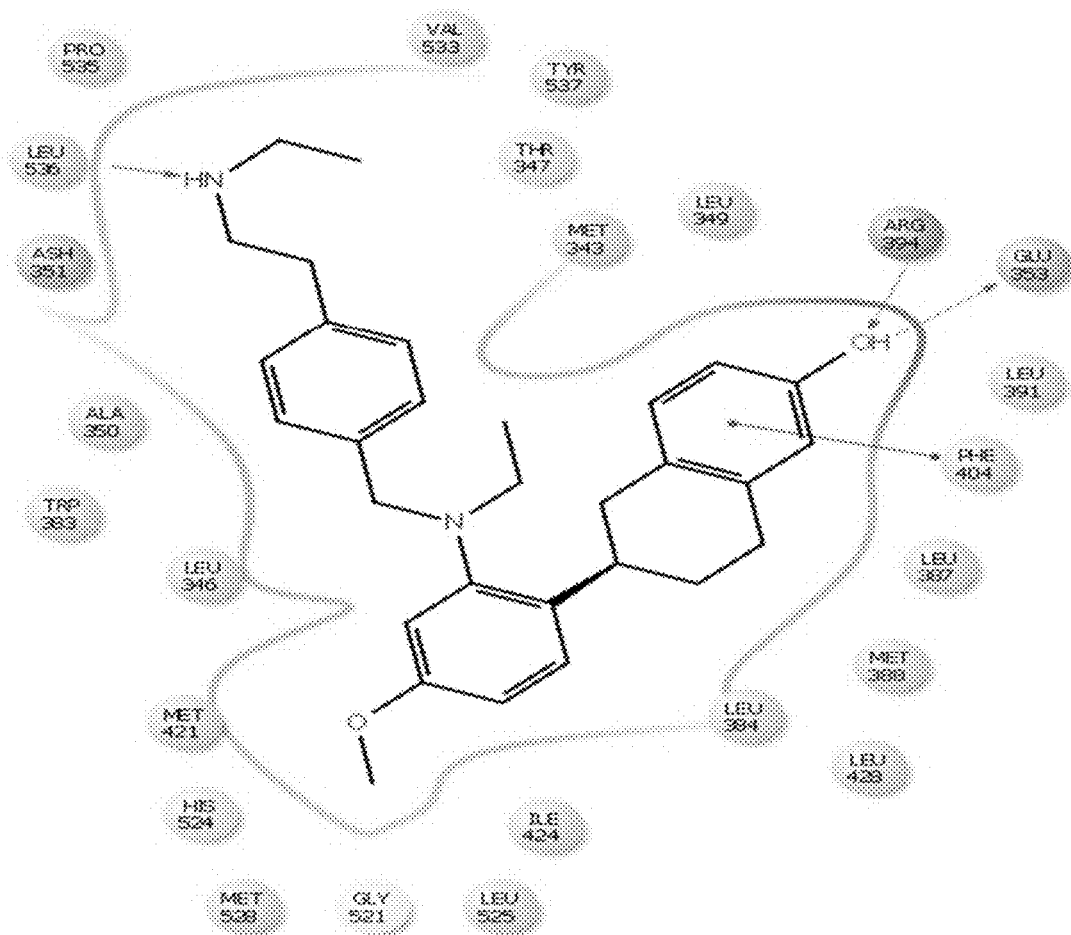
Figure 23B:
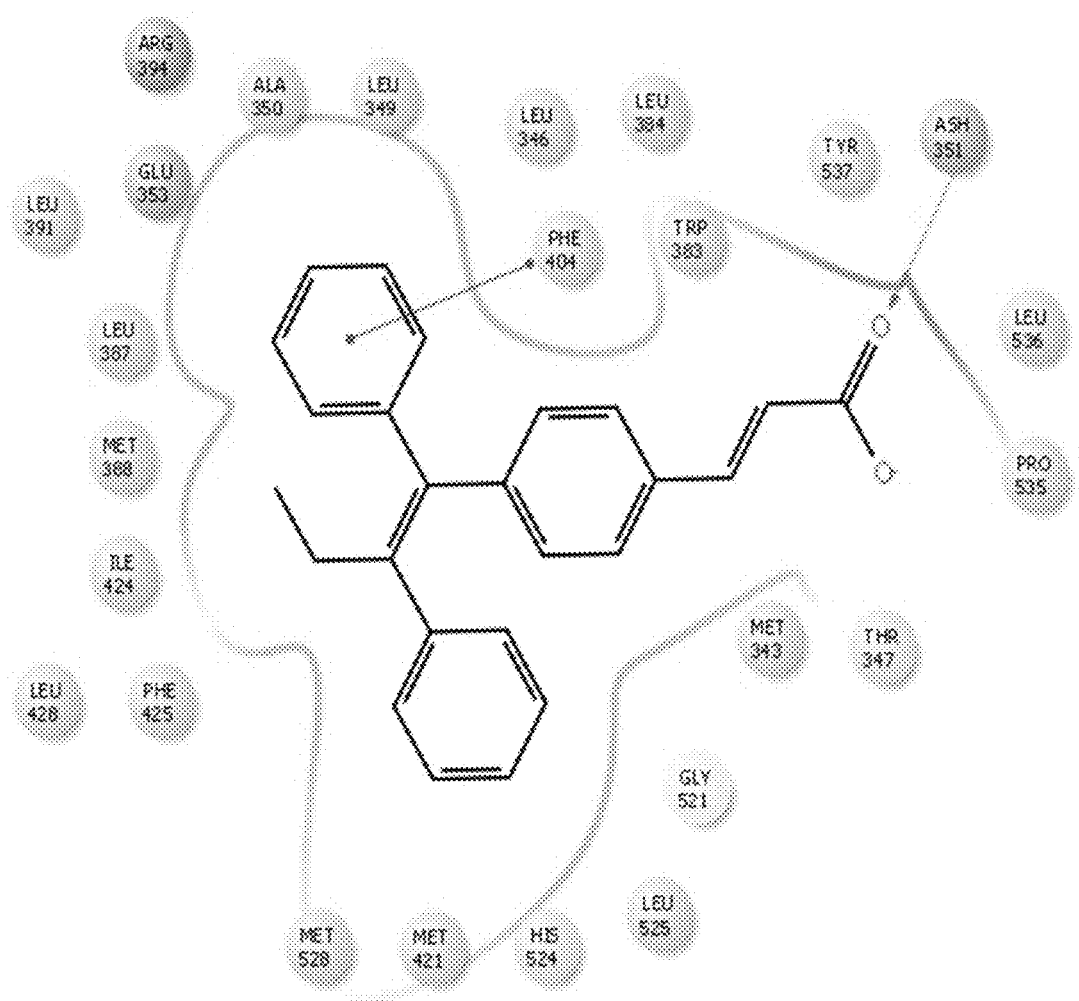
Figure 24A:
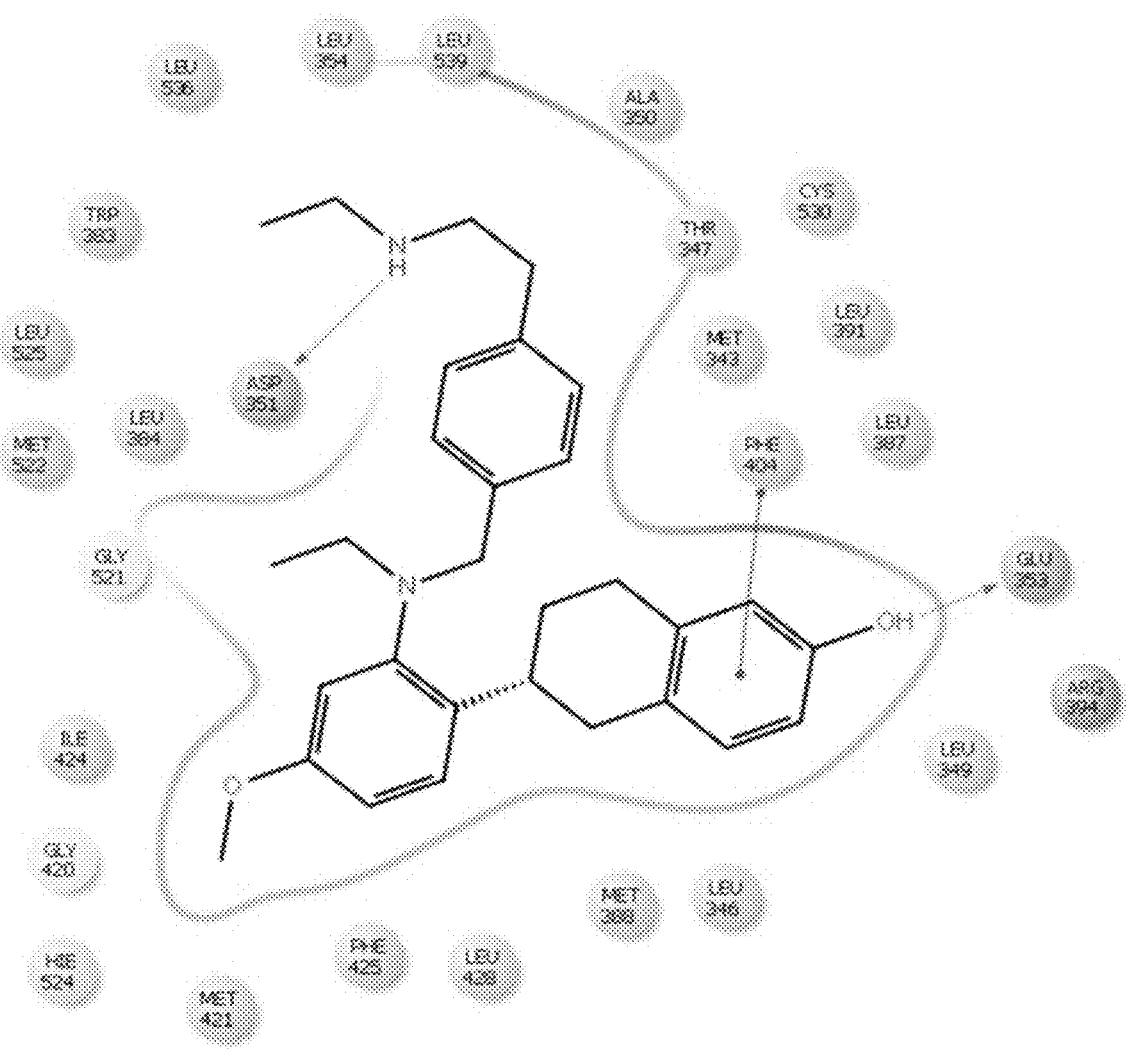
Figure 24B:
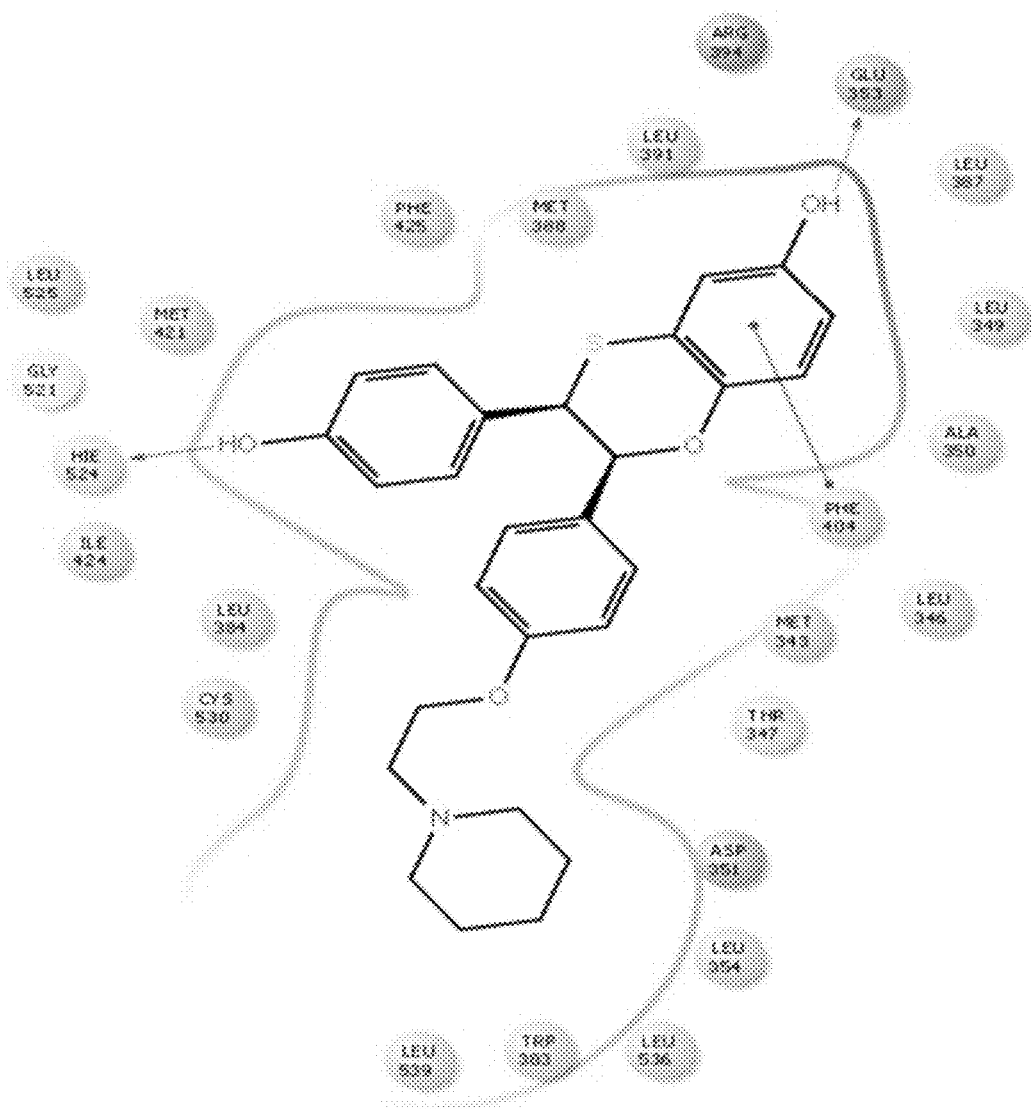
Figure 25A:
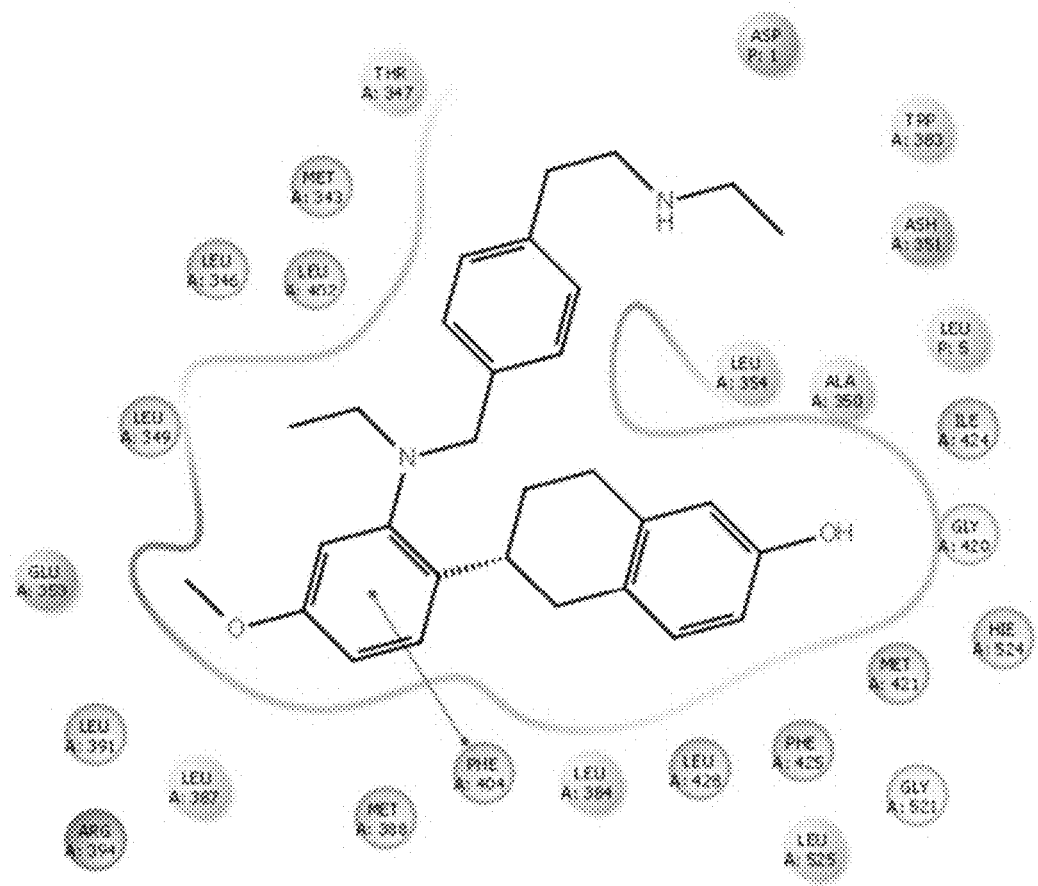
Figure 25B:
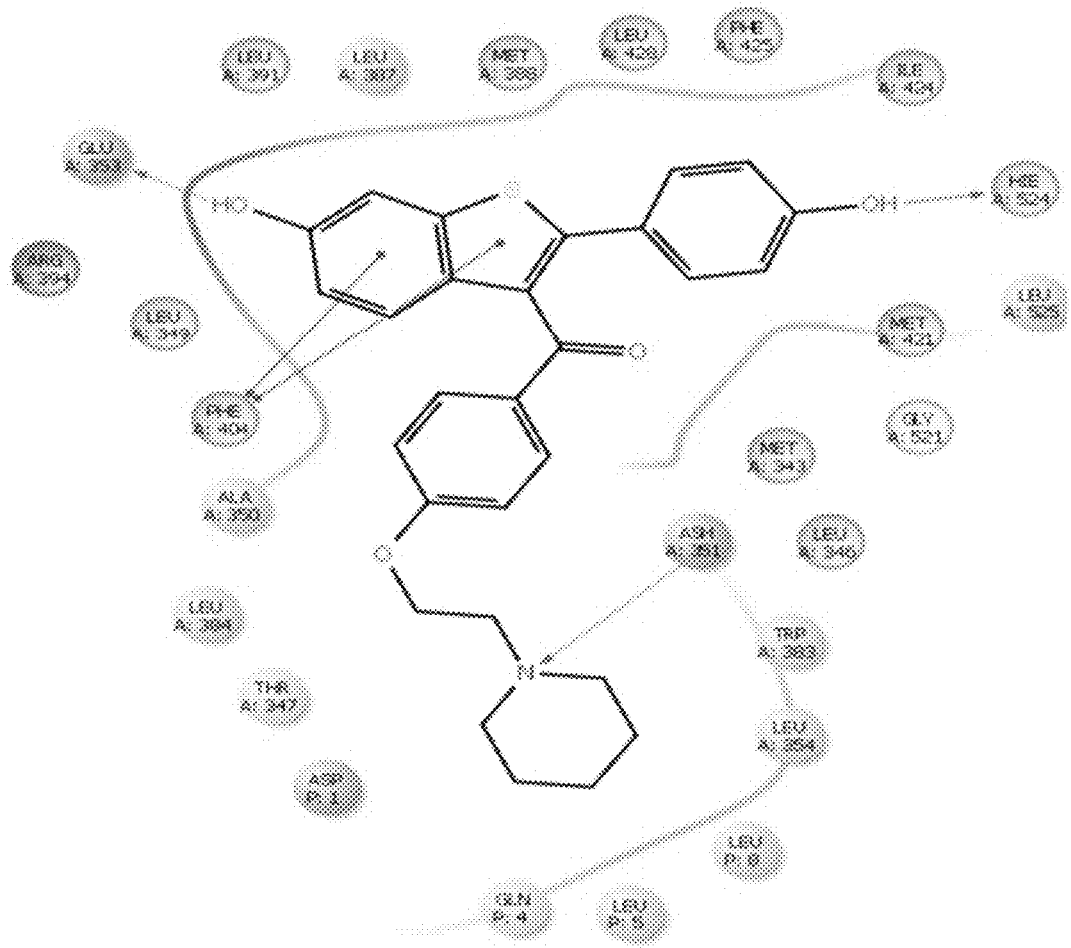
Figure 26A:
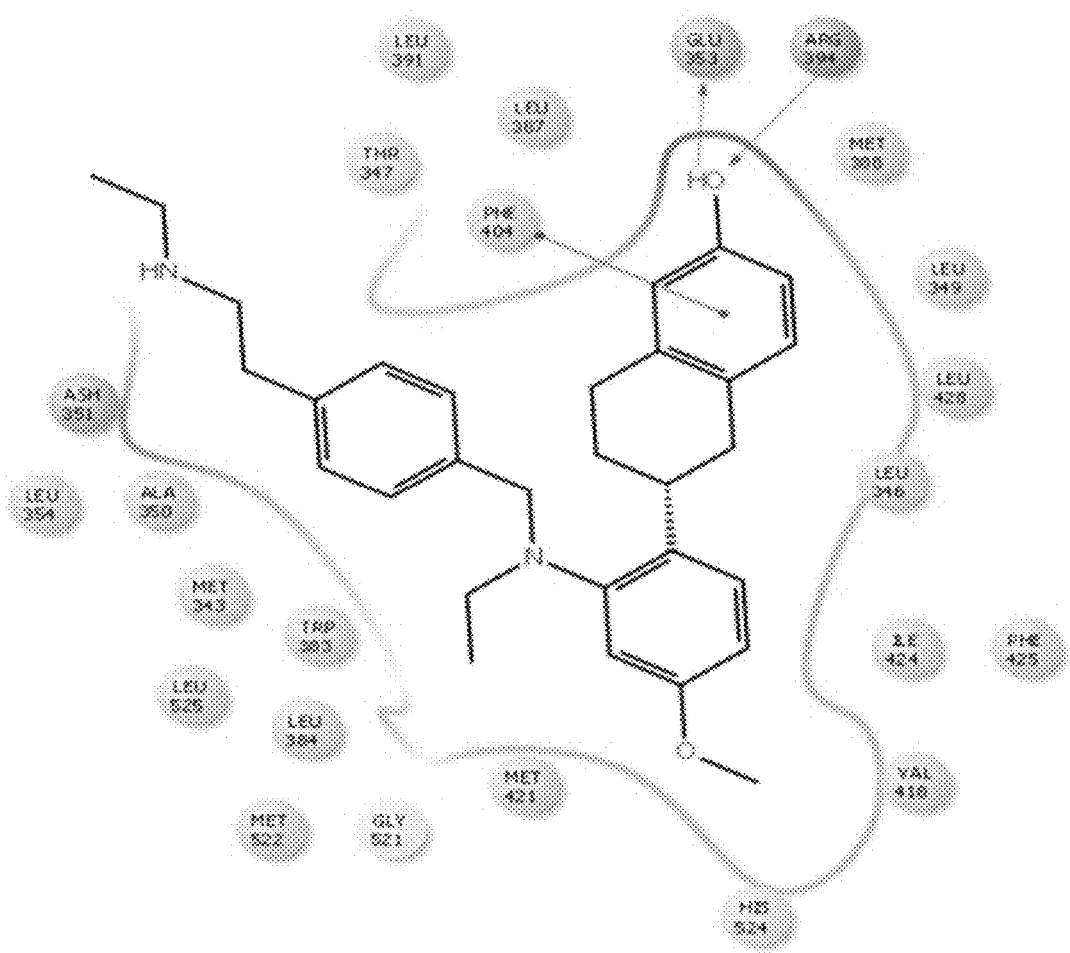
Figure 26B:
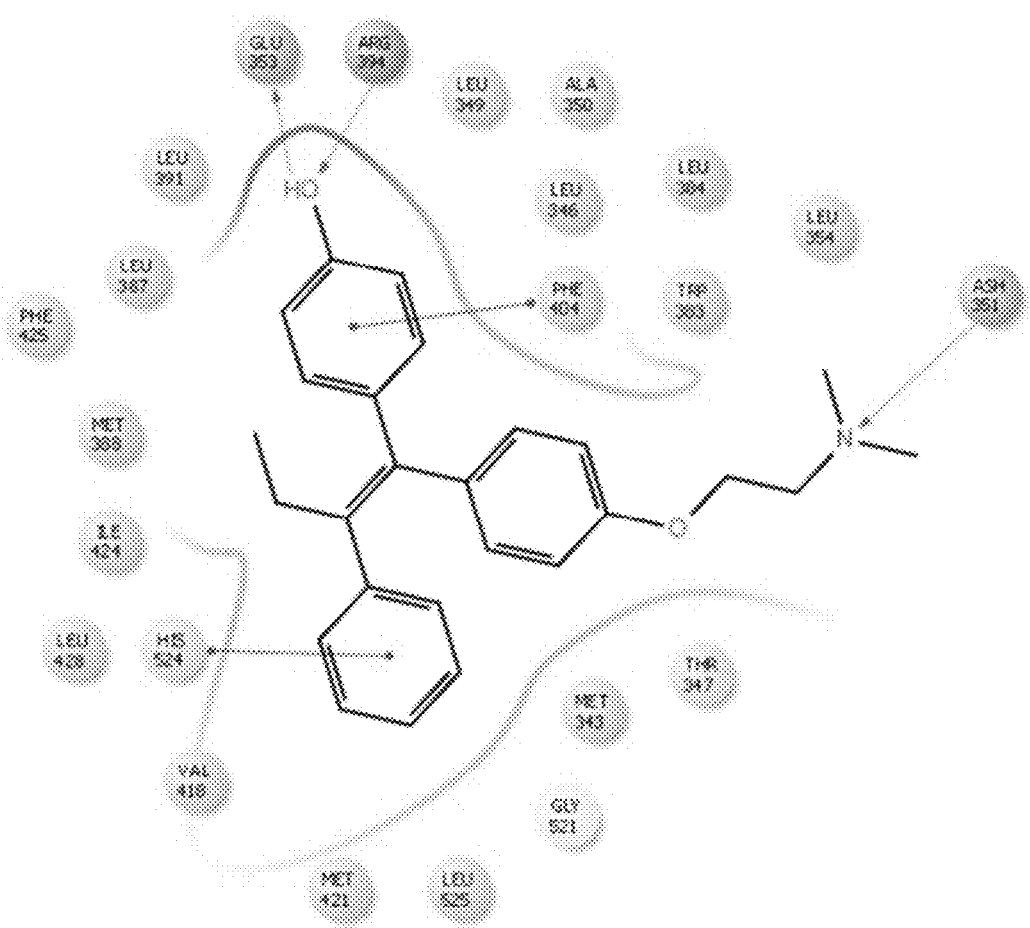
Figure 27A:
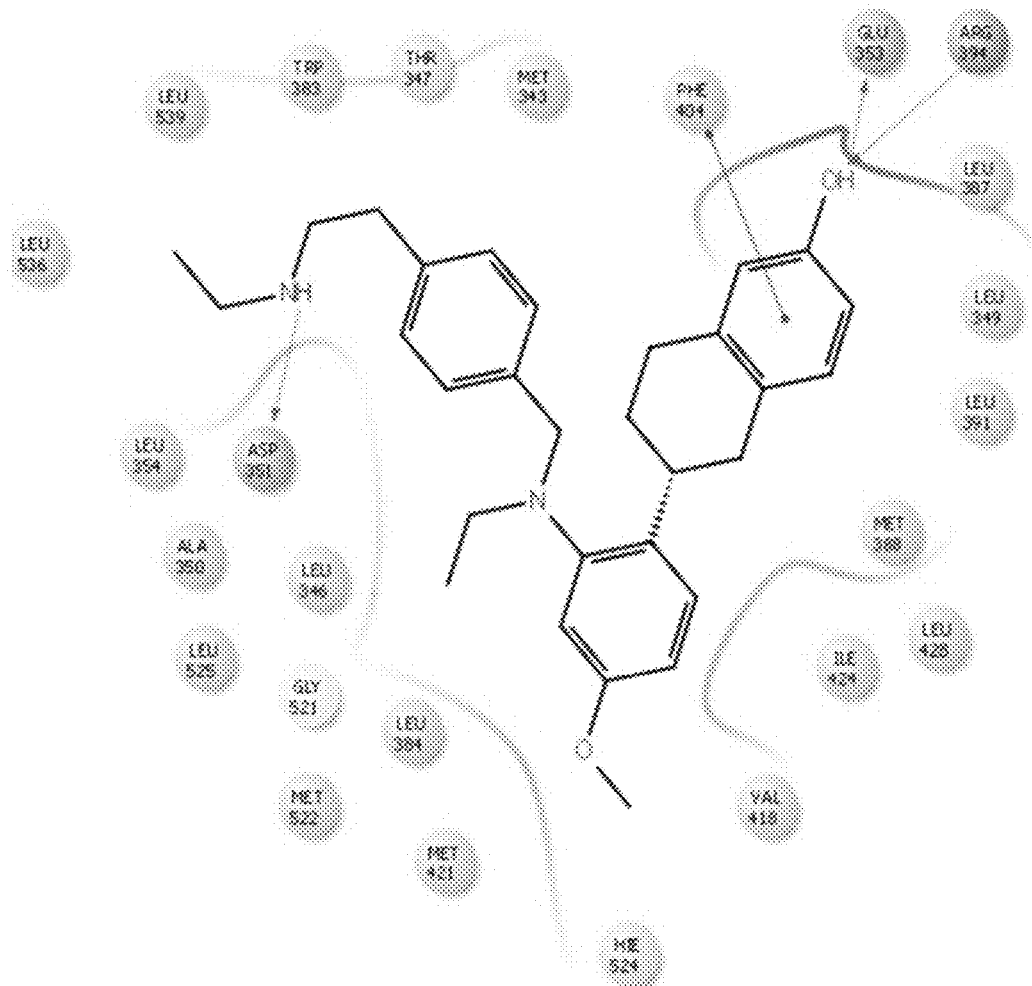
Figure 27B:
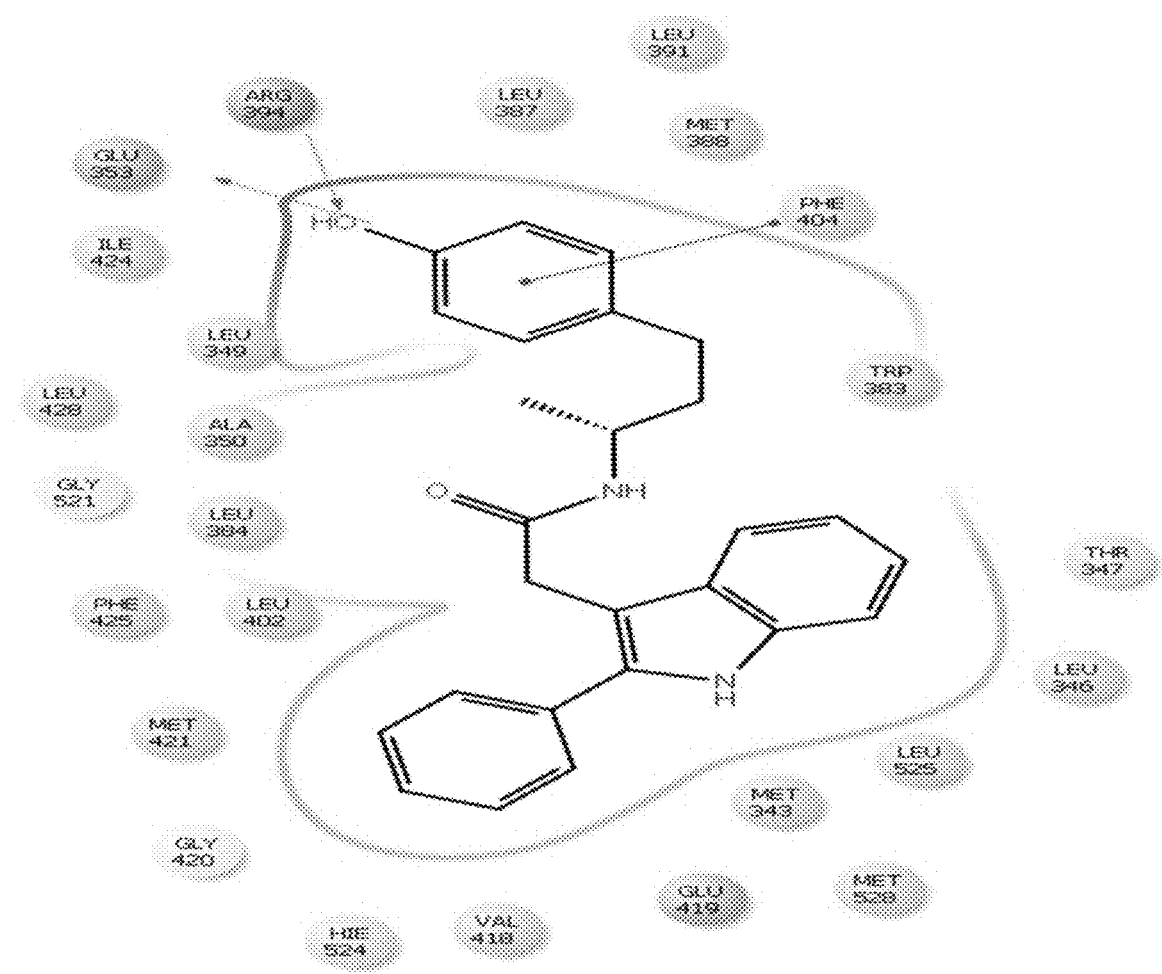
Figure 28:
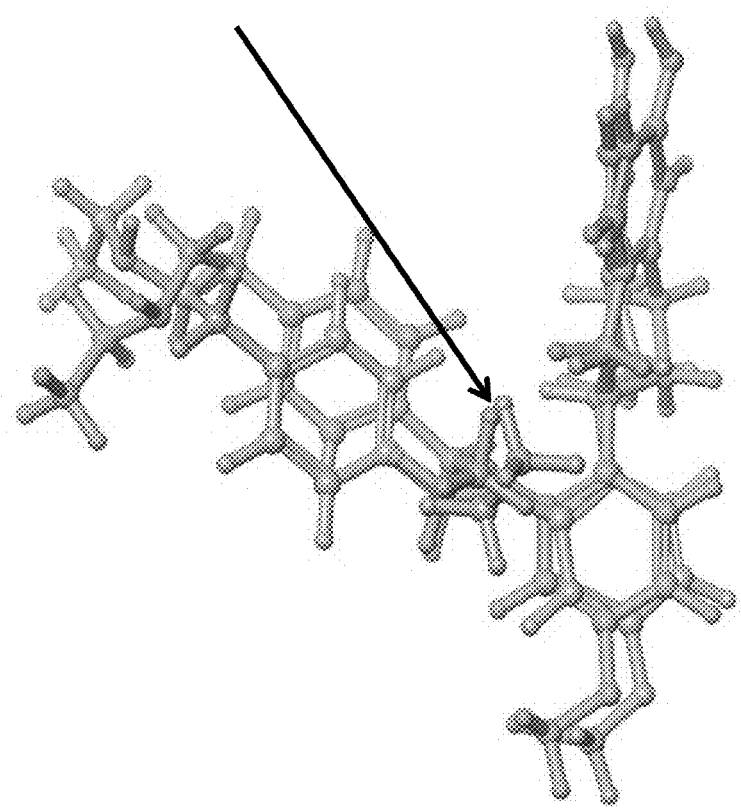
Figure 29:
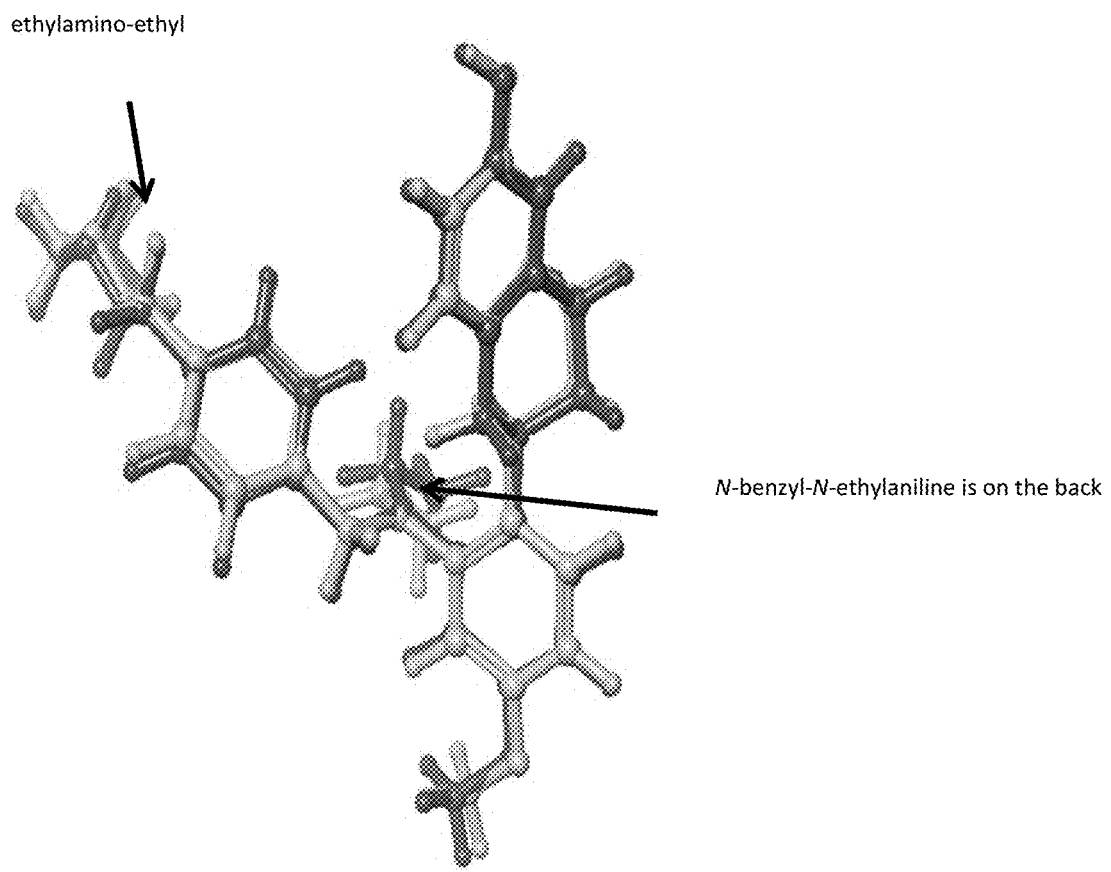
Figure 30A:
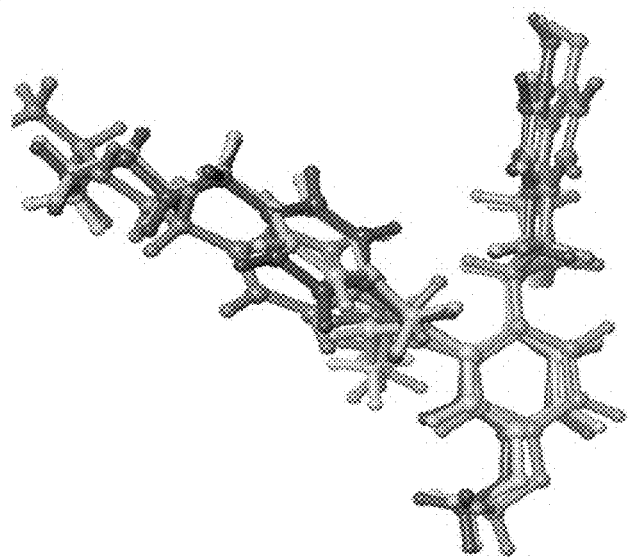
Figure 30B:
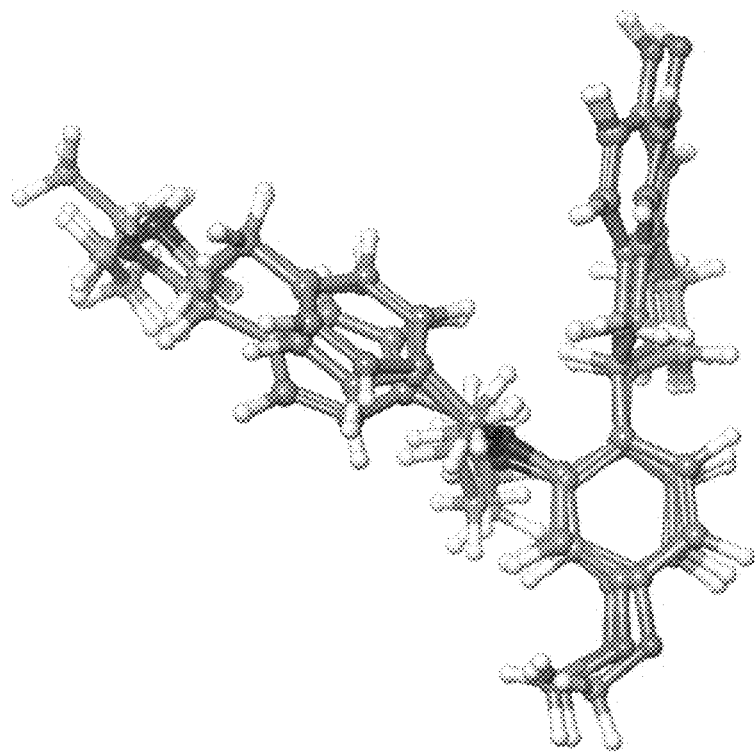
Figure 31A:
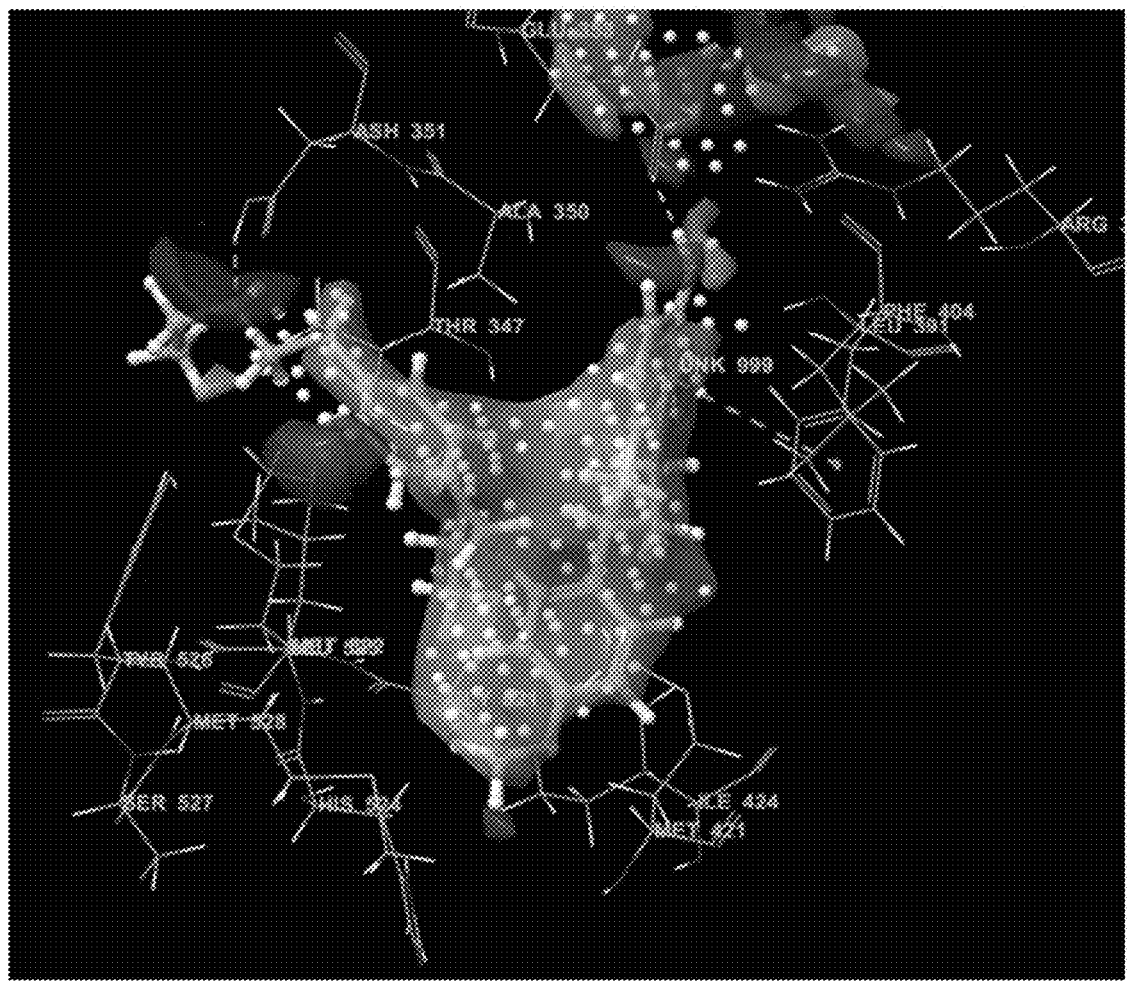
Figure 31B:
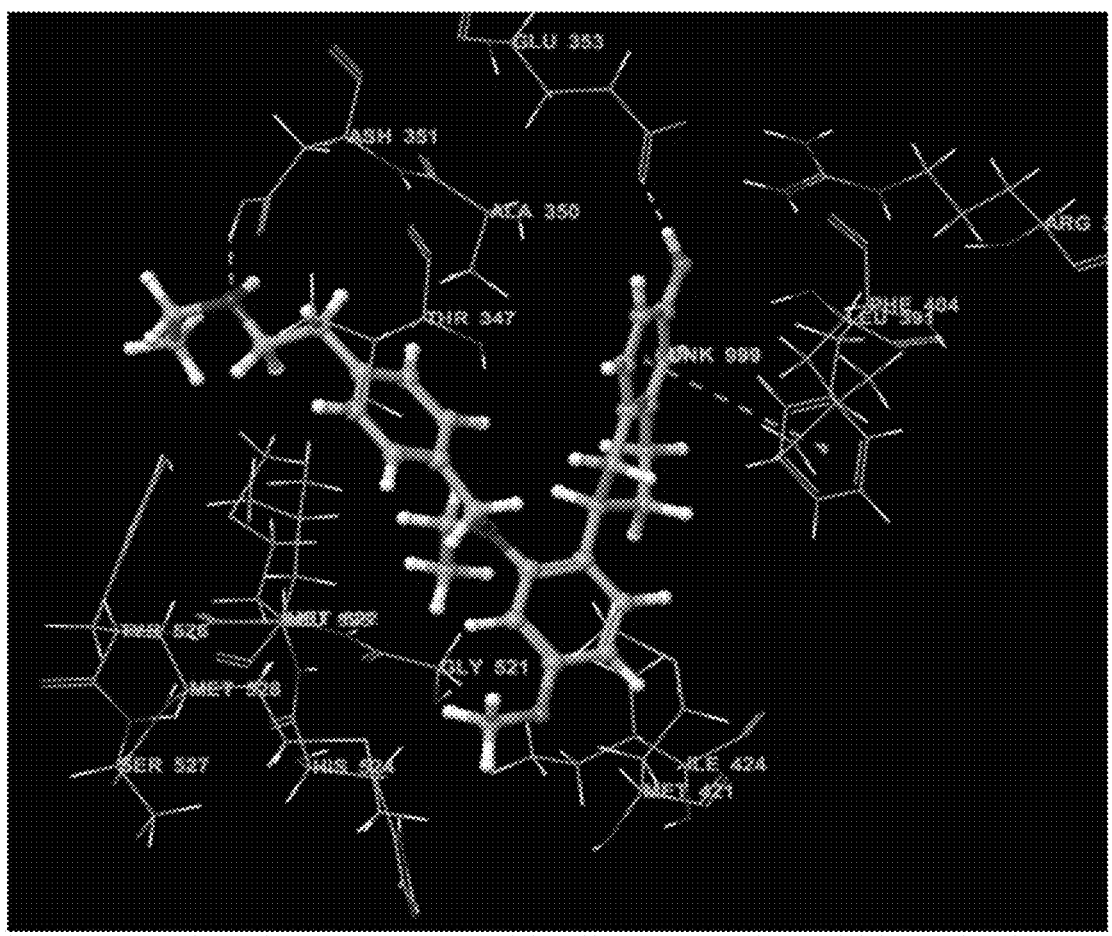
Figure 31C:
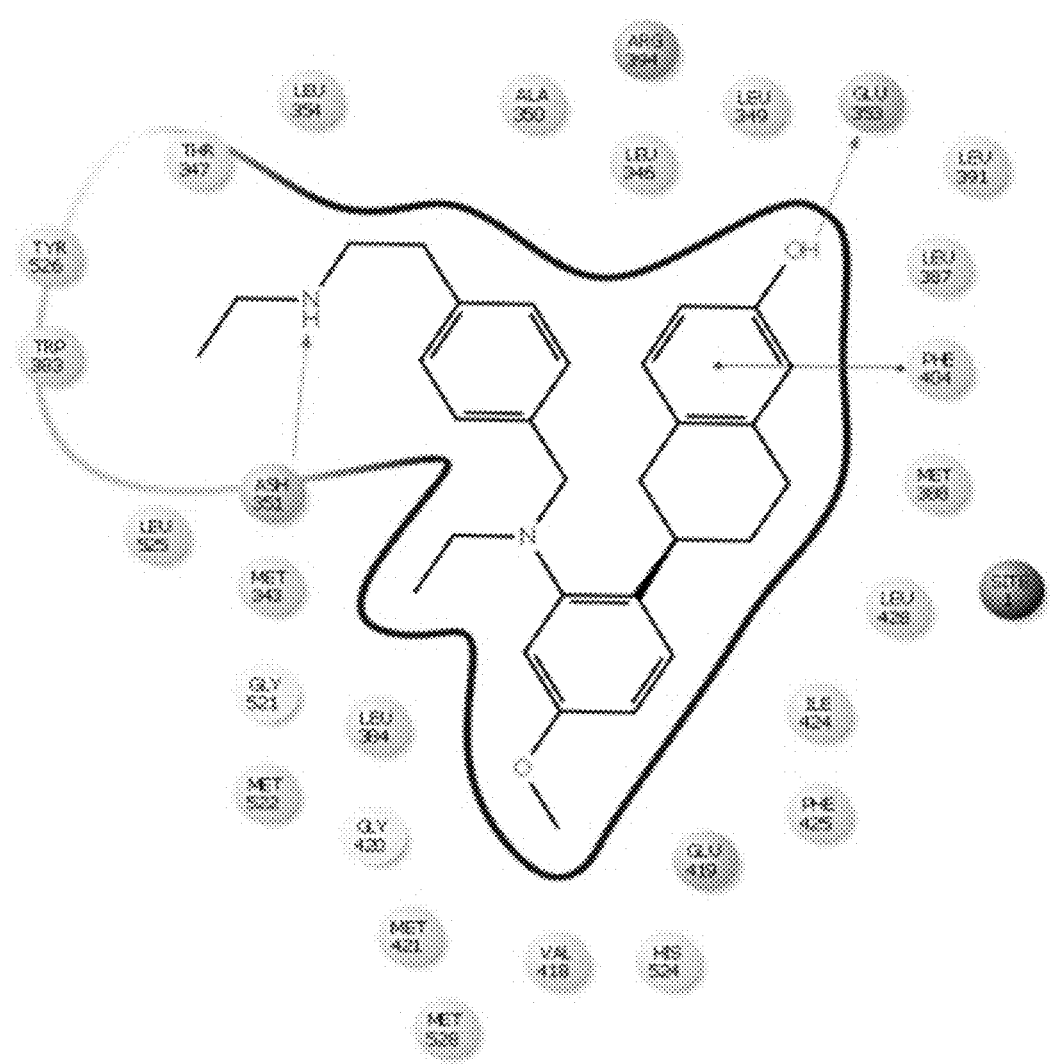
Figure 32A:
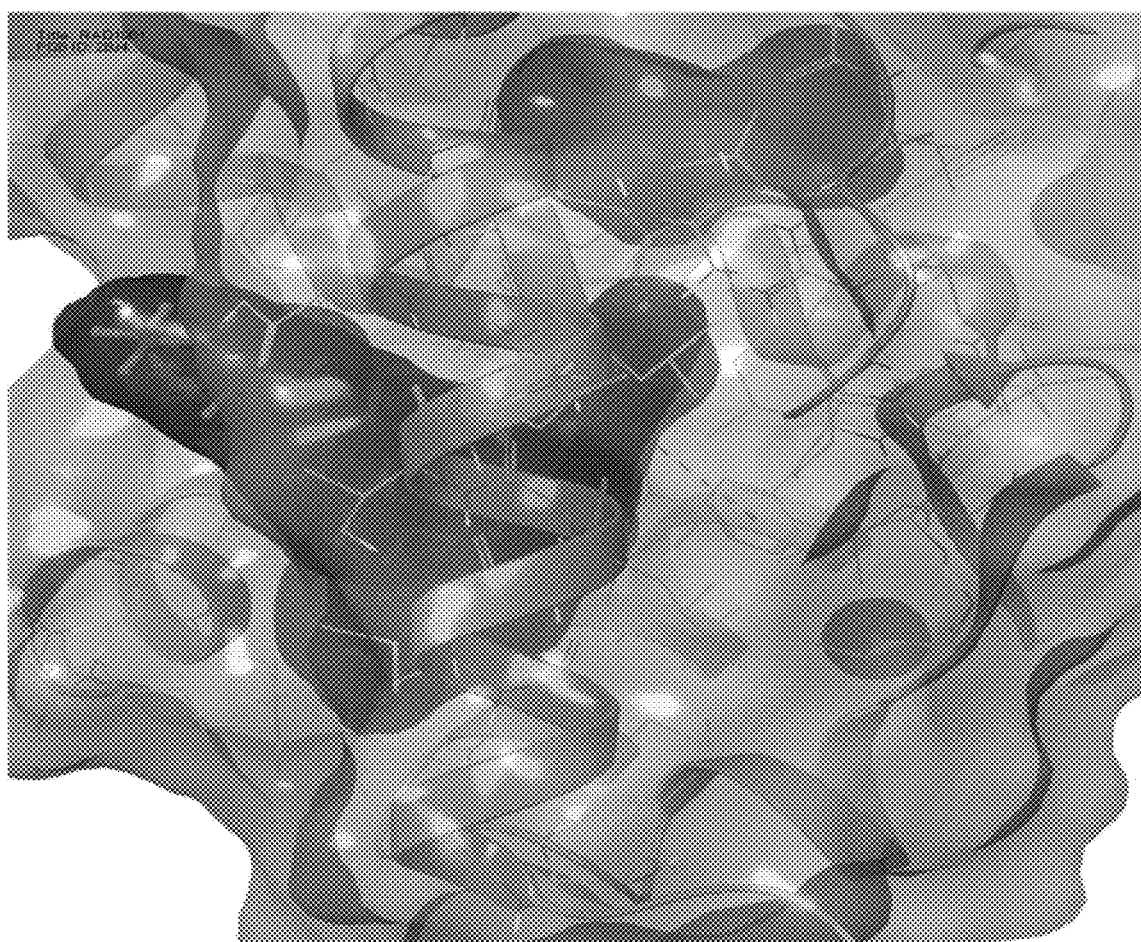
Figure 32B:
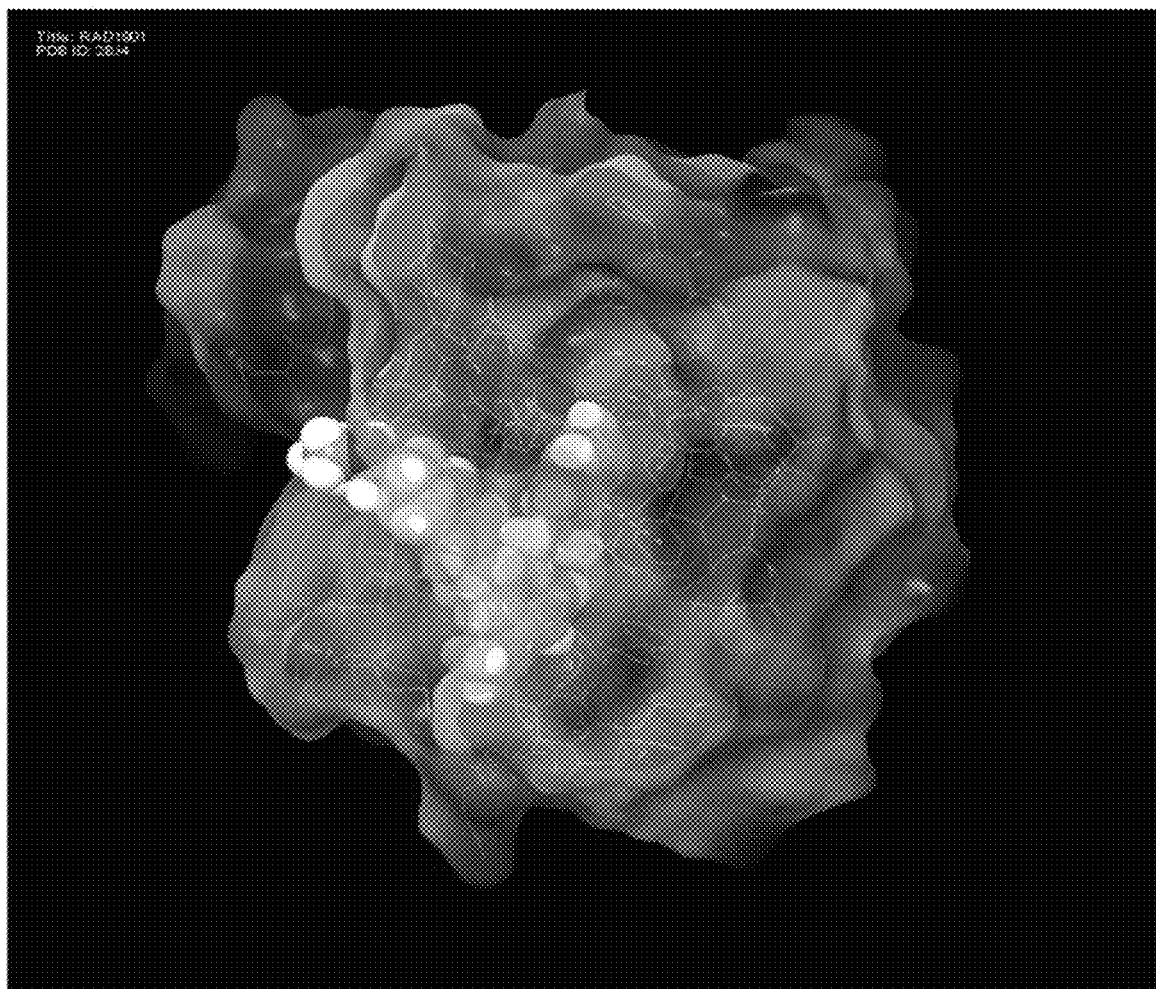
Figure 32C:
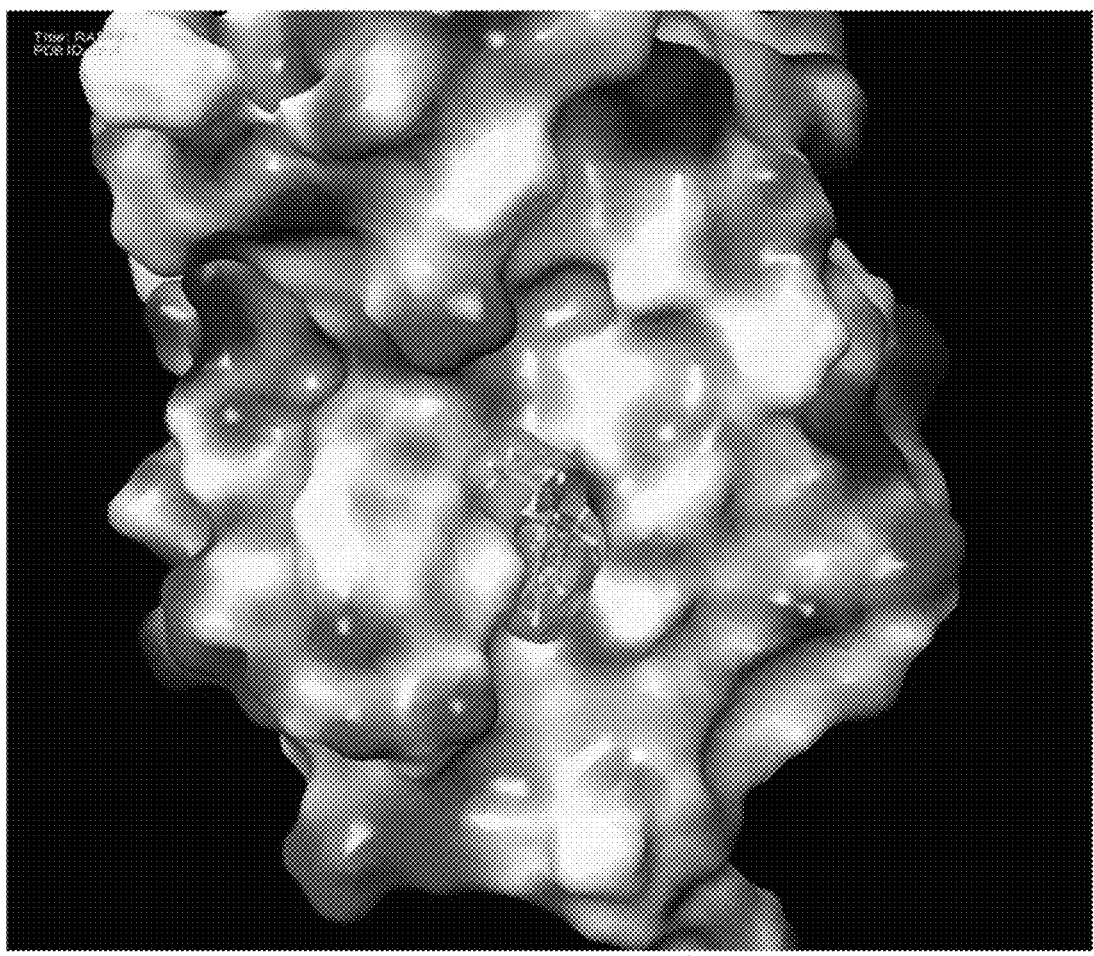
Figure 33A:
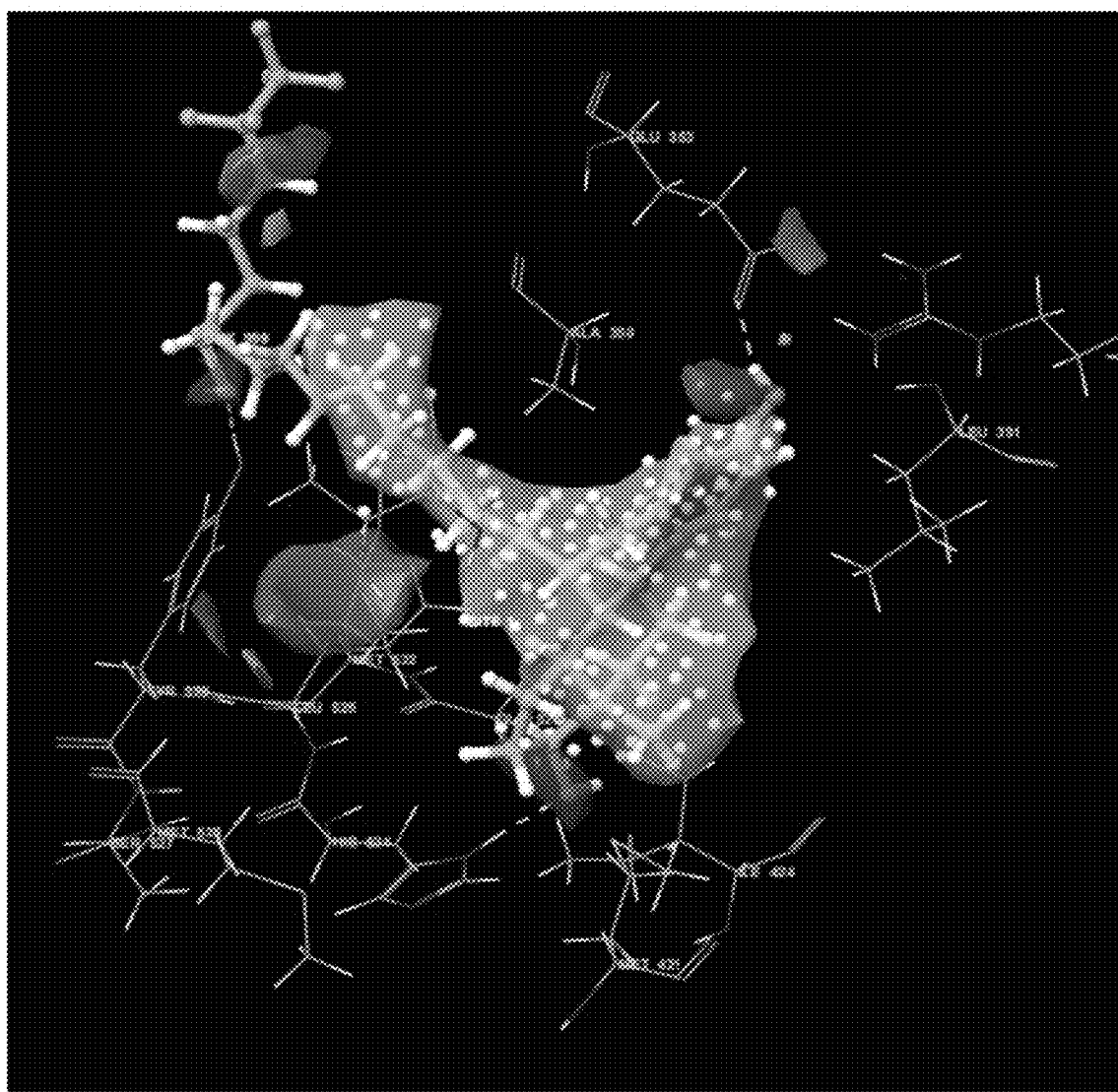
Figure 33B:
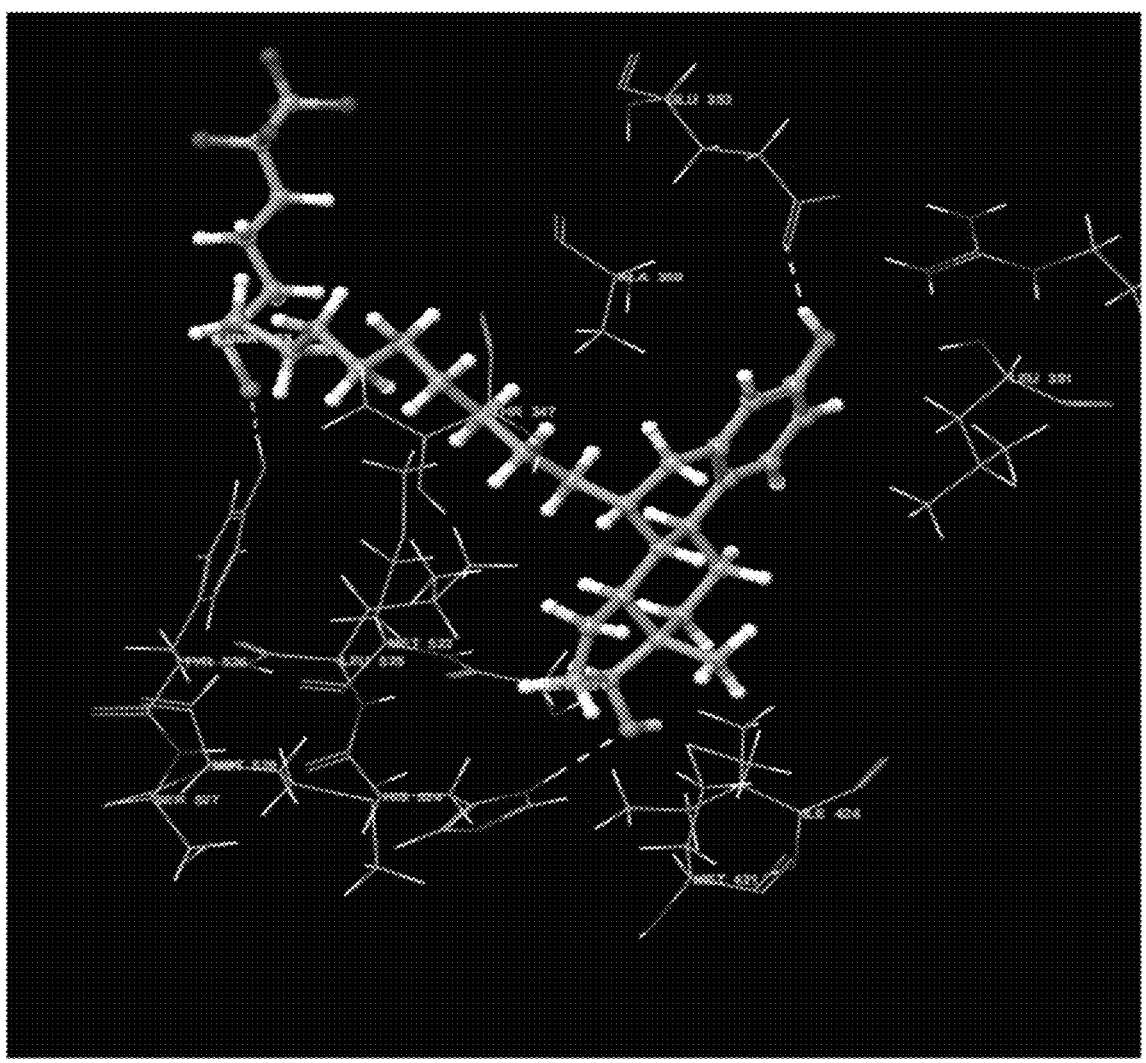
Figure 33C:
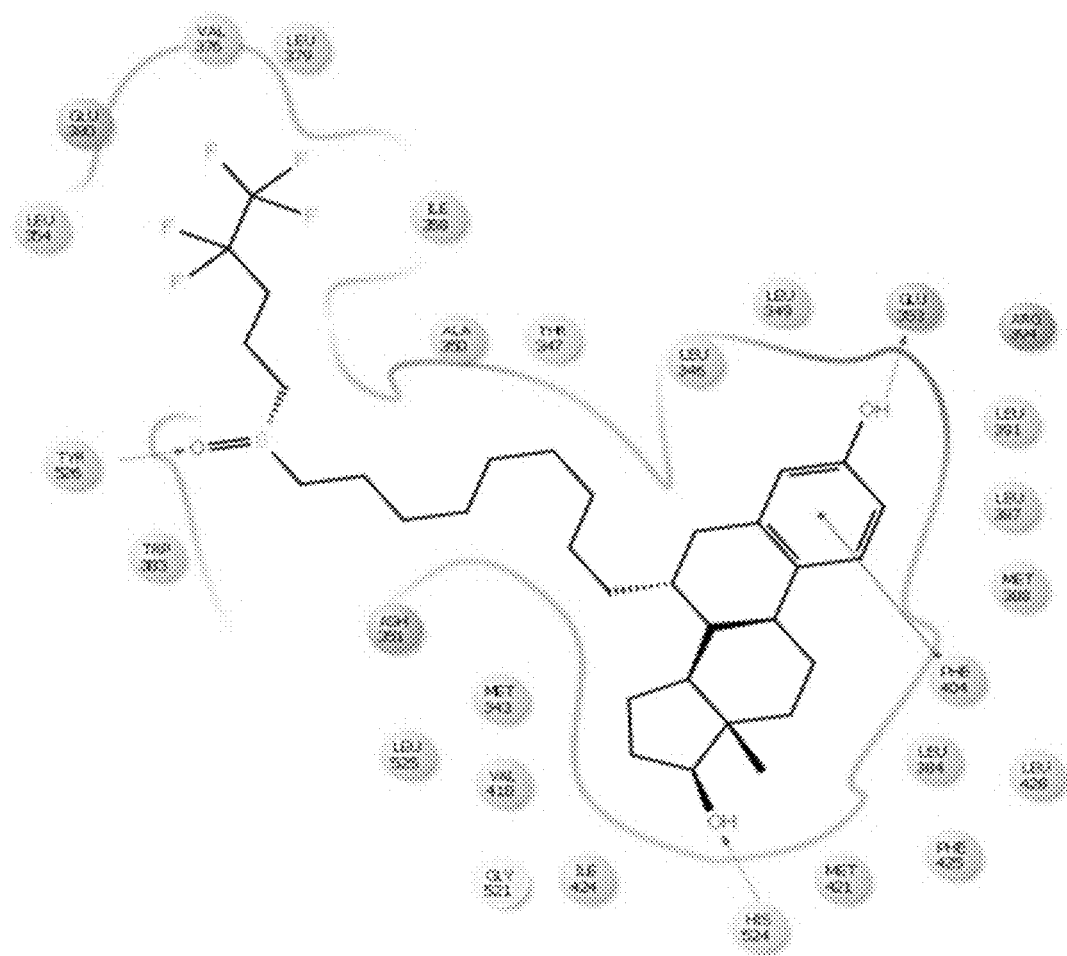
Figure 35A:
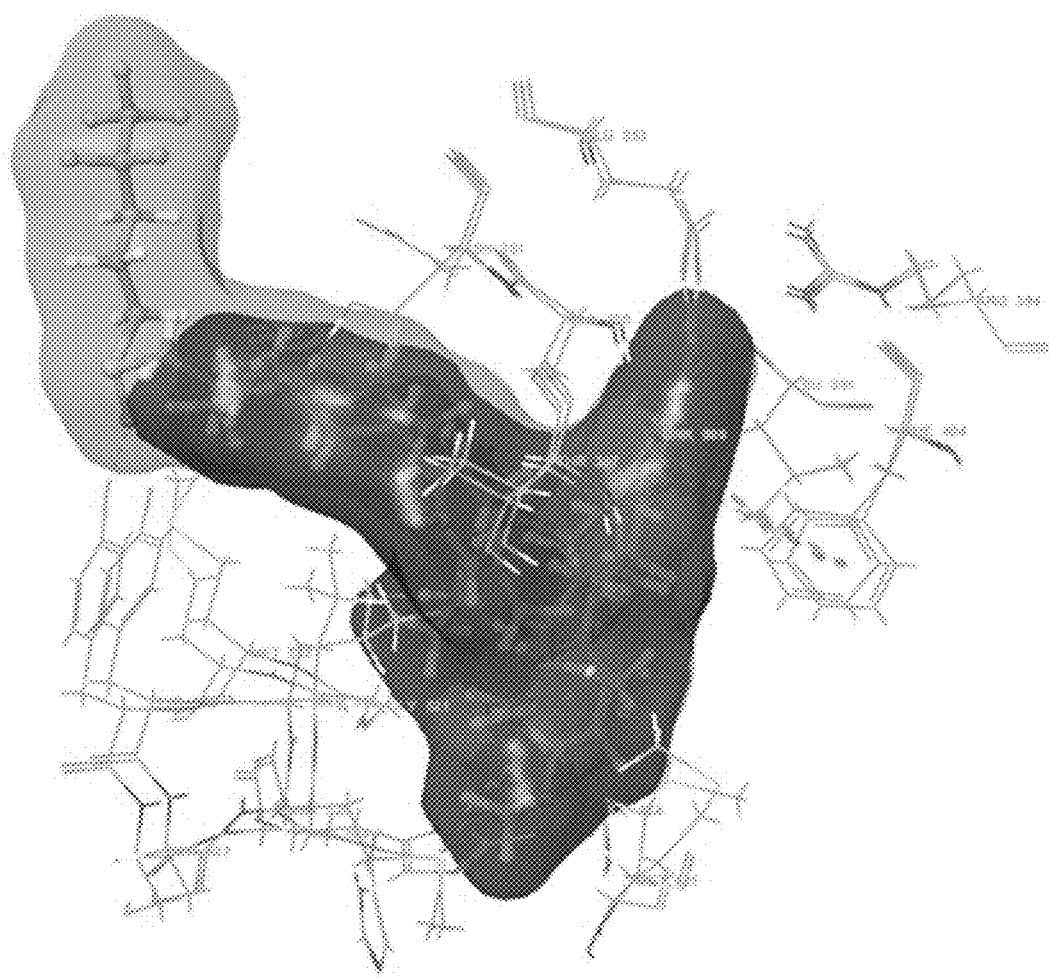
Figure 35B:
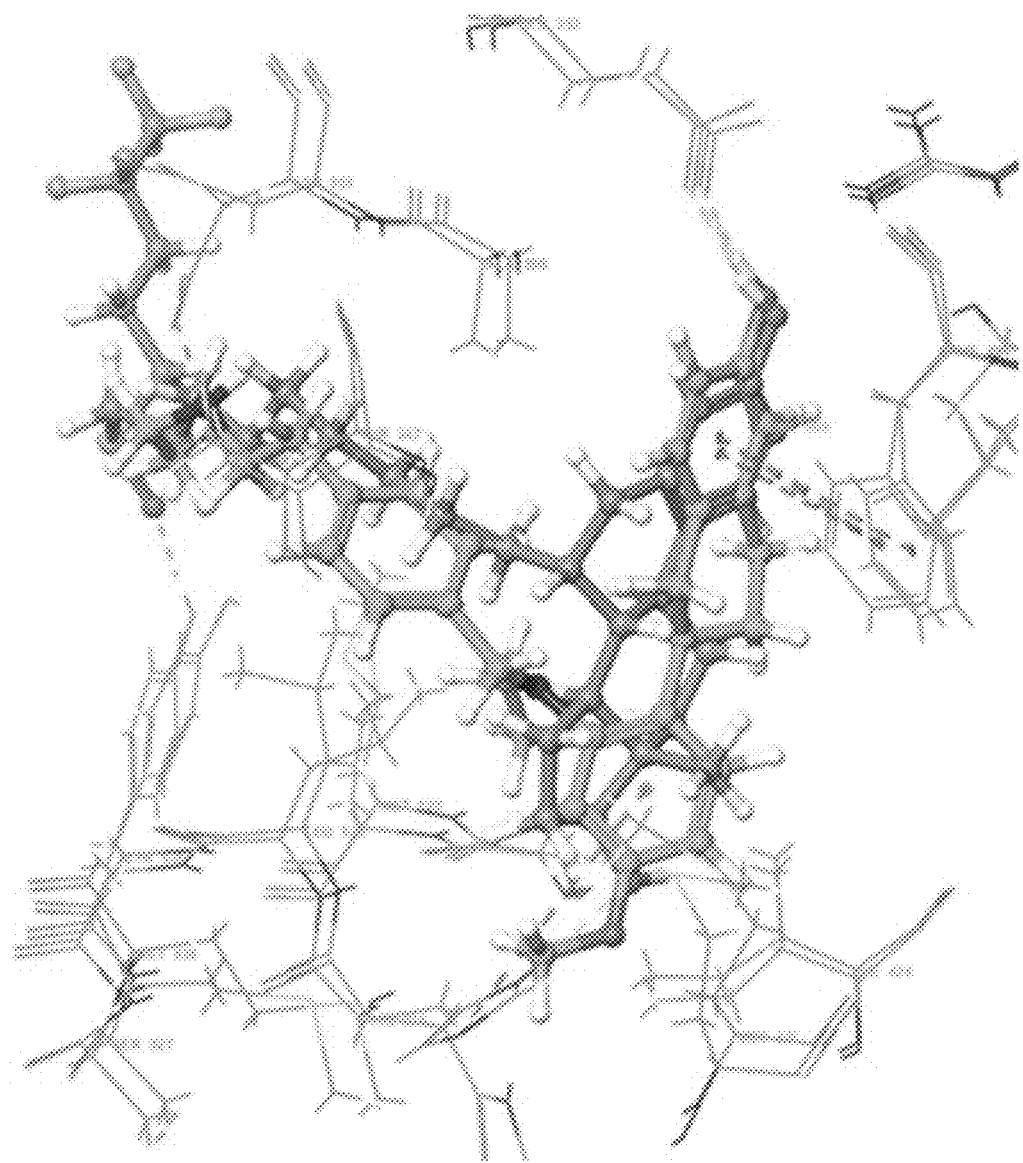
Figure 36:
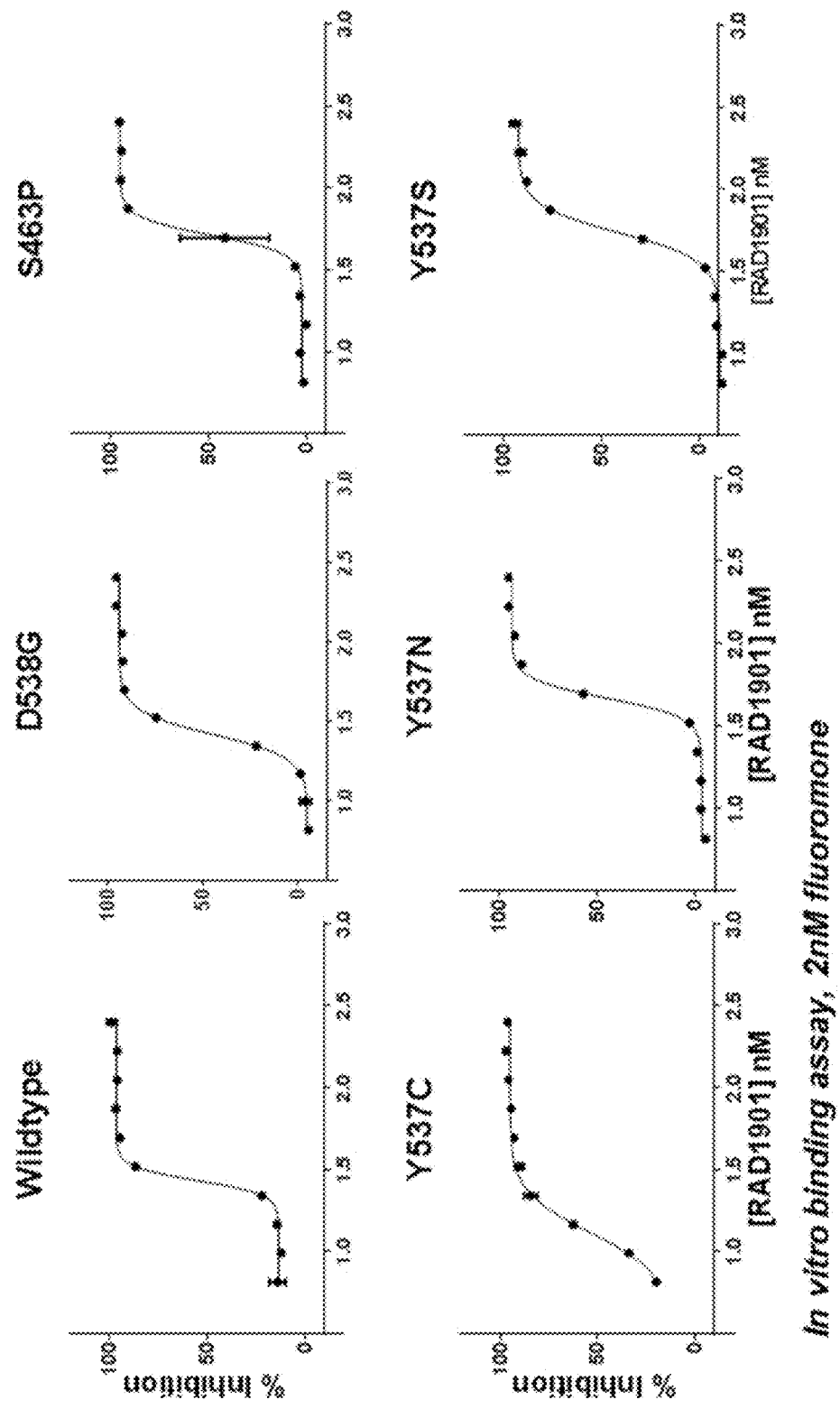

FIG. 20: 3ERT (I).
FIG. 21: 3ERT (II).
FIG. 22: Superimpositions of the ERα LBD-antagonist complexes summarized in Table 11.
FIGS. 23A-B: Modeling of (A) RAD1901-1R5K; and (B) GW5-1R5K.
FIGS. 24A-B: Modeling of (A) RAD1901-1SJ0; and (B) E4D-1SJ0.
FIGS. 25A-B: Modeling of (A) RAD1901-2JFA; and (B) RAL-2JFA.
FIGS. 26A-B: Modeling of (A) RAD1901-2BJ4; and (B) OHT-2BJ4.
FIGS. 27A-B: Modeling of (A) RAD1901-2IOK; and (B) IOK-2IOK.
FIG. 28: Superimpositions of the RAD1901 conformations resulted from IFD analysis with 1R5K and 2OUZ.
FIG. 29: Superimpositions of the RAD1901 conformations resulted from IFD analysis with 2BJ4, and 2JFA.
FIGS. 30A-B: Superimpositions of the RAD1901 conformations resulted from IFD analysis with 2BJ4, 2JFA and 1SJ0.
FIGS. 31A-C: IFD of RAD1901 with 2BJ4.
FIGS. 32A-C: Protein Surface Interactions of RAD1901 docked in 2BJ4 by IFD.
FIGS. 33A-C: IFD of Fulvestrant with 2BJ4.
FIGS. 34A-B: IFD of Fulvestrant and RAD1901 with 2BJ4.
FIGS. 35A-B: Superimpositions of IFD of Fulvestrant and RAD1901 with 2BJ4.
FIG. 36: RAD1901 in vitro binding assay with ERα constructs of WT and LBD mutant.

Table 1. RAD1901 levels in plasma, tumor and brain of mice implanted with MCF7 cells after treated for 40 days. BLQ: below the limit of quantitation.

Table 2. SUV for uterus, muscle, and bone for a human subject treated with 200 mg dose PO once/day for six days.

Table 3. SUV for uterus, muscle, and bone for a human subjects (n=4) treated with 500 mg dose PO once/day for six days.

Table 4. Effect of RAD1901 on BMD in ovariectomized rats. Adult female rats underwent either sham or ovariectomy surgery before treatment initiation with vehicle, E2 (0.01 mg/kg) or RAD1901 (3 mg/kg) once daily (n=20 per treatment group). BMD was measured by dual emission x-ray absorptiometry at baseline and after 4 weeks of treatment. Data are expressed as mean±SD. *P<0.05 versus the corresponding OVX+Veh control. BMD, bone mineral density; E2, beta estradiol; OVX, ovariectomized; Veh, vehicle.

Table 5. Effect of RAD1901 on femur microarchitecture in ovariectomized rats. Adult female rats underwent either sham or ovariectomy surgery before treatment initiation with vehicle, E2 (0.01 mg/kg) or RAD1901 (3 mg/kg) once daily (n=20 per treatment group). After 4 weeks, Bone microarchitecture was evaluated using microcomputed tomography. Data are expressed as mean±SD. *P<0.05 versus the corresponding OVX+Veh control. ABD, apparent bone density; BV/TV, bone volume density; ConnD, connectivity density; E2, beta estradiol; OVX, ovariectomized; TbN, trabecular number; TbTh, trabecular thickness; TbSp, trabecular spacing; Veh, vehicle.

Table 6. Key baseline demographics of Phase 1 dose escalation study of RAD1901.

Table 7. Most frequent (>10%) treatment related AEs in a Phase 1 dose escalation study of RAD1901. AEs graded as per CTCAE v4.0. Any patient with multiple scenarios of a same preferred term was counted only once to the most severe grade. *>10% of patients in the total active group who had any related TEAEs. N=number of subjects with at least one treatment-related AE in a given category.

Table 8. Pharmacokinetic parameters in a Phase 1 dose escalation study of RAD1901 (Day 7).

Table 9. Frequency of LBD mutations.

Table 10. Differences of ER-α LBD-antagonist complexes in residue poses versus 3ERT.

Table 11. Evaluation of structure overlap of ER-α LBD-antagonist complexes by RMSD calculations.

Table 12. Analysis of ligand binding in ER-α LBD-antagonist complexes.

Table 13. Model evaluation for RAD1901 docking.

Table 14. Induced Fit Docking Score of RAD1901 with 1R5K, 1SJ0, 2IFA, 2BJ4 and 2OUZ.

DETAILED DESCRIPTION OF THE INVENTION

As set forth in the Examples section below, a combination of RAD1901 and everolimus (a RAD1901-everolimus combination) (structures below) demonstrated greater tumor growth inhibition than RAD1901 alone in several breast cancer xenograft models, including a wild-type (WT) ERα MCF-7 xenograft model (FIGS. 2A-C), WT ERα PDx-2 (FIGS. 4A-B) and PDx-11 models (FIGS. 3A-B), and a mutant (e.g., Y537S) ERα PDx-5 model (FIGS. 6A-B), regardless of ESR1 status, and prior endocrine therapy as described in Example I. PDx-2, PDx-5 and PDx-11 models had tumor expressing WT or mutant (e.g., Y537S) ERα, with PR expression, with high or low Her2 expression, and with or without prior endocrine therapy (e.g., AI, fulvestrant), and/or chemotherapy (chemo) (FIG. 1). RAD1901 alone also inhibited tumor growth in all other PDx models listed in FIG. 1, having tumor expressing WT or mutant (e.g., Y537S) ERα, with PR expression, with high or low Her2 expression, and with or without prior endocrine therapy (e.g., tamoxifen (tam), AI, fulvestrant), chemotherapy (chemo), Her2 inhibitors (Her2i, e.g., trastuzumab, lapatinib), bevacizumab, and/or rituximab.

ER WT PDx models and ER mutant PDx models may have different level of responsiveness to treatment with fulvestrant alone, everolimus alone, and/or a combination of fulvestrant and everolimus (a ful-everolimus combination). However, RAD1901-everolimus combinations demonstrated improved tumor growth inhibition and/or tumor regression compared to treatment with RAD1901 alone or everolimus alone, regardless of whether the PDx models were responsive to fulvestrant treatment and/or ful-everolimus combination treatment. In other words, RAD1901-everolimus combination may inhibit tumor growth and/or produce tumor regression in fulvestrant resistant cancers.

RAD1901-everolimus combination treatment demonstrated improved tumor growth inhibition and/or tumor regression compared to treatment with fulvestrant alone or with the ful-everolimus combination. For example, the RAD1901-everolimus combination caused more significant tumor regression in more WT ER+ xenograft models than treatment with fulvestrant alone, RAD1901 alone, or everolimus alone, even though these xenograft models have varied responsiveness to fulvestrant treatment (e.g., MCF-7 cell line xenograft model responsive to fulvestrant treatment (FIG. 2); PDx-11 model responsive to fulvestrant treatment (FIG. 3); and PDx-2 model least responsive to fulvestrant treatment (FIG. 4). The RAD1901-everolimus combination also caused more significant tumor regression in more WT ER+ MCF-7 cell line xenograft models and PDx-11 models than treatment with a ful-everolimus combination (FIGS. 2 and 3). The RAD1901-everolimus combination provided similar effects with RAD1901 at a dose of 30 mg/kg or 60 mg/kg, although RAD1901 alone at 30 mg/kg was not as effective as RAD1901 alone at 60 mg/kg in inhibiting tumor growth (FIG. 2C). Said results suggest a RAD1901-everolimus combination with a lower dose of RAD1901 (e.g., 30 mg/kg) was sufficient to maximize the tumor growth inhibition/tumor regression effects in said xenograft models.

The RAD1901-everolimus combination demonstrated tumor regression or improved tumor growth inhibition in mutant ER+ (e.g., Y537S) PDx models hardly responsive to fulvestrant treatment (FIG. 6A). For example, PDx-5 is an ER Y537S mutant PDx model (PR+, Her2−, prior treatment with AI) hardly responsive to fulvestrant treatment. RAD1901-everolimus combination demonstrated tumor regression in PDx-5 model, while everolimus alone or RAD1901 alone only inhibited tumor growth without causing tumor regression (FIG. 6B). The RAD1901-everolimus combination caused more significant tumor growth inhibition than RAD1901 alone, everolimus alone, or fulvestrant alone in mutant PDx-5 models (FIG. 6B). Thus, the addition of everolimus benefited the PDx-5 models when applied in combination with RAD1901. Thus, RAD1901-everolimus combinations provide powerful anti-tumor therapy for ER+ breast cancer expressing WT or mutant ER, with PR expression, with high or low Her2 expression, and with or without resistance to fulvestrant.

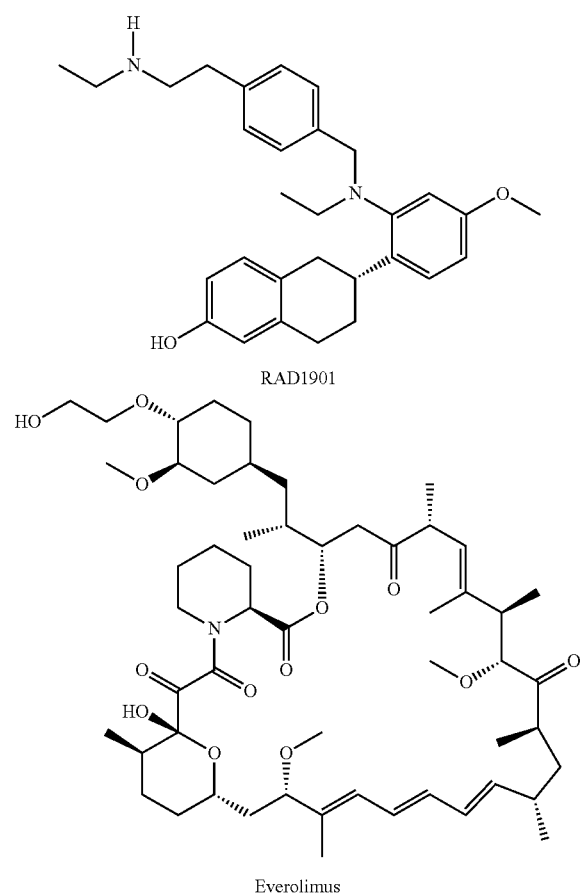

RAD1901

Everolimus

The results provided herein also show that RAD1901 can be delivered to the brain (Example II), and that said delivery improved mouse survival in an intracranial tumor model expressing wild-type ERα (MCF-7 xenograft model, Example I(B)). Everolimus was approved to treat subependymal giant cell astrocytoma (SEGA), a brain tumor seen with tuberous sclerosis (TS). Thus, both components of a RAD1901-everolimus combination are likely to be able to cross the brain-blood barrier and treat ER+ tumors in brain. This represents an additional advantage over the ful-everolimus combination for treating ER+ tumors in the brain, as fulvestrant cannot cross the blood-brain barrier (Vergote1 et al., "Fulvestrant, a new treatment option for advanced breast cancer: tolerability versus existing agents," *Ann. Oncol.*, 17(2):200-204 (2006)). A combination of RAD1901 with other second therapeutic agent(s) that can cross the blood-brain barrier (e.g., mTOR inhibitors such as rapamycin analogs (Geoerger et al., "Antitumor activity of the rapamycin analog CCI-779 in human primitive neuroectodermal tumor/medulloblastoma models as single agent and in combination chemotherapy," *Cancer Res.* 61:1527-1532 (2001))) may also have similar therapeutic effects on ER+ tumors in brain.

RAD1901 showed sustained efficacy in inhibiting tumor growth after RAD1901 treatment ended while estradiol treatment continued (e.g., PDx-4 model). Thus, a RAD1901-everolimus combination is likely to benefit patients by inhibiting tumor growth after treatment ends, especially when the second therapeutic agent(s) treatment may be discontinued (e.g., 29% for everolimus) or reduced or delayed (70% for everolimus-treated patients) for adverse reactions. http://www.fda.gov/Drugs/InformationOnDrugs/ApprovedDrugs/ucm488028.htm.

A RAD1901-everolimus combination is likely to have fewer and/or less severe side-effects than treatment with everolimus alone or a combination of everolimus with other hormone therapies (e.g., AIs such as letrozole and SERDs such as fulvestrant). For example, both AIs and fulvestrant may cause bone loss in treated patients. RAD1901 is unlikely to have similar side effects. RAD1901 was found to preferentially accumulate in tumor, with a RAD1901 level in tumor v. RAD1901 level in plasma (T/P ratio) of up to about 35 (Example II). Standardized uptake values (SUV) for uterus, muscle and bone were calculated for human subjects treated with RAD1901 at a daily dose of about 200 mg up to about 500 mg (Example III(A)). Post-dose uterine signals were close to levels from "non-target tissues" (tissues that do not express estrogen receptor), suggesting a complete attenuation of FES-PET uptake post-RAD1901 treatment. Almost no change was observed in pre- versus post-treatment PET scans in tissues that did not significantly express estrogen receptor (e.g., muscles, bones) (Example IIIA). Finally, RAD1901 treatments antagonized estradiol stimulation of uterine tissues in ovariectomized (OVX) rats (Example IV(A)), and largely preserved bone quality of the treated subjects. For example, OVX rats treated with RAD1901 showed maintained BMD and femur microarchitecture (Example IV(A)). Thus, the RAD1901-everolimus combination may be especially useful for patients having osteoporosis or a higher risk of osteoporosis.

Furthermore, gene expression profiling has been reported as effective for identifying patients responsive to everolimus treatment. Yoon et al., "Gene expression profiling identifies responsive patients with cancer of unknown primary treated with carboplatin, paclitaxel, and everolimus: NCCTG N0871 (alliance)," *Ann. Oncol.*, 27(2):339-44 (2016). Study NCT00805129 found everolimus is more efficient in patients that present somatic mutations in TSC1 as said mutations lead to an increase in recurrence and to an increase in the response time to everolimus. Thus, methods disclosed herein may further comprise gene profiling of subjects to be treated in order to identify subjects with greater response and/or longer responsive time.

Furthermore, RAD1901 was found to degrade wild-type ERα and abrogate ER signaling in vivo in MCF-7 cell line xenograft models, and produced a dose-dependent decrease in PR in these MCF-7 cell line xenograft models (Example III(B)). RAD1901 decreased proliferation in MCF-7 cell line xenograft models and PDx-4 models as evidenced by a decrease in proliferation marker Ki67 in tumors harvested from the treated subjects. RAD1901 also decreased ER signaling in vivo in an ER mutant PDx model that was hardly responsive to fulvestrant treatment (Example III(B)).

The unexpected efficacy of the RAD1901-everolimus combination in treating tumors hardly responsive to fulvestrant treatments and in tumors expressing mutant ERα may be due to the unique interactions between RAD1901 and ERα. Structural models of ERα bound to RAD1901 and other ERα-binding compounds were analyzed to obtain information about the specific binding interactions (Example V). Computer modeling showed that RAD1901-ERα interactions are not likely to be affected by mutations in the LBD of ERα, e.g., Y537X mutant wherein X was S, N, or C; D538G; and S463P, which account for about 81.7% of LBD mutations found in a recent study of metastatic ER positive breast tumor samples from patients who received at least one line of endocrine treatment (Table 9, Example V). Thus, a combination of one or more second therapeutic agent(s) (e.g., everolimus) and RAD1901 or salt or solvate (e.g., hydrate) thereof is likely to have therapeutic effects with relatively low side effects similar to RAD1901-everolimus combinations as disclosed herein. The computer modeling resulted in identification of specific residues in the C-terminal ligand-binding domains of ERα that are critical to binding, information that can be used to develop compounds that bind and antagonize not only wild-type ERα but also certain mutants and variants thereof, which when combined with a second therapeutic agent (e.g., everolimus) may provide strong anti-tumor therapy with relatively low side effects similar to RAD1901-everolimus combinations as disclosed herein.

Based on the results provided herein, methods are provided for inhibiting growth or producing regression of an ERα-positive tumor in a subject in need thereof by administering to the subject a therapeutically effective amount of a combination of RAD1901 or solvates (e.g., hydrates) or salts thereof, plus one or more second therapeutic agent(s) as described herein (e.g., everolimus).

In certain embodiments, administration of RAD1901 or salt or solvate (e.g., hydrate) thereof has additional therapeutic benefits in addition to inhibiting tumor growth, including for example inhibiting cancer cell proliferation or inhibiting ERα activity (e.g., by inhibiting estradiol binding or by degrading ERα). In certain embodiments, the method produces little or no negative effects on non-targeted tissues (e.g., muscles, bones).

In certain embodiments, RAD1901 or salt or solvate (e.g., hydrate) thereof modulates and/or degrades ERα and mutant ERα.

In certain embodiments of the tumor growth inhibition or tumor regression methods provided herein, methods are provided for inhibiting growth or producing regression of an ERα-positive tumor in a subject in need thereof by administering to the subject a therapeutically effective amount of a combination of RAD1901 or a solvate (e.g., hydrate) or salt thereof and one or more second therapeutic agent(s) as described herein. In certain of these embodiments, the salt thereof is RAD1901 dihydrochloride having the structure:

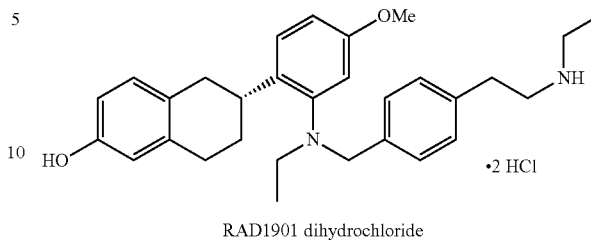

RAD1901 dihydrochloride

Second Therapeutic Agents

A second therapeutic agent for use in the methods provided herein can be a chemotherapeutic agent, or an inhibitor of AKT, androgen receptor, angiogenesis, aromatase, aurora A kinase, BCL2, EGFR, the estrogen pathway, estrogen signaling pathway, estrogen receptor, HER2, HER3, heat shock protein 90 (Hsp90), hedgehog (Hh) signaling pathway, histone deacetylase (HDAC), KIT pathways, mTOR (e.g., TORC1 and/or TORC2), microtubule, MYC, nucleoside metabolism, PARP, pan PI3K, PI3K, protein kinase CK2, the RAS pathway, steroid sulfatase (STS), TK, Top2A, tyrosine kinase, VEGF receptor tyrosine kinase, or any combinations thereof. The second therapeutic agent may also be an antibody such as an anti-TGF beta antibody, anti-type-1 insulin like growth factor receptor antibody, anti-TROP-2 antigen antibody, anti-HER3 antibody, anti-PD1 antibody, or a drug conjugate thereof.

Further examples of second therapeutic agents include, without limitation, abiraterone acetate, ADI-PEG 20, ado-trastuzumab emtansine, afatinib, alisertib, anastrozole, paclitaxel, and paclitaxel derivatives (e.g., ANG1005, paclitaxel polymeric micelle), ARN-810, azacitidine, AZD2014, AZD5363, bevacizumab, BP-C1, buparlisib (BKM120), BYL719, capecitabine, carboplatin, cediranib Maleate, cetuximab, cisplatin/AC4-CDDP4, CR1447, CX-4945, dasatinib, denosumab, docetaxel, doxorubicin, eniluracil, entinostat, enzalutamide, epirubicin, eribulin, exemestane, everolimus, flourouracil, fulvestrant, fresolimumab, ganetespib, ganitumab, GDC-0032, GDC-0941, gemcitabine, glembatumumab vedotin, GnRH agonist (e.g. goserelin acetate), GRN1005, GSK 2141795, ibandronate, IMMU-132, irinotecan, irosustat, epothilone (e.g., ixabepilone), lapatinib, sonidegib (LDE225), letrozole, LGK974, LJM716, lucitanib, methotrexate, MK-2206, MK-3475, MLN0128, MM-302, neratinib, niraparib, olaparib, anti-androgen (e.g., orteronel), oxaliplatin, pazopanib, pertuzumab, PF-05280014, PM01183, progesterone, pyrotinib, romidepsin, ruxolitinib, sorafenib, sunitinib, talazoparib, tamoxifen, taxane, T-DM1, telapristone (CDB-4124), temozolomide, temsirolimus, terathiomolybdate, tesetaxel, TLR 7 agonist, TPI 287, trametinib, trastuzumab, TRC105, trebananib (AMG 386), triptorelin, veliparib, vinflunine, vinorelbine, vorinostat, zoladex, and zoledronic acid, including solvates (e.g., hydrates) and salts thereof.

In certain embodiments, the second therapeutic agents are selected from the group consisting of ado-trastuzumab emtansine, aurora A kinase inhibitors (e.g., alisertib), AIs (e.g., anastrozole; exemestane, letrozole), ARN-810, mTOR inhibitors (e.g., everolimus, AZD2014, BEZ235, GDC-0980, CC-223, MLN0128), AKT inhibitors (e.g., AZD5363, GDC-0068, GSK2110183, GSK2141795, GSK690693, MK2206), PI3K inhibitors (e.g., BKM120, BYL719, GDC- 0032, GDC-0941), selective histone deacetylase (HDAC) inhibitors (e.g., entinostat), GnRH agonist (e.g., goserelin acetate), GRN1005 and combinations thereof with trastuzumab, lapatinib, tyrosine kinase inhibitor (e.g., lucitanib, neratinib), anti-androgen (e.g., orteronel), pertuzumab, temozolomide, and antibodies (e.g., keytruda and BYM338).

In certain embodiments, the second therapeutic agent can be an AI (e.g., anastrozole, aromasin, and letrozole), another SERM (e.g., arzoxifene, droloxifene, EM-652 (SCH 57068), idoxifene, lasofoxifene, levormeloxifene, miproxifene, raloxifene, tamoxifen, and toremifene), or another SERD (e.g., fulvestrant, GDC-0810 (ARN-810), GW5638/DPC974, ICI182782, RU58668, SRN-927, TAS-108 (SR16234), and ZK191703), including solvates (e.g., hydrates) and salts thereof.*

Further examples of the second therapeutic agents include, without limitation, abraxane, AMG 386, cabazitaxel, caelyx, capecitabine, docetaxel, eribulin, gemcitabine, herceptin, neratinib, pazopanib (GW786034), rapalogs (rapamycin and its analogs), taxol (including analogs/alternative formulations), TDM1, temozolamide, tykerb, veliparib (ABT-888), and vinorelbine, including solvates (e.g., hydrates) and salts thereof.

Second Therapeutic Agent Targeting the PI3K/AKT/mTOR Pathway

In some embodiments, the second therapeutic agent targets the PI3K/AKT/mTOR pathway and can be a mTOR inhibitor, a dual mTOR inhibitor, a PI3K/mTOR inhibitor. In some embodiments, the second therapeutic agent is a rapamycin derivative (aka rapalog) such as rapamycin (sirolimus or rapamune, Pfizer), everolimus (Afinitor or RAD001, Novartis), ridaforolimus (AP23573 or MK-8669, Merck and ARIAD Pharmaceuticals), temsirolimus (Torisel or CCI779, Pfizer), including solvates (e.g., hydrates) and salts thereof. In some embodiments, the second therapeutic agent is a dual mTOR inhibitor that inhibits both mTORC1 and mTORC2, such as MLN0128 (castration-resistant prostate cancer (CRPC), Memorial Sloan Kettering Cancer Center), CC115 and CC223 (Celgene), OSI-027 (OSI Pharmaceuticals), and AZD8055 and AZD2014 (AstraZeneca), including solvates (e.g., hydrates) and salts thereof. In some embodiments, the second therapeutic agent is a PI3K/mTOR inhibitor such as GDC-0980, SAR245409 (XL765), LY3023414 (Eli Lilly), NVP-BEZ235 (Novartis), NVP-BGT226 (Novartis), SF1126, and PKI-587 (Pfizer), including solvates (e.g., hydrates) and salts thereof.

In certain embodiments, more than one of the second therapeutic agents disclosed above may be used in combination with RAD1901 or solvates (e.g., hydrate) or salts thereof. For example, an mTOR inhibitor can be used together with another mTOR inhibitor or with a PI3K/mTOR inhibitor. Also, it is known in the art that the second therapeutic agents disclosed above, including mTOR inhibitors, dual mTOR inhibitors, and PI3K/mTOR inhibitors, can be administered with other active agents to enhance the efficacy of the treatment. For example, an mTOR inhibitor can be used in combination with JAK2 inhibitors (Bogani et al., *PLOS One,* 8(1): e54826 (2013)), chemotherapeutic agents (Yardley, *Breast Cancer (Auckl)* 7: 7-22 (2013)), or endocrine therapies such as tamoxifen or exemestane (Vinayak et al., "mTOR inhibitors in the treatment of breast cancer," *Oncology,* published Jan. 15, 2013 (http://www.cancernetwork.com/breast-cancer/mtor-inhibitors-treatment-breast-cancer)). Accordingly, the second therapeutic agents also include these auxiliary active agents.

Combination Therapy (1) Combination of RAD1901 or Solvates (e.g., Hydrate) or Salts Thereof and One or More Second Therapeutic Agent(s)

Both the RAD1901 or solvates (e.g., hydrate) or salts thereof and the second therapeutic agent(s) (e.g., everolimus), when administered alone to a subject, have a therapeutic effect on one or more cancers or tumors (Examples I(A) and I(B)). It was surprisingly discovered that when administered in combination to a subject, RAD1901 or solvates (e.g., hydrate) or salts thereof and the second therapeutic agent(s) (e.g., everolimus) have a significantly improved effect on the cancers/tumors (Examples I(A) and I(B)).

"Inhibiting growth" of an ERα-positive tumor as used herein may refer to slowing the rate of tumor growth, or halting tumor growth entirely.

"Tumor regression" or "regression" of an ERα-positive tumor as used herein may refer to reducing the maximum size of a tumor. In certain embodiments, administration of a combination of one or more second therapeutic agent(s) (e.g., everolimus) as described herein (e.g., ribociclib, abemaciclib and everolimus) and RAD1901 or a solvate (e.g., hydrate) or salt thereof may result in a decrease in tumor size versus baseline (i.e., size prior to initiation of treatment), or even eradication or partial eradication of a tumor. Accordingly, in certain embodiments the methods of tumor regression provided herein may be alternatively characterized as methods of reducing tumor size versus baseline.

"Tumor" as used herein is a malignant tumor, and is used interchangeably with "cancer."

Tumor growth inhibition or regression may be localized to a single tumor or to a set of tumors within a specific tissue or organ, or may be systemic (i.e., affecting tumors in all tissues or organs).

As RAD1901 is known to preferentially bind ERα versus estrogen receptor beta (ERβ), unless specified otherwise, estrogen receptor, estrogen receptor alpha, ERα, ER, wild-type ERα, and ESR1 are used interchangeably herein. "Estrogen receptor alpha" or "ERα" as used herein refers to a polypeptide comprising, consisting of, or consisting essentially of the wild-type ERα amino acid sequence, which is encoded by the gene ESR1. A tumor that is "positive for estrogen receptor alpha," "ERα-positive," "ER+," or "ERα+" as used herein refers to a tumor in which one or more cells express at least one isoform of ERα. In certain embodiments, these cells overexpress ERα. In certain embodiments, the patient has one or more cells within the tumor expressing one or more forms of ERβ. In certain embodiments, the ERα-positive tumor and/or cancer is associated with breast, uterine, ovarian, or pituitary cancer. In certain of these embodiments, the patient has a tumor located in breast, uterine, ovarian, or pituitary tissue. In those embodiments where the patient has a tumor located in the breast, the tumor may be associated with luminal breast cancer that may or may not be positive for HER2, and for HER2+ tumors, the tumors may express high or low HER2 (e.g., FIG. 1). In other embodiments, the patient has a tumor located in another tissue or organ (e.g., bone, muscle, brain), but is nonetheless associated with breast, uterine, ovarian, or pituitary cancer (e.g., tumors derived from migration or metastasis of breast, uterine, ovarian, or pituitary cancer). Accordingly, in certain embodiments of the tumor growth inhibition or tumor regression methods provided herein, the tumor being targeted is a metastatic tumor and/or the tumor has an overexpression of ER in other organs (e.g., bones and/or muscles). In certain embodiments, the tumor being targeted is a brain tumor and/or cancer. In certain embodiments, the tumor being targeted is more sensitive to a treatment of RAD1901 and a second therapeutic agent as disclosed herein than treatment with another SERD (e.g., fulvestrant, TAS-108 (SR16234), ZK191703, RU58668, GDC-0810 (ARN-810), GW5638/DPC974, SRN-927, ICI182782 and AZD9496), Her2 inhibitors (e.g., trastuzumab, lapatinib, ado-trastuzumab emtansine, and/or pertuzumab), chemo therapy (e.g., abraxane, adriamycin, carboplatin, cytoxan, daunorubicin, doxil, ellence, fluorouracil, gemzar, helaven, lxempra, methotrexate, mitomycin, micoxantrone, navelbine, taxol, taxotere, thiotepa, vincristine, and xeloda), aromatase inhibitor (e.g., anastrozole, exemestane, and letrozole), selective estrogen receptor modulators (e.g., tamoxifen, raloxifene, lasofoxifene, and/or toremifene), angiogenesis inhibitor (e.g., bevacizumab), and/or rituximab.

In certain embodiments of the tumor growth inhibition or tumor regression methods provided herein, the methods further comprise a step of determining whether a patient has a tumor expressing ERα prior to administering a combination of RAD1901 or solvates (e.g., hydrate) or salts thereof and one or more second therapeutic agent(s) (e.g., everolimus). In certain embodiments of the tumor growth inhibition or tumor regression methods provided herein, the methods further comprise a step of determining whether the patient has a tumor expressing mutant ERα prior to administering a combination of RAD1901 or solvates (e.g., hydrate) or salts thereof and one or more second therapeutic agent(s) (e.g., everolimus). In certain embodiments of the tumor growth inhibition or tumor regression methods provided herein, the methods further comprise a step of determining whether a patient has a tumor expressing ERα that is responsive or non-responsive to fulvestrant treatment prior to administering a combination of RAD1901 or solvates (e.g., hydrate) or salts thereof and one or more second therapeutic agent(s) (e.g., everolimus). These determinations may be made using any method of expression detection known in the art, and may be performed in vitro using a tumor or tissue sample removed from the subject.

In addition to demonstrating the ability of RAD1901 to inhibit tumor growth in tumors expressing wild-type ERα, the results provided herein show that RAD1901 exhibited the unexpected ability to inhibit the growth of tumors expressing a mutant form of ERα, namely Y537S ERα (Example I(A)). Computer modeling evaluations of examples of ERα mutations showed that none of these mutations were expected to impact the LBD or specifically hinder RAD1901 binding (Example V(A)), e.g., ERα having one or more mutants selected from the group consisting of ERα with Y537X mutant wherein X is S, N, or C, ERα with D538G mutant, and ERα with S463P mutant. Based on these results, methods are provided herein for inhibiting growth or producing regression of a tumor that is positive for ERα having one or more mutants within the ligand-binding domain (LBD), selected from the group consisting of $Y537X_1$ wherein $X_1$ is S, N, or C, D538G, $L536X_2$ wherein $X_2$ is R or Q, P535H, V534E, S463P, V392I, E380Q, especially Y537S ERα, in a subject with cancer by administering to the subject a therapeutically effective amount of a combination of one or more one or more second therapeutic agent(s) (e.g., everolimus) and RAD1901 or solvates (e.g., hydrate) or salts thereof. "Mutant ERα" as used herein refers to ERα comprising one or more substitutions or deletions, and variants thereof comprising, consisting of, or consisting essentially of an amino acid sequence with at least 80%, at least 85%, at least 90%, at least 95%, at least 97%, at least 98%, at least 99%, or at least 99.5% identity to the amino acid sequence of ERα.

In addition to inhibiting breast cancer tumor growth in an animal xenograft model, the results disclosed herein show that RAD1901 exhibits significant accumulation within tumor cells, and is capable of penetrating the blood-brain barrier (Example II). The ability to penetrate the blood-brain barrier was confirmed by showing that RAD1901 administration significantly prolonged survival in a brain metastasis xenograft model (Example I(B)). Accordingly, in certain embodiments of the tumor growth inhibition or tumor regression methods provided herein, the ERα-positive tumor being targeted is located in the brain or elsewhere in the central nervous system. In certain of these embodiments, the ERα-positive tumor is primarily associated with brain cancer. In other embodiments, the ERα-positive tumor is a metastatic tumor that is primarily associated with another type of cancer, such as breast, uterine, ovarian, or pituitary cancer, or a tumor that has migrated from another tissue or organ. In certain of these embodiments, the tumor is a brain metastases, such as breast cancer brain metastases (BCBM). In certain embodiments of the methods disclosed herein, RAD1901 or solvates (e.g., hydrate) or salts thereof accumulate in one or more cells within a target tumor.

In certain embodiments of the methods disclosed herein, RAD1901 or solvates (e.g., hydrate) or salts thereof preferably accumulate in tumor at a T/P (RAD1901 concentration in tumor/RAD1901 concentration in plasma) ratio of about 15 or higher, about 18 or higher, about 19 or higher, about 20 or higher, about 25 or higher, about 28 or higher, about 30 or higher, about 33 or higher, about 35 or higher, or about 40 or higher.

The results provided herein show that RAD1901 administration protects against bone loss in ovariectomized rats (Example IV(A)). Accordingly, in certain embodiments of the tumor growth inhibition or tumor regression methods provided herein, administration of a combination of one or more second therapeutic agent(s) (e.g., everolimus) and RAD1901 or solvates (e.g., hydrate) or salts thereof does not have undesirable effects on bone, including for example undesirable effects on bone volume density, bone surface density, bone mineral density, trabecular number, trabecular thickness, trabecular spacing, connectivity density, and/or apparent bone density of the treated subject. As tamoxifen may be associated with bone loss in premenopausal women, and fulvestrant may impair the bone structures due to its mechanism of action, a combination of one or more one or more second therapeutic agent(s) (e.g., everolimus) and RAD1901 or solvates (e.g., hydrate) or salts thereof can be particularly useful for premenopausal women, tumors resistant to tamoxifen or antiestrogen therapy, and patients having osteoporosis and/or high risk of osteoporosis.

The results provided herein show that RAD1901 antagonized estradiol stimulation of uterine tissues in ovariectomized rats (Example IV(A)). Furthermore, in human subjects treated with RAD1901 at a daily dosage of 200 mg or up to 500 mg, standardized uptake value (SUV) for uterus, muscle, and bone tissues that did not significantly express ER showed hardly any changes in signals pre- and post-treatment (Example III(A)). Accordingly, in certain embodiments, such administration also does not result in undesirable effects on other tissues, including for example uterine, muscle, or breast tissue.

RAD1901 or solvates (e.g., hydrate) or salts thereof and the second therapeutic agent(s) (e.g., everolimus) are administered in combination to a subject in need. The phrase "in combination" means that RAD1901 or solvates (e.g., hydrate) or salts thereof may be administered before, during, or after the administration of the second therapeutic agent(s)

(e.g., everolimus). For example, RAD1901 or solvates (e.g., hydrate) or salts thereof and the second therapeutic agent(s) (e.g., everolimus) can be administered in about one week apart, about 6 days apart, about 5 days apart, about 4 days apart, about 3 days apart, about 2 days apart, about 24 hours apart, about 23 hours apart, about 22 hours apart, about 21 hours apart, about 20 hours apart, about 19 hours apart, about 18 hours apart, about 17 hours apart, about 16 hours apart, about 15 hours apart, about 14 hours apart, about 13 hours apart, about 12 hours apart, about 11 hours apart, about 10 hours apart, about 9 hours apart, about 8 hours apart, about 7 hours apart, about 6 hours apart, about 5 hours apart, about 4 hours apart, about 3 hours apart, about 2 hours apart, about 1 hour apart, about 55 minutes apart, about 50 minutes apart, about 45 minutes apart, about 40 minutes apart, about 35 minutes apart, about 30 minutes apart, about 25 minutes apart, about 20 minutes apart, about 15 minutes apart, about 10 minutes apart, or about 5 minutes apart. In other embodiments RAD1901 or solvates (e.g., hydrate) or salts thereof and the second therapeutic agent(s) (e.g., everolimus) are administered to the subject simultaneously or substantially simultaneously. In certain of these embodiments, RAD1901 or solvates (e.g., hydrate) or salts thereof and the second therapeutic agent(s) (e.g., everolimus) may be administered as part of a single formulation.

In some embodiments, the combination of RAD1901 or solvates (e.g., hydrate) or salts thereof and a single second therapeutic agent (e.g., everolimus) is administered to a subject. In other embodiments, the combination of RAD1901 or solvates (e.g., hydrate) or salts thereof and more than one second therapeutic agent (e.g., everolimus) is administered to a subject. For example, RAD1901 or solvates (e.g., hydrate) or salts thereof can be combined with two or more second therapeutic agent(s) (e.g., everolimus) for treating cancers/tumors.

(2) Dosage

A therapeutically effective amount of a combination of RAD1901 or solvates (e.g., hydrate) or salts thereof and one or more second therapeutic agent(s) (e.g., everolimus) for use in the methods disclosed herein is an amount that, when administered over a particular time interval, results in achievement of one or more therapeutic benchmarks (e.g., slowing or halting of tumor growth, resulting in tumor regression, cessation of symptoms, etc.). The combination for use in the presently disclosed methods may be administered to a subject one time or multiple times. In those embodiments wherein the compounds are administered multiple times, they may be administered at a set interval, e.g., daily, every other day, weekly, or monthly. Alternatively, they can be administered at an irregular interval, for example on an as-needed basis based on symptoms, patient health, and the like. A therapeutically effective amount of the combination may be administered daily for one day, at least 2 days, at least 3 days, at least 4 days, at least 5 days, at least 6 days, at least 7 days, at least 10 days, or at least 15 days. Optionally, the status of the cancer or the regression of the tumor is monitored during or after the treatment, for example, by a FES-PET scan of the subject. The dosage of the combination administered to the subject can be increased or decreased depending on the status of the cancer or the regression of the tumor detected.

Ideally, the therapeutically effective amount does not exceed the maximum tolerated dosage at which 50% or more of treated subjects experience nausea or other toxicity reactions that prevent further drug administrations. A therapeutically effective amount may vary for a subject depending on a variety of factors, including variety and extent of the symptoms, sex, age, body weight, or general health of the subject, administration mode and salt or solvate type, variation in susceptibility to the drug, the specific type of the disease, and the like.

Examples of therapeutically effective amounts of RAD1901 or solvates (e.g., hydrate) or salts thereof for use in the methods disclosed herein include, without limitation, about 150 to about 1,500 mg, about 200 to about 1,500 mg, about 250 to about 1,500 mg, or about 300 to about 1,500 mg daily dosage for subjects having resistant ER-driven tumors or cancers; about 150 to about 1,500 mg, about 200 to about 1,000 mg or about 250 to about 1,000 mg or about 300 to about 1,000 mg daily dosage for subjects having both wild-type ER driven tumors and/or cancers and resistant tumors and/or cancers; and about 300 to about 500 mg, about 300 to about 550 mg, about 300 to about 600 mg, about 250 to about 500 mg, about 250 to about 550 mg, about 250 to about 600 mg, about 200 to about 500 mg, about 200 to about 550 mg, about 200 to about 600 mg, about 150 to about 500 mg, about 150 to about 550 mg, or about 150 to about 600 mg daily dosage for subjects having majorly wild-type ER driven tumors and/or cancers.

A therapeutically effective amount or dosage of a second therapeutic agent (e.g., everolimus) depends on its particular type. In general, the daily dosage of a second therapeutic agent (e.g., everolimus) ranges from about 1 mg to about 1,500 mg, from about 1 mg to about 1,200 mg, from about 1 mg to about 1,000 mg, from about 1 mg to about 800 mg, from about 1 mg to about 600 mg, from about 1 mg to about 500 mg, from about 1 mg to about 200 mg, from about 1 mg to about 100 mg, from about 1 mg to about 50 mg, from about 1 mg to about 30 mg, from about 1 mg to about 20 mg, from about 1 mg to about 10 mg, from about 1 mg to about 5 mg, from about 50 mg to about 1,500 mg, from about 100 mg to about 1,200 mg, from about 150 mg to about 1,000 mg, from about 200 mg to about 800 mg, from about 300 mg to about 600 mg, from about 350 mg to about 500 mg. The daily dosage of a second therapeutic agent (e.g., everolimus) may range from about 1 to about 100 mg/kg, from about 1 to about 75 mg/kg, from about 1 to about 50 mg/kg, from about 1 to about 45 mg/kg, from about 1 to about 40 mg/kg, from about 1 to about 30 mg/kg, from about 1 to about 20 mg/kg, from about 1 to about 10 mg/kg, from about 2 to about 100 mg/kg, from about 2 to about 75 mg/kg, from about 2 to about 50 mg/kg, from about 2 to about 45 mg/kg, from about 2 to about 40 mg/kg, from about 2 to about 30 mg/kg, from about 2 to about 20 mg/kg, from about 2 to about 10 mg/kg, from about 2.5 to about 100 mg/kg, from about 2.5 to about 75 mg/kg, from about 2.5 to about 50 mg/kg, from about 2.5 to about 45 mg/kg, from about 2.5 to about 40 mg/kg, from about 2.5 to about 30 mg/kg, from about 2.5 to about 20 mg/kg, or from about 2.5 to about 10 mg/kg.

In certain embodiments, a therapeutically effective amount of the combination may utilize a therapeutically effective amount of either compound administered alone. In other embodiments, due to the significantly improved, synergistic therapeutic effect achieved by the combination, the therapeutically effective amounts of RAD1901 or solvates (e.g., hydrate) or salts thereof and the second therapeutic agent(s) (e.g., everolimus) when administered in the combination may be smaller than the therapeutically effective amounts of RAD1901 or solvates (e.g., hydrate) or salts thereof and the second therapeutic agent(s) (e.g., everolimus) required when administered alone; and one or both compounds may be administered at a dosage that is lower than the dosage at which they would normally be administered when given separately. Without being bound by any specific theory, the combination therapy achieves a significantly improved effect by reducing the dosage of at least one or all of RAD1901 or solvates (e.g., hydrate) or salts thereof and the second therapeutic agent(s) (e.g., everolimus), thereby eliminating or alleviating undesirable toxic side effects.

In some embodiments, the therapeutically effective amount of RAD1901 or solvates (e.g., hydrate) or salts thereof when administered as part of the combination is about 30% to about 200%, about 40% to about 200%, about 50% to about 200%, about 60% to about 200%, about 70% to about 200%, about 80% to about 200%, about 90% to about 200%, about 100% to about 200%, 30% to about 150%, about 40% to about 150%, about 50% to about 150%, about 60% to about 150%, about 70% to about 150%, about 80% to about 150%, about 90% to about 150%, about 100% to about 150%, about 30% to about 120%, about 40% to about 120%, about 50% to about 120%, about 60% to about 120%, about 70% to about 120%, about 80% to about 120%, about 90% to about 120%, about 100% to about 120%, 30% to about 110%, about 40% to about 110%, about 50% to about 110%, about 60% to about 110%, about 70% to about 110%, about 80% to about 110%, about 90% to about 110%, or about 100% to about 110% of the therapeutically effective amount of RAD1901 or solvates (e.g., hydrate) or salts thereof when administered alone. In some embodiments, the therapeutically effective amount of the second therapeutic agent(s) (e.g., everolimus) when administered as part of the combination is about 30% to about 200%, about 40% to about 200%, about 50% to about 200%, about 60% to about 200%, about 70% to about 200%, about 80% to about 200%, about 90% to about 200%, about 100% to about 200%, 30% to about 150%, about 40% to about 150%, about 50% to about 150%, about 60% to about 150%, about 70% to about 150%, about 80% to about 150%, about 90% to about 150%, about 100% to about 150%, about 30% to about 120%, about 40% to about 120%, about 50% to about 120%, about 60% to about 120%, about 70% to about 120%, about 80% to about 120%, about 90% to about 120%, about 100% to about 120%, 30% to about 110%, about 40% to about 110%, about 50% to about 110%, about 60% to about 110%, about 70% to about 110%, about 80% to about 110%, about 90% to about 110%, or about 100% to about 110% of the therapeutically effective amount of the second therapeutic agent(s) (e.g., everolimus) when administered alone.

In certain embodiments, the cancers or tumors are resistant ER-driven cancers or tumors (e.g. having mutant ER binding domains (e.g. ERα comprising one or more mutations including, but not limited to, $Y537X_1$ wherein $X_1$ is S, N, or C, D538G, $L536X_2$ wherein $X_2$ is R or Q, P535H, V534E, S463P, V392I, E380Q and combinations thereof), overexpressors of the ERs or tumor and/or cancer proliferation becomes ligand independent, or tumors and/or cancers that progress with treatment of another SERD (e.g., fulvestrant, TAS-108 (SR16234), ZK191703, RU58668, GDC-0810 (ARN-810), GW5638/DPC974, SRN-927, ICI182782 and AZD9496), Her2 inhibitors (e.g., trastuzumab, lapatinib, ado-trastuzumab emtansine, and/or pertuzumab), chemo therapy (e.g., abraxane, adriamycin, carboplatin, cytoxan, daunorubicin, doxil, ellence, fluorouracil, gemzar, helaven, lxempra, methotrexate, mitomycin, micoxantrone, navelbine, taxol, taxotere, thiotepa, vincristine, and xeloda), aromatase inhibitor (e.g., anastrozole, exemestane, and letrozole), selective estrogen receptor modulators (e.g., tamoxifen, raloxifene, lasofoxifene, and/or toremifene), angiogenesis inhibitor (e.g., bevacizumab), and/or rituximab.

In certain embodiments, the dosage of RAD1901 or solvates (e.g., hydrate) or salts thereof in a combination with a second therapeutic agent (e.g., everolimus) as described herein (e.g., ribociclib, abemaciclib and everolimus) for use in the presently disclosed methods general for an adult subject may be approximately 30 µg to 2,000 mg, 100 µg to 1,500 mg, or 150 mg to 1,500 mg per day via oral administration. This daily dosage may be achieved via a single administration or multiple administrations.

A combination of one or more second therapeutic agent(s) (e.g., everolimus) and RAD1901 or solvates (e.g., hydrate) or salts thereof may be administered to a subject one time or multiple times. In those embodiments wherein the compounds are administered multiple times, they may be administered at a set interval, e.g., daily, every other day, weekly, or monthly. Alternatively, they can be administered at an irregular interval, for example on an as-needed basis based on symptoms, patient health, and the like.

(3) Formulation

In some embodiments, RAD1901 or solvates (e.g., hydrate) or salts thereof and the second therapeutic agent(s) (e.g., everolimus) are administered in separate formulations. In certain of these embodiments, the formulations may be of the same type. For example, both formulations may be designed for oral administration (e.g., via two separate pills) or for injection (e.g., via two separate injectable formulations). In other embodiments, RAD1901 or solvates (e.g., hydrate) or salts thereof and the second therapeutic agent(s) (e.g., everolimus) may be formulated in different types of formulations. For example, one compound may be in a formulation designed for oral administration, while the other is in a formulation designed for injection.

In other embodiments, RAD1901 or solvates (e.g., hydrate) or salts thereof and the second therapeutic agent(s) (e.g., everolimus) described herein are administered as part of a single formulation. For example, RAD1901 or solvates (e.g., hydrate) or salts thereof and the second therapeutic agent(s) (e.g., everolimus) are formulated in a single pill for oral administration or in a single dose for injection. Provided herein in certain embodiments are combination formulations comprising RAD1901 or solvates (e.g., hydrate) or salts thereof and one or more second therapeutic agent(s) (e.g., everolimus). In certain embodiments, administration of the compounds in a single formulation improves patient compliance.

The therapeutically effective amount of each compound when administered in combination may be lower than the therapeutically effective amount of each compound administered alone.

In some embodiments, a formulation comprising RAD1901 or solvates (e.g., hydrate) or salts thereof, one or more to the second therapeutic agent(s) (e.g., everolimus), or both RAD1901 or solvates (e.g., hydrate) or salts thereof and the one or more second therapeutic agent(s) (e.g., everolimus) may further comprise one or more pharmaceutical excipients, carriers, adjuvants, and/or preservatives.

RAD1901 or solvates (e.g., hydrate) or salts thereof and the second therapeutic agent(s) (e.g., everolimus) for use in the presently disclosed methods can be formulated into unit dosage forms, meaning physically discrete units suitable as unitary dosage for subjects undergoing treatment, with each unit containing a predetermined quantity of active material calculated to produce the desired therapeutic effect, optionally in association with a suitable pharmaceutical carrier.

The unit dosage form can be for a single daily dose or one of multiple daily doses (e.g., about 1 to 4 or more times per day). When multiple daily doses are used, the unit dosage form can be the same or different for each dose. In certain embodiments, the compounds may be formulated for controlled release.

RAD1901 or solvates (e.g., hydrate) or salts thereof and the second therapeutic agent(s) (e.g., everolimus) for use in the presently disclosed methods can be formulated according to any available conventional method. Examples of preferred dosage forms include a tablet, a powder, a subtle granule, a granule, a coated tablet, a capsule, a syrup, a troche, an inhalant, a suppository, an injectable, an ointment, an ophthalmic ointment, an eye drop, a nasal drop, an ear drop, a cataplasm, a lotion and the like. In the formulation, generally used additives such as a diluent, a binder, an disintegrant, a lubricant, a colorant, a flavoring agent, and if necessary, a stabilizer, an emulsifier, an absorption enhancer, a surfactant, a pH adjuster, an antiseptic, an antioxidant and the like can be used. In addition, the formulation is also carried out by combining compositions that are generally used as a raw material for pharmaceutical formulation, according to the conventional methods. Examples of these compositions include, for example, (1) an oil such as a soybean oil, a beef tallow and synthetic glyceride; (2) hydrocarbon such as liquid paraffin, squalane and solid paraffin; (3) ester oil such as octyldodecyl myristic acid and isopropyl myristic acid; (4) higher alcohol such as cetostearyl alcohol and behenyl alcohol; (5) a silicon resin; (6) a silicon oil; (7) a surfactant such as polyoxyethylene fatty acid ester, sorbitan fatty acid ester, glycerin fatty acid ester, polyoxyethylene sorbitan fatty acid ester, a solid polyoxyethylene castor oil and polyoxyethylene polyoxypropylene block co-polymer; (8) water soluble macromolecule such as hydroxyethyl cellulose, polyacrylic acid, carboxyvinyl polymer, polyethyleneglycol, polyvinylpyrrolidone and methylcellulose; (9) lower alcohol such as ethanol and isopropanol; (10) multivalent alcohol such as glycerin, propyleneglycol, dipropyleneglycol and sorbitol; (11) a sugar such as glucose and cane sugar; (12) an inorganic powder such as anhydrous silicic acid, aluminum magnesium silicicate and aluminum silicate; (13) purified water, and the like. Additives for use in the above formulations may include, for example, 1) lactose, corn starch, sucrose, glucose, mannitol, sorbitol, crystalline cellulose and silicon dioxide as the diluent; 2) polyvinyl alcohol, polyvinyl ether, methyl cellulose, ethyl cellulose, gum arabic, tragacanth, gelatine, shellac, hydroxypropyl cellulose, hydroxypropylmethyl cellulose, polyvinylpyrrolidone, polypropylene glycol-poly oxyethylene-block co-polymer, meglumine, calcium citrate, dextrin, pectin and the like as the binder; 3) starch, agar, gelatine powder, crystalline cellulose, calcium carbonate, sodium bicarbonate, calcium citrate, dextrin, pectic, carboxymethylcellulose/calcium and the like as the disintegrant; 4) magnesium stearate, talc, polyethyleneglycol, silica, condensed plant oil and the like as the lubricant; 5) any colorants whose addition is pharmaceutically acceptable is adequate as the colorant; 6) cocoa powder, menthol, aromatizer, peppermint oil, cinnamon powder as the flavoring agent; 7) antioxidants whose addition is pharmaceutically accepted such as ascorbic acid or alpha-tophenol.

RAD1901 or solvates (e.g., hydrate) or salts thereof and one or more second therapeutic agent(s) (e.g., everolimus) for use in the presently disclosed methods can be formulated into a pharmaceutical composition as any one or more of the active compounds described herein and a physiologically acceptable carrier (also referred to as a pharmaceutically acceptable carrier or solution or diluent). Such carriers and solutions include pharmaceutically acceptable salts and solvates of compounds used in the methods of the instant invention, and mixtures comprising two or more of such compounds, pharmaceutically acceptable salts of the compounds and pharmaceutically acceptable solvates of the compounds. Such compositions are prepared in accordance with acceptable pharmaceutical procedures such as described in Remington's Pharmaceutical Sciences, 18th edition, ed. Alfonso R. Gennaro, Mack Printing Company, Eaton, Pa. (1990), which is incorporated herein by reference.

The term "pharmaceutically acceptable carrier" refers to a carrier that does not cause an allergic reaction or other untoward effect in patients to whom it is administered and are compatible with the other ingredients in the formulation. Pharmaceutically acceptable carriers include, for example, pharmaceutical diluents, excipients or carriers suitably selected with respect to the intended form of administration, and consistent with conventional pharmaceutical practices. For example, solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof. Pharmaceutically acceptable carriers may further comprise minor amounts of auxiliary substances such as wetting or emulsifying agents, preservatives or buffers, which enhance the shelf life or effectiveness of the therapeutic agent.

The one or more second therapeutic agent(s) (e.g., everolimus) and RAD1901 or solvates (e.g., hydrate) or salts thereof in a free form can be converted into a salt by conventional methods. The term "salt" used herein is not limited as long as the salt is formed with RAD1901 or solvates (e.g., hydrate) or salts thereof and is pharmacologically acceptable; preferred examples of salts include a hydrohalide salt (for instance, hydrochloride, hydrobromide, hydroiodide and the like), an inorganic acid salt (for instance, sulfate, nitrate, perchlorate, phosphate, carbonate, bicarbonate and the like), an organic carboxylate salt (for instance, acetate salt, maleate salt, tartrate salt, fumarate salt, citrate salt and the like), an organic sulfonate salt (for instance, methanesulfonate salt, ethanesulfonate salt, benzenesulfonate salt, toluenesulfonate salt, camphorsulfonate salt and the like), an amino acid salt (for instance, aspartate salt, glutamate salt and the like), a quaternary ammonium salt, an alkaline metal salt (for instance, sodium salt, potassium salt and the like), an alkaline earth metal salt (magnesium salt, calcium salt and the like) and the like. In addition, hydrochloride salt, sulfate salt, methanesulfonate salt, acetate salt and the like are preferred as "pharmacologically acceptable salt" of the compounds according to the present invention.

Isomers of RAD1901 or solvates (e.g., hydrate) or salts thereof and/or the second therapeutic agent(s) (e.g., everolimus) (e.g., geometric isomers, optical isomers, rotamers, tautomers, and the like) can be purified using general separation means, including for example recrystallization, optical resolution such as diastereomeric salt method, enzyme fractionation method, various chromatographies (for instance, thin layer chromatography, column chromatography, glass chromatography and the like) into a single isomer. The term "a single isomer" herein includes not only an isomer having a purity of 100%, but also an isomer containing an isomer other than the target, which exists even through the conventional purification operation. A crystal polymorph sometimes exists for RAD1901 or solvates (e.g., hydrate) or salts thereof and/or a second therapeutic agent (e.g., everolimus), and all crystal polymorphs thereof are included in the present invention. The crystal polymorph is sometimes single and sometimes a mixture, and both are included herein.

In certain embodiments, RAD1901 or solvates (e.g., hydrate) or salts thereof and/or second therapeutic agent (e.g., everolimus) may be in a prodrug form, meaning that it must undergo some alteration (e.g., oxidation or hydrolysis) to achieve its active form. Alternative, RAD1901 or solvates (e.g., hydrate) or salts thereof and/or second therapeutic agent (e.g., everolimus) may be a compound generated by alteration of a parental prodrug to its active form.

(4) Administration Route

Administration routes of RAD1901 or solvates (e.g., hydrate) or salts thereof and/or second therapeutic agent(s) (e.g., everolimus) disclosed herein include but not limited to topical administration, oral administration, intradermal administration, intramuscular administration, intraperitoneal administration, intravenous administration, intravesical infusion, subcutaneous administration, transdermal administration, and transmucosal administration.

(5) Gene Profiling

In certain embodiments, the methods of tumor growth inhibition or tumor regression provided herein further comprise gene profiling the subject, wherein the gene to be profiled is one or more genes selected from the group consisting of ABL1, AKT1, AKT2, ALK, APC, AR, ARID1A, ASXL1, ATM, AURKA, BAP, BAP1, BCL2L11, BCR, BRAF, BRCA1, BRCA2, CCND1, CCND2, CCND3, CCNE1, CDH1, CDK4, CDK6, CDK8, CDKN1A, CDKN1B, CDKN2A, CDKN2B, CEBPA, CTNNB1, DDR2, DNMT3A, E2F3, EGFR, EML4, EPHB2, ERBB2, ERBB3, ESR1, EWSR1, FBXW7, FGF4, FGFR1, FGFR2, FGFR3, FLT3, FRS2, HIF1A, HRAS, IDH1, IDH2, IGF1R, JAK2, KDM6A, KDR, KIF5B, KIT, KRAS, LRP1B, MAP2K1, MAP2K4, MCL1, MDM2, MDM4, MET, MGMT, MLL, MPL, MSH6, MTOR, MYC, NF1, NF2, NKX2-1, NOTCH1, NPM, NRAS, PDGFRA, PIK3CA, PIK3R1, PML, PTEN, PTPRD, RARA, RB1, RET, RICTOR, ROS1, RPTOR, RUNX1, SMAD4, SMARCA4, SOX2, STK11, TET2, TP53, TSC1, TSC2, and VHL.

In certain embodiments, the second agent is everolimus, and subjects present somatic mutations in TSC1.

In some embodiments, this invention provides a method of treating a subpopulation of breast cancer patients wherein said sub-population has increased expression of one or more of the following genes and treating said sub-population with an effective dose of a combination of RAD1901 or solvates (e.g., hydrate) or salts thereof and one or more second therapeutic agent(s) (e.g., everolimus) as described herein according to the dosing embodiments as described in this disclosure.

(6) Dose Adjusting

In addition to establishing the ability of RAD1901 to inhibit tumor growth, the results provided herein show that RAD1901 inhibits estradiol binding to ER in the uterus and pituitary (Example III(A)). In these experiments, estradiol binding to ER in uterine and pituitary tissue was evaluated by FES-PET imaging. After treatment with RAD1901, the observed level of ER binding was at or below background levels. These results establish that the antagonistic effect of RAD1901 on ER activity can be evaluated using real-time scanning. Based on these results, methods are provided herein for monitoring the efficacy of treatment RAD1901 or solvates (e.g., hydrate) or salts thereof in a combination therapy disclosed herein by measuring estradiol-ER binding in one or more target tissues, wherein a decrease or disappearance in binding indicates efficacy.

Further provided are methods of adjusting the dosage of RAD1901 or solvates (e.g., hydrate) or salts thereof in a combination therapy disclosed herein based on estradiol-ER binding. In certain embodiments of these methods, binding is measured at some point following one or more administrations of a first dosage of the compound. If estradiol-ER binding is not affected or exhibits a decrease below a predetermined threshold (e.g., a decrease in binding versus baseline of less than 5%, less than 10%, less than 20%, less than 30%, or less than 50%), the first dosage is deemed to be too low. In certain embodiments, these methods comprise an additional step of administering an increased second dosage of the compound. These steps can be repeated, with dosage repeatedly increased until the desired reduction in estradiol-ER binding is achieved. In certain embodiments, these steps can be incorporated into the methods of inhibiting tumor growth provided herein. In these methods, estradiol-ER binding can serve as a proxy for tumor growth inhibition, or a supplemental means of evaluating growth inhibition. In other embodiments, these methods can be used in conjunction with the administration of RAD1901 or solvates (e.g., hydrate) or salts thereof for purposes other than inhibition of tumor growth, including for example inhibition of cancer cell proliferation.

In certain embodiments, the methods provided herein for adjusting the dosage of a RAD1901 or solvates (e.g., hydrate) or salts thereof in a combination therapy comprise:
(1) administering a first dosage of RAD1901 or solvates (e.g., hydrate) or salts thereof (e.g., about 350 to about 500 mg/day) for 3, 4, 5, 6, or 7 days;
(2) detecting estradiol-ER binding activity, for example using FES-PET imaging as disclosed herein; wherein:
  (i) if the ER binding activity is not detectable or is below a predetermined threshold level, continuing to administer the first dosage (i.e., maintain the dosage level); or
  (ii) if the ER binding activity is detectable or is above a predetermined threshold level, administering a second dosage that is greater than the first dosage (e.g., the first dosage plus about 50 to about 200 mg) for 3, 4, 5, 6, or 7 days, then proceeding to step (3);
(3) detecting estradiol-ER binding activity, for example using FES-PET imaging as disclosed herein; wherein
  (i) if the ER binding activity is not detectable or is below a predetermined threshold level, continuing to administer the second dosage (i.e., maintain the dosage level); or
  (ii) if the ER binding activity is detectable or is above a predetermined threshold level, administering a third dosage that is greater than the second dosage (e.g., the second dosage plus about 50 to about 200 mg) for 3, 4, 5, 6, or 7 days, then proceeding to step (4);
(4) repeating the steps above through a fourth dosage, fifth dosage, etc., until no ER binding activity is detected.

In certain embodiments, the invention includes the use of PET imaging to detect and/or dose ER sensitive or ER resistant cancers.

(7) Combinations for the Methods Disclosed Herein

Another aspect of the invention relates to a pharmaceutical composition comprising one or more RAD1901 or solvates (e.g., hydrate) or salts thereof and/or second therapeutic agent(s) (e.g., everolimus) disclosed herein in a therapeutically effective amount as disclosed herein for the combination methods set forth herein.

RAD1901-ERα Interactions
(1) Mutant ERα in ER Positive Breast Tumor Samples from Patients Who Received at Least One Line of Endocrine Treatment In five studies reported in the past two years, a total of 187 metastatic ER positive breast tumor samples from patients who received at least one line of endocrine treatment were sequenced and ER LBD mutations were identified in 39 patients (21%) (Jeselsohn). Among the 39 patients, the six most frequent LBD mutations are shown in Scheme 1 adapted from Jeselsohn.

Scheme 1. Location of exemplary mutations of ERα and frequencies thereof

Estrogen Receptor

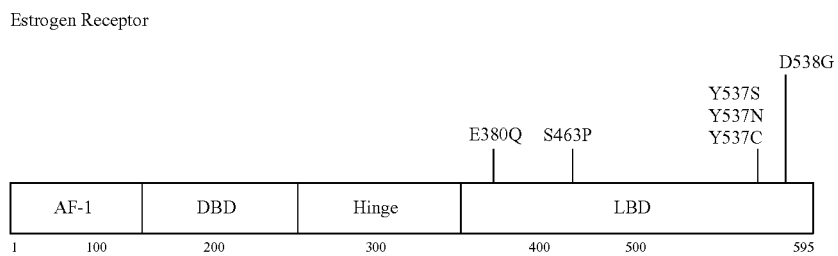

The frequency of all LBD mutations are summarized in Table 9.

Computer modeling showed that RAD1901-ERα interactions are not likely to be affected by mutants of LBD of ERα, e.g., Y537X mutant wherein X was S, N, or C; D538G; and S463P, which account for about 81.7% of LBD mutations found in a recent study of metastatic ER positive breast tumor samples from patients who received at least one line of endocrine treatment (Table 10, Example V).

Provided herein are complexes and crystals of RAD1901 bound to ERα and/or a mutant ERα, the mutant ERα comprises one or more mutations including, but not limited to, Y537$X_1$ wherein $X_1$ is S, N, or C, D538G, L536$X_2$ wherein $X_2$ is R or Q, P535H, V534E, S463P, V392I, E380Q and combinations thereof.

In certain embodiments of the methods provided herein, the LBD of ERα and a mutant ERα comprises AF-2. In other embodiments, the LBD comprises, consists of, or consists essentially of amino acids 299-554 of ERα. In certain embodiments, the LBD of the mutant ERα comprises one or more mutations including, but not limited to, Y537$X_1$ wherein $X_1$ is S, N, or C, D538G, L536$X_2$ wherein $X_2$ is R or Q, P535H, V534E, S463P, V392I, E380Q and combinations thereof. The term "and/or" as used herein includes both the "and" case and the "or" case.

Provided herein in certain embodiments are methods of treating a condition associated with ERα and/or a mutant ERα activity or expression in a subject in need thereof comprising administering to the subject a combination of one or more second therapeutic agent(s) (e.g., everolimus) and one or more compounds capable of binding to ERα and/or a mutant ERα via LBD. In certain embodiments, the subject is a mammal, and in certain of these embodiments the subject is human. In certain embodiments, the condition is tumor and/or cancer, including but not limited to ER positive tumor and/or cancer as disclosed herein.

In certain embodiments of the compounds and methods provided herein, the LBD of ERα and a mutant ERα comprises AF-2. In other embodiments, the LBD comprises, consists of, or consists essentially of amino acids 299-554 of ERα. In certain embodiments, the LBD of the mutant ERα comprises one or more mutations including, but not limited to, Y537$X_1$ wherein $X_1$ is S, N, or C, D538G, L536$X_2$ wherein $X_2$ is R or Q, P535H, V534E, S463P, V392I, E380Q and combinations thereof.

In certain embodiments of the compounds and methods provided herein, the compound capable of binding to ERα and/or mutant ERα via LBD is a selective estrogen receptor degrader (SERD) or selective estrogen receptor modulator (SERM). In certain embodiments, the compound capable of binding to ERα and/or mutant ERα via LBD does so via one or more interactions selected from the group consisting of H-bond interactions with residues E353, D351, R349, and/or L536 and pi-interactions with residue F404 of ERα and/or mutant ERα. One example of such a compound is RAD1901.

Provided herein in certain embodiments are methods of treating a condition associated with activity or expression of a mutant ERα comprising one or more mutations including, but not limited to, Y537$X_1$ wherein $X_1$ is S, N, or C, D538G, L536$X_2$ wherein $X_2$ is R or Q, P535H, V534E, S463P, V392I, E380Q and combinations thereof, wherein the method comprises administering to the subject a combination of one or more second therapeutic agent(s) (e.g., everolimus) and one or more compounds capable of binding to ERα via the LBD. In certain embodiments, the condition is cancer, including but not limited to ER positive cancer, breast cancer, ER positive breast cancer, and metastatic breast cancer, and in certain embodiments the compound is RAD1901 or a pharmaceutically acceptable solvate (e.g., hydrate) or pharmaceutically acceptable salt thereof.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Materials and Methods
Test Compounds
RAD1901 used in the examples below was (6R)-6-(2-(N-(4-(2-(ethylamino)ethyl)benzyl)-N-ethylamino)-4-methoxyphenyl)-5,6,7,8-tetrahydronaphthalen-2-ol dihydrochloride, manufactured by IRIX Pharmaceuticals, Inc. (Florence, SC). RAD1901 was stored as a dry powder, formulated for use as a homogenous suspension in 0.5% (w/v) methylcellulose in deionized water, and for animal models was administered by oral gavage. Tamoxifen, raloxifene and estradiol (E2) were obtained from Sigma-Aldrich (St. Louis, MO), and administered by subcutaneous injection. Fulvestrant was obtained from Tocris Biosciences (Minneapolis, MN) and administered by subcutaneous injection. Other laboratory reagents were purchased from Sigma-Aldrich unless otherwise noted.

Cell Lines

MCF-7 cells (human mammary metastatic adenocarcinoma) were purchased from American Type Culture Collection (Rockville, MD) and were routinely maintained in phenol red-free minimal essential medium (MEM) containing 2 mM L-glutamine and Earle's BSS, 0.1 mM nonessential amino acids and 1 mM sodium pyruvate supplemented with 0.01 mg/ml bovine insulin and 10% fetal bovine serum (Invitrogen, Carlsbad, CA), at 5% $CO_2$.

T47D cells were cultured in 5% $CO_2$ incubator in 10 cm dishes to approximately 75% confluence in RPMI growth media supplemented with 10% FBS and 5 µg/mL human insulin.

In Vivo Xenograft Models

All mice were housed in pathogen-free housing in individually ventilated cages with sterilized and dust-free bedding cobs, access to sterilized food and water ad libitum, under a light dark cycle (12-14 hour circadian cycle of artificial light) and controlled room temperature and humidity. Tumors were measured twice weekly with Vernier calipers and volumes were calculated using the formula: $(L*W^2)*0.52$.

PDx Models

Some examples of patient-derived xenograft models (PDx models) are shown in FIG. 1. PDx models with patient derived breast cancer tumor were established from viable human tumor tissue or fluid that had been serially passaged in animals (athymic nude mice (Nu (NCF)-Foxn1nu)) a limited number of times to maintain tumor heterogeneity. Pre-study tumor volumes were recorded for each experiment beginning approximately one week prior to its estimated start date. When tumors reached the appropriate Tumor Volume Initiation (TVI) range (150-250 $mm^3$), animals were randomized into treatment and control groups and dosing initiated (Day 0, 8-10 subjects in each group); animals in all studies followed individually throughout each experiment. Initial dosing began Day 0; animals in all groups were dosed by weight (0.01 mL per gram; 10 ml/kg). Each group was treated with vehicle (control, p.o./QD to the endpoint), tamoxifen (1 mg/subject, s.c./QOD to the end point), fulvestrant (Faslodex®; 1 mg/subject or 3 mg/subject as needed, SC/weekly×5 and extended if necessary), or RAD1901 (30, 60 or 120 mg/kg of the subject, p.o./QD to the endpoint) as specified from day 0. The treatment period lasted for 56-60 days depending on the models. The drinking water for these PDx models was supplemented with 17β-estradiol.

Agent Efficacy

For all studies, beginning Day 0, tumor dimensions were measured by digital caliper and data including individual and mean estimated tumor volumes (Mean TV±SEM) recorded for each group; tumor volume was calculated using the formula (Yasui et al. Invasion Metastasis 17:259-269 (1997), which is incorporated herein by reference): TV=$width^2$×length×0.52. Each group or study was ended once the estimated group mean tumor volume reached the Tumor Volume (TV) endpoint (time endpoint was 60 days; and volume endpoint was group mean 2 $cm^3$); individual mice reaching a tumor volume of 2 $cm^3$ or more were removed from the study and the final measurement included in the group mean until the mean reached volume endpoint or the study reached time endpoint.

Efficacy Calculations and Statistical Analysis

% Tumor Growth Inhibition (% TGI) values were calculated at a single time point (when the control group reached tumor volume or time endpoint) and reported for each treatment group (T) versus control (C) using initial (i) and final (f) tumor measurements by the formula (Corbett T H et al. In vivo methods for screening and preclinical testing. In: Teicher B, ed., Anticancer Drug Development Guide. Totowa, NJ: Humana. 2004: 99-123): % TGI=1−Tf−Ti/Cf−Ci.

Statistics

TGI Studies—One way ANOVA+Dunnett's Multiple Comparisons Test (Corbett T H et al).

Sample Collection

At endpoint, tumors were removed. One fragment was flash frozen, while another fragment was placed in 10% NBF for at least 24 hours and formalin fixed paraffin embedded (FFPE). Flash frozen samples were stored at −80° C.; FFPE blocks were stored at room temperature.

Western Blot

Cells were harvested and protein expression was analyzed using standard practice. Tumors were harvested at the indicated time points after the last day of dosing, homogenized in RIPA buffer with protease and phosphatase inhibitors using a Tissuelyser (Qiagen). Equal amounts of protein were separated by MW, transferred to nitrocellulose membranes and blotted with the following antibodies using standard practice:

Estrogen receptor (Santa Cruz (HC-20); sc-543)
Progesterone receptor (Cell Signaling Technologies; 3153)
Vinculin (Sigma-Aldrich, v9131)

qPCR analyses were performed as follows: Cells were harvested, mRNA was extracted, and equal amounts used for cDNA synthesis and qPCR with primers specific for progesterone receptor, GREB1, and TFF1 (LifeTech). Bands were quantified using 1D Quant software (GE).

Immunohistochemistry

Tumors were harvested, formalin-fixed and embedded into paraffin. Embedded tumors were sectioned (6 µM) and stained with antibodies specific for ER, PR, and Her2. Quantitation was performed as follows: Five fields were counted for positive cells (0-100%) and intensity of staining (0-3+). H-scores (0-300) were calculated using the following formula: % positivity*intensity.

Example I. RAD1901-Everolimus Combinations Provided Enhanced Tumor Growth Inhibition in Tumor and/or Cancer Expressing WT ER or Mutant ER (e.g., Y537S), with Different Prior Endocrine Therapy I(A). Effectiveness of RAD1901 on Animal Xenografts Models I(A)(i) RAD1901 Inhibited Tumor Growth in PDx Models (PDx-1 to PDx-12) Regardless of ER Status and Prior Endocrine Therapy FIG. 1 demonstrates tumor growth inhibition effects in various PDx models for mice treated with RAD1901 alone. Twelve patient-derived xenograft models were screened to test RAD1901 response in a variety of genetic backgrounds with varied levels of ER, PR and Her2. Full efficacy study was carried out for PDx models marked with "*" (PDx-1 to PDx-4, and PDx-12), with n=8-10. Screen study was carried out for other PDx models (PDx-5 to PDx-11), with n=3. The PDx models were treated with vehicle (negative control) or RAD1901 at a dosage of 60 mg/kg for 60 days p.o., q.d. As demonstrated in FIG. 1, PDx models in which the growth was driven by ER and an additional driver (e.g., PR+ and/or Her2+) benefited from the RAD1901 treatments. RAD1901 was efficacious in inhibiting tumor growth in models with ER mutations and/or high level expression of Her2 (PDx), regardless of prior treatment, either treatment naïve (Rx-naïve), or treated with aromatase inhibitor, tamoxifen (tam), chemotherapy (chemo), Her2 inhibitors (Her2i, e.g., trastuzumab, lapatinib), bevacizumab, fulvestrant, and/or rituximab.

I(A)(ii) RAD1901-Everolimus Combination Drove More Regression than RAD1901 Alone in Xenograft Models Expressing WT ER I(A)(ii)(1) RAD1901-Everolimus Drove More Regression than RAD1901 Alone in MCF-7 Xenografts that were Responsive to Fulvestrant Treatments.

MCF-7 Xenograft Model

Two days before cell implantation, Balb/C-Nude mice were inoculated with 0.18/90-day release 17β-estradiol pellets. MCF-7 cells (PR+, Her2−) were harvested and 1×10$^7$ cells were implanted subcutaneously in the right flank of Balb/C-Nude mice. When the tumors reached an average of 200 mm$^3$, the mice were randomized into treatment groups by tumor volume and treated with the test compounds. Each group was treated with vehicle (control, p.o., q.d., to the endpoint), fulvestrant (Faslodex®; 3 mg/subject, s.c., qwk×5 and extended if necessary), RAD1901 (30 mg/kg or 60 mg/kg of the subject, p.o., q.d., to the endpoint), everolimus (2.5 mg/kg, p.o., to the end point), or RAD1901-everolimus combination at doses specified from day 0. The treatment period lasted for 28 days.

MCF-7 xenograft mice were treated with vehicle (negative control), RAD1901 (60 mg/kg, PO daily), everolimus (2.5 mg/kg, p.o.), a combination of RAD1901 (30 or 60 mg/kg, PO daily) and everolimus (2.5 mg/kg, p.o.), fulvestrant (3 mg/dose, s.c., weekly) or a combination of fulvestrant (3 mg/dose, s.c., weekly) and everolimus (2.5 mg/kg, p.o.). Tumor size was measured at various time points for 27 days.

Results are shown in FIGS. 2A-2B. Treatment with the combination of RAD1901 (60 mg/kg) and everolimus (2.5 mg/kg), once again resulted in significant tumor regression, with superior results to treatment with RAD1901, everolimus, or fulvestrant alone, or with a combination of fulvestrant and everolimus (FIG. 2B).

FIG. 2C demonstrates that RAD1901-everolimus combinations with RAD1901 at a dose of 30 mg/kg or 60 mg/kg both provided similar effects, although RAD1901 alone at 30 mg/kg was not as effective as RAD1901 alone at 60 mg/kg in inhibiting tumor growth. Said results suggest a RAD1901-everolimus combination with a lower dose of RAD1901 (e.g., 30 mg/kg) was sufficient to maximize the tumor growth inhibition/tumor regression effects in said xenograft models.

Treatment with the combination of RAD1901 and everolimus was also more effective at decreasing ER and PR expression in vivo in the MCF-7 xenograft models than treatment with RAD1901, everolimus, or fulvestrant alone, or treatment with a combination of fulvestrant and everolimus (FIG. 11); tumors harvested two hours after the last dosing).

I(A)(ii)(2) RAD1901-Everolimus Drove More Regression than RAD1901 Alone in PDx-11 and PDx-2 Models that were Responsive to Fulvestrant Treatments.

ER WT PDx models PDx-2 (PR+, Her2+, treatment naïve) and PDx-11 (PR+, Her2+, treated with AI, fulvestrant and chemo) exhibited different sensitivities to fulvestrant (3 mg/dose, qwk, s.c.). PDx-2 and PDx-11 models were treated with a combination of RAD1901 (60 mg/kg, q.d., p.o.) and everolimus (2.5 mg/kg, p.o.), RAD1901 alone (60 mg/kg, q.d., p.o.), everolimus alone (2.5 mg/kg, p.o.), or fulvestrant alone (3 mg/dose, qwk, s.c.).

In PDx-11 models, administration of fulvestrant or everolimus alone significantly inhibited tumor growth, with fulvestrant treated mice exhibiting better effects in tumor growth inhibition. Fulvestrant treatment exhibited slight tumor regression (FIG. 3B). Unexpectedly, administration of RAD1901 alone or in combination with everolimus resulted in a significant tumor regression, with the combination achieved even more significant tumor regression effects in the wild-type ESR1 PDx models (FIG. 3B).

In PDx-2 models, oral administration of RAD1901 alone achieved better effects of inhibiting tumor growth comparing to injection of fulvestrant alone (FIG. 4A). Furthermore, administration of RAD1901 or everolimus alone significantly inhibited tumor growth. Unexpectedly, administration of RAD1901 in combination with everolimus resulted in even more enhanced effect in inhibiting tumor growth (FIG. 4B).

Furthermore, in PDx-4 model that were responsive to fulvestrant treatment (1 mg/dose, s.c., qwk), RAD1901-mediated tumor growth inhibition was maintained in the absence of treatment at least two months after RAD1901 treatment (30 mg/kg, p.o., q.d.) period ended, while estradiol treatment continued (FIG. 5).

Thus, a combination of one or more second therapeutic agent (s) with RAD1901 is likely to benefit a patient in inhibiting tumor growth after treatment ends, especially when the one or more second therapeutic agent (s) (e.g., everolimus) can be reduced or delayed for adverse reactions. http://www.fda.gov/Drugs/InformationOnDrugs/ApprovedDrugs/ucm488028.htm.

I(A)(iii) RAD1901-Everolimus Drove More Regression than RAD1901 Alone in Xenograft Models Expressing Mutant ER (ERα Y537S)

I(A)(iii)(1) RAD1901-Everolimus Drove More Regression than RAD1901 Alone in PDx-5 Models that were Hardly Responsive to Fulvestrant Treatments.

PDx-5 models were prepared following similar protocol as described supra for PDx models. The tumor sizes of each dosing group were measured twice weekly with Vernier calipers, and volumes were calculated using the formula (L*W2)*0.52.

Inhibition of tumor growth by RAD1901 (60 mg/kg, q.d., p.o.), everolimus (2.5 mg/kg, p.o.), and RAD1901 (60 mg/kg, q.d., p.o.) in combination with everolimus (2.5 mg/kg, p.o.) in PDx-5 models (PDx models with patient-derived breast cancer tumor having the Y537S estrogen receptor mutation, PR+, Her2+, prior treatment with aromatase inhibitor) was assessed using the method described herein. For tumors expressing certain ERα mutations (e.g., Y537S), combination treatment of RAD1901 and everolimus was more effective in inhibiting tumor growth than treatment with either agent alone (FIG. 6B). These PDx models were hardly responsive to fulvestrant (3 mg/dose). Combination treatment of RAD1901 and everolimus was more effective than treatment with either agent alone in inhibiting tumor growth in the PDx-5 models (FIG. 6B).

Thus, the results showed that RAD1901 was an effective endocrine backbone that potentiated the tumor growth inhibition of targeted agents. Furthermore, RAD1901 showed potent anti-tumor activity in PDx models derived from patients that have had multiple prior endocrine therapies including those that are insensitive to fulvestrant.

I(A)(iv) Pharmacokinetic Evaluation of Fulvestrant Treatments to Non-Tumor Bearing Mice.

Various doses of fulvestrant were administered to mice and demonstrated significant dose exposure to the subjects (FIG. 7).

Fulvestrant was administered at 1, 3, or 5 mg/dose subcutaneously to nude mice on day 1 (D1 Rx) and day 8 (D8 Rx, n=4/dose level). Blood was collected at the indicated time points for up to 168 hours after the second dose, centrifuged, and plasma was analyzed by Liquid Chromatography-Mass Spectrometry.

I(B) RAD1901 Promoted Survival in a Mouse Xenograft Model of Brain Metastasis (MCF-7 Intracranial Models).

The potential ability of RAD1901 to cross the blood-brain barrier and inhibit tumor growth was further evaluated using an MCF-7 intracranial tumor xenograft model.

Female athymic nude mice (Crl:NU(NCr)-Foxn1nu) were used for tumor xenograft studies. Three days prior to tumor cell implantation, estrogen pellets (0.36 mg E2, 60-day release, Innovative Research of America, Sarasota, FL) were implanted subcutaneously between the scapulae of all test animals using a sterilized trochar. MCF-7 human breast adenocarcinoma cells were cultured to mid-log phase in RPMI-1640 medium containing 10% fetal bovine serum, 100 units/mL penicillin G, 100 µg/mL streptomycin sulfate, 2 mM glutamine, 10 mM HEPES, 0.075% sodium bicarbonate and 25 g/mL gentamicin. On the day of tumor cell implant, the cells were trypsinized, pelleted, and resuspended in phosphate buffered saline at a concentration of $5 \times 10^7$ cells/mL. Each test mouse received $1 \times 10^6$ MCF-7 cells implanted intracranially.

Five days after tumor cell implantation (designated as day 1 of the study), mice were randomized into three groups of 12 animals each and treated with vehicle, fulvestrant (0.5 mg/animal daily), or RAD1901 (120 mg/kg daily), as described above.

The endpoint was defined as a mortality or 3× survival of the control group, whichever comes first. Treatment tolerability was assessed by body weight measurements and frequent observation for clinical signs of treatment-related adverse effects. Animals with weight loss exceeding 30% for one measurement, or exceeding 25% for three measurements, were humanely euthanized and classified as a treatment-related death. Acceptable toxicity was defined as a group-mean body weight loss of less than 20% during the study and not more than one treatment-related death among ten treated animals, or 10%. At the end of study animals were euthanized by terminal cardiac puncture under isoflurane anesthesia. RAD1901 and fulvestrant concentration in plasma and tumor were determined using LC-MS/MS.

Kaplan Meier survival analysis demonstrated that RAD1901 significantly prolonged survival compared to fulvestrant (P<0.0001; FIG. 8). No animals in the control or fulvestrant group survived beyond day 20 and day 34 respectively, whereas 41% (5/12) of the RAD1901 treated animals survived until the end of the study on day 54.

Concentration of RAD1901 in the plasma was 738±471 ng/mL and in the intracranial tumor was 462±105 ng/g supporting the hypothesis that RAD1901 is able to effectively cross the blood-brain barrier. In contrast, concentrations of fulvestrant were substantially lower in the plasma (21±10 ng/mL) and in the intracranial tumor (8.3±0.8 ng/g).

I(C). Phase 1 Study of RAD1901 Treatment for ER+ Advanced Breast Cancer.

In the phase 1 study, safety, tolerability and pharmacokinetics were evaluated in 44 healthy postmenopausal females. No dose limiting toxicities were observed, maximum tolerated dose (MTD) was not established. Plasma exposure increased more than dose proportionally over the dose range tested.

Subjects 8 postmenopausal females with advanced adenocarcinoma of the breast (ER+ tumor with no less than 1% staining by IHC, HER2-negative tumor with ECOG performance status of 0 or 1) were enrolled as subjects for this phase 1 study. The subjects must have received the following prior treatments:
- no greater than 2 prior chemotherapy regimens in the advanced/metastatic setting
- 6 months prior endocrine therapy and had progressed on prior endocrine therapy Subjects with untreated or symptomatic CNS metastases or prior anticancer treatment within the following windows were excluded:
- Tamoxifen<14 days before _first dose study treatment
- Fulvestrant<90 days before _first dose study treatment
- Chemotherapy<28 days before _first dose study treatment
- LHRH analogue<12 months before _first dose study treatment DLT Criteria
- Any Grade no less than 3 non-hematologic toxicity (excluding alopecia and nausea, vomiting or diarrhea that has not been treated with optimal medication)
- Any Grade no less than 3 hematologic toxicity
- Any grade toxicity that leads to study drug interruption for >7 days
- Dose limiting toxicity observation period is day 1-28 of Cycle 1

Treatment Emergent Adverse Events (TEAEs)

TEAEs were recorded throughout the study. Preliminary data are summarized in Table 12. "n" is number of subjects with at least one treatment-related AE in a given category, AEs graded as per the Common Terminology Criteria for Adverse Events (CTCAE) v4.0, and any patient with multiple scenarios of a same preferred term was counted only once to the most severe grade. No death or dose limiting toxicities were observed, maximum tolerated dose (MTD) was not established. Most AEs were grade 1 or 2. Most common treatment-related AEs were dyspepsia (5/8 patients) and nausea (3/8 patients). Two serious AEs (SAEs) were observed, one a grade 3 treatment-related constipation, and the other shortness of breath (pleural effusion) not related to the treatment.

The heavily pretreated subjects of this phase 1 study included subjects previously treated with multiple endocrine and targeted agents, e.g., CDK4/6, PI3K and mTOR inhibitors. No dose limiting toxicities were observed after RAD1901 treatment at 200 mg daily oral dose up to 6 months, and at 400 mg daily oral dose up to two months. Thus, RAD1901 showed potential for treating ER+ advanced breast cancer, especially in subjects previously treated with endocrine and/or targeted agents such as CDK4/6, PI3K and mTOR inhibitors.

Example II. RAD1901 Preferably Accumulated in Tumor and could be Delivered to Brain MCF-7 xenografts as described in Example I(A)(i) were further evaluated for RAD1901 concentration in plasma and tumor using LC-MS/MS. At the end of study, the concentration of RAD1901 in plasma was 344±117 ng/mL and in tumor in 11,118±3,801 ng/mL for the 60 mg/kg dose level. A similar tumor to plasma ratio was also observed at lower dose levels where tumor concentrations were approximately 20-30 fold higher than in plasma. RAD1901 levels in plasma, tumor, and brain for mice treated for 40 days are summarized in Table 1. A significant amount of RAD1901 was delivered to the brain of the treated mice (e.g., see the B/P ratio (RAD1901 concentration in brain/the RAD1901 concentration in plasma)), indicating that RAD1901 was able to cross the blood-brain barrier (BBB). Unexpectedly, RAD1901 preferably accumulated in the tumor. See, e.g., the T/P (RAD1901 concentration in tumor/RAD1901 concentration in plasma) ratio shown in Table 1.

Example III. RAD1901 Inhibited ER Pathway and Degraded ER

III(A). RAD1901 Decreased ER-Engagements in Uterus and Pituitary in Healthy Postmenopausal Female Human Subjects.

The subjects had an amenorrhea duration of at least 12 months and serum FSH consistent with menopause. The subjects were 40-75 years old with BMI of 18.0-30 kg/m$^2$. Subjects had intact uterus. Subjects having evidence of clinically relevant pathology, increased risk of stroke or of history venous thromboembolic events, or use of concomitant medication less than 14 days prior to admission to clinical research center (paracetamol allowed up to 3 days prior) were excluded.

FES-PET was performed at baseline and after 6 days of exposure to RAD1901 to evaluate ER engagement in the uterus. RAD1901 occupied 83% and 92% of ER in the uterus at the 200 mg (7 subjects) and 500 mg (6 subjects) dose levels, respectively.

FES-PET imaging showed significant reduction in binding of labelled-estradiol to both the uterus and pituitary after RAD1901 treatment with 200 mg or 500 mg (once/day, p.o., 6 days).

Due to the high ER expression, the uterus showed a strong FES-PET signal at baseline before RAD1901 treatment (FIG. 9A, baseline transversal view for uterus FES-PET scan of Subject 3 treated with 200 mg dose level; FIG. 9B, baseline sagittal view and transversal view for uterus FES-PET scan respectively of Subject 7 treated with 500 mg dose level). However, when scanned four hours post dosing on day 6 in the study, the uterus was hardly visible (at or close to background FES-PET signal (FIG. 9A, Day 6 transversal view for uterus scan of Subject 3; and FIG. 9B, Day 6 sagittal view and transversal view for uterus scan respectively of Subject 7). Such data were consistent with ER degradation and/or competition for the binding to the receptor. FIGS. 9A and 9B also include CT scan of the uterus scanned by FES-PET showing the existence of the uterus before and after RAD1901 treatment.

The FES-PET uterus scan results were further quantified to show the change of post-dose ER-binding from baseline for 7 subjects (FIG. 9C), showing Subjects 1-3 and Subjects 4-7 as examples of the 200 mg dose group and 500 mg dose group, respectively. RAD1901 showed robust ER engagement at the lower dose level (200 mg).

FIGS. 10A-B showed a representative image of FES-PET scan of the uterus (A) and pituitary (B) before (Baseline) and after (Post-treatment) RAD1901 treatment at 500 mg p.o. once a day, after six days. FIG. 10A showed the FES-PET scan of the uterus by (a) Lateral cross-section; (b) longitude cross-section; and (c) longitude cross-section.

The subject's post dose FES-PET scan of uterus and pituitary showed no noticeable signal of ER binding at uterus (FIG. 10A, Post-treatment) and at pituitary (FIG. 10B, Post-treatment), respectively.

Thus, the results showed that RAD1901 effectively degraded/deactivated ER in human at a dosage of 200 and 500 mg PO once/day, after six days.

Standard uptake value (SUV) for uterus, muscle and bone were calculated and summarized for RAD1901 treatments at 200 mg and 500 mg p.o. daily in Tables 2 and 3, respectively. Post-dose uterine signals were a tor close to levels from "non-target tissues," suggesting a complete attenuation of FES-PET uptake post RAD1901 treatment. Almost no change was observed in pre- versus post-treatment PET scans in tissues that did not significant express estrogen receptor.

Thus, RAD1901 or salt or solvate (e.g., hydrate) thereof may be used in treating cancer and/or tumor cells having overexpression of ER (e.g., breast cancer, uterus cancer, and ovary cancer), without negative effects to other organs (e.g. bones, muscles). RAD1901 or salt or solvate (e.g., hydrate) thereof may be especially useful in treating metastatic cancers and/or tumors having overexpression of ER in other organs, e.g., the original breast cancer, uterus cancer, and/or ovary cancer migrated to other organs (e.g., bones, muscles), to treat breast cancer, uterus cancer, and/or ovary cancer lesions in other organs (e.g., bones, muscles), without negative effect to said organs.

III(B). RAD1901 Decreased ER Expression and Inhibited ER Pathway.

III(B)(i)(1) RAD1901-Everolimus Combo was More Effective in Decreasing ER and PR Expression in MCF-7 Xenograft Models and Treatment with RAD1901, Everolimus or Fulvestrant Alone, or a Ful-Everolimus Combination.

Treatment with the combination of RAD1901 and everolimus was also more effective at decreasing ER and PR expression in vivo in the MCF-7 xenograft models (as described in Example I(A)(ii)) than treatment with RAD1901, everolimus, or fulvestrant alone, or treatment with a combination of fulvestrant and everolimus (FIG. 11); tumors harvested two hours after the last dosing).

III(B)(i)(2) Comparison of RAD1901 and Fulvestrant in MCF-7 and T47D Cell Lines.

The effects of RAD1901 and fulvestrant were compared using MCF-7 and T47D cell lines, both are human breast cancer cell lines, at various concentrations, 0.01 μM, 0.1 μM and 1 μM (FIG. 12A for MCF-7 cell line assays; and FIG. 12B for T47D cell lines). Three ER target genes, progesterone receptor (PgR), growth regulation by estrogen in breast cancer 1 (GREB1) and trefoil factor 1 (TFF1), were used as markers. RAD1901 caused nearly complete ER degradation and inhibited ER signaling (FIGS. 12A-B). Especially for MCF-7 cell lines, fulvestrant showed comparable or even slightly higher efficacies in inhibiting ER signaling when administered at the same concentration. Unexpectedly, RAD1901 was comparable or more effective than fulvestrant in inhibiting tumor growth, and driving tumor regression as disclosed supra in Example I(A) and Example I(B).

III(B)(i)(3) RAD1901 Treatment Resulted in ER Degradation and Abrogation of ER Signaling in MCF-7 Xenograft Model—Described Supra in Example I(A)(ii)(1).

RAD1901 treatment resulted in ER degradation in vivo (FIGS. 13A and 13B, student's t-test: *p-value<0.05, **p- value<0.01) and inhibited of ER signaling in vivo (FIGS. 13A and 13C, student's t-test: *p-value<0.05, **p-value<0.01).

Tumor harvested from MCF-7 xenograft 2 hours after the final dose of RAD1901 (30 mg/kg, 60 mg/kg, p.o., q.d.) or fulvestrant (3 mg/dose, s.c., qwk) showed significantly decreased ER and PR expression (FIGS. 13A-B). Tumor harvested from MCF-7 xenograft 8 hours after the final dose of fulvestrant treatment showed increased PR and ER expression. However, tumor harvested from MCF-7 xenograft 8 hours after the final dose of RAD1901 treatment showed reduced PR and ER expression (FIGS. 13A and 13C).

Tumor harvested from MCF-7 xenograft 8 hours or 12 hours after the single dose of RAD1901 (30 mg/kg, 60 mg/kg, or 90 mg/kg, p.o., q.d.) showed rapidly decreased PR expression (FIGS. 14A-C). Tumor harvested from MCF-7 xenograft 4 hours or 24 hours after the 7th dose of RAD1901 (30 mg/kg, 60 mg/kg, or 90 mg/kg, p.o., q.d.) showed consistent and stable inhibition of ER signaling (FIG. 14B). Quantification of western blot analyses of tumor harvested from MCF-7 xenograft at various time points during the treatment of RAD1901 (30 mg/kg, 60 mg/kg, or 90 mg/kg, p.o., q.d.) showed a dose-dependent decrease in PR (FIG. 14C).

RAD1901 treatment caused a rapid decrease in proliferation in MCF-7 xenograft models. For example, tumor harvested from MCF-7 xenograft models 8 hours after the single dose of RAD1901 (90 mg/kg, p.o., q.d.) and 24 hours after the 4th dose of RAD1901 (90 mg/kg, p.o., q.d.) were sectioned and stained to show a rapid decrease of the proliferation marker Ki67 (FIGS. 15A and 15B).

These results suggest that RAD1901 treatment results in ER degradation and inhibition of ER signaling in ER WT xenografts in vivo.

III(B)(i)(4) RAD1901 Treatment Resulted in ER Degradation and Abrogation of ER Signaling in PDx-4 Models Described Supra in Example I(A)(ii).

RAD1901 treatment caused a rapid decrease in proliferation in the PDx-4 models. For example, four hours after the final dose on the last day of a 56 day efficacy study, tumor harvested from PDx-4 models treated with RAD1901 (30, 60, or 120 mg/kg, p.o., q.d.) or fulvestrant (1 mg/animal, qwk) were sectioned and showed a rapid decrease of the proliferation marker Ki67 compared to PDx-4 models treated with fulvestrant (FIG. 16).

These results suggest that RAD1901 treatment results in ER degradation and inhibition of ER signaling in ER WT xenografts in vivo.

III(B)(ii) RAD1901 Treatment Resulted in Decreased ER Signaling in a Mutant ER PDx-5 Models Described Supra in Example I(A)(iii)(1).

Tumors were harvested at the indicated time points after the last day of dosing (unless otherwise specified), homogenized in RIPA buffer with protease and phosphatase inhibitors using a Tissuelyser (Qiagen). Equal amounts of protein were separated by MW, transferred to nitrocellulose membranes and blotted with the following antibody as described in the Materials and methods section: progesterone receptor (PR, Cell Signaling Technologies; 3153).

Bands were quantified using 1D Quant software (GE), and PR IHC Allred scores obtained from PDx-5 models as described in Example I(A)(iii)(1) are shown in FIG. 17. Fulvestrant exerted little influence to PR expression, while RAD1901 showed efficacy at dosages of both 60 mg/kg and 120 mg/kg (q.d., p.o., FIG. 17).

These results indicate that for tumors expressing certain ERα mutations (e.g., Y537S), RAD1901 was more effective than fulvestrant at inhibiting the tumor growth, especially effective in inhibiting the growth of tumors which were hardly responsive to fulvestrant treatment (e.g., at a dosage of 3 mg/dose, qwk, s.c., FIG. 6A PDx-5). Furthermore, for the tumors which did not respond well to fulvestrant treatment (e.g., PDx-5), RAD1901 was effective in reducing PR expression in vivo, while fulvestrant was not (FIG. 17).

Example IV Impact of RAD1901 Treatment to Uterine Tissue and/or BMD

IV(A)(1): RAD1901 Antagonized Estradiol Stimulation of Uterine Tissue.

The uterotropic effects of RAD1901 were investigated by assessing changes in uterine weight, histology, and C3 gene expression in immature rats. Results from a representative study are shown in FIGS. 18A-D.

Assessment of Uterotropic Activity

Sprague-Dawley rat pups were weaned at 19 days of age, randomized into groups (n=4), and administered vehicle (aqueous methylcellulose), E2 (0.01 mg/kg), raloxifene (3 mg/kg), tamoxifen (1 mg/kg), RAD1901 alone (0.3 to 100 mg/kg), or RAD1901 (0.01 to 10 mg/kg) in combination with E2 (0.01 mg/kg), either by subcutaneous injection or by oral gavage as appropriate (see reagents, above) once daily for 3 consecutive days. Twenty-four hours after the final dose, all animals were euthanized by carbon dioxide inhalation. Body weights and wet uterine weights were recorded for each animal. Similar assays were also conducted with RAD1901 (0.03 to 100 mg/kg) in rats and mice (Charles River Laboratories, Montreal, QC).

Fresh uterine tissue from each rat was fixed in 4% paraformaldehyde, dehydrated with ethanol, and embedded into JB4 plastic resin. Sections were cut at 8 m and stained with 0.1% Toluidine Blue O. Thickness of the endometrial epithelium was measured using a Zeiss Axioskop 40 microscope using the Spot Advanced program; the mean of 9 measurements per specimen was calculated.

Uterine Complement Component 3 (C3) Gene Expression

To determine relative expression levels of C3 in the treated uterine tissue, RNA was extracted from the remaining tissue using the Micro to Midi Total RNA Purification Kit (Invitrogen, Carlsbad, CA) according to the manufacturer's instructions. RNA was quantified, and equal amounts were reverse-transcribed using the High Capacity cDNA Archive Kit (Applied Biosystems, Foster City, CA).

Quantitative PCR was performed using the ABI Prism 7300 System (Applied Biosystems). PCR was done using the Taqman Universal Master Mix with probe sets for C3 and for the 18S ribosomal RNA as a reference gene. Thermal cycling conditions comprised an initial denaturation step at 95° C. for 10 min, followed by 40 cycles at 95° C. for 15 second and 60° C. for 1 minute.

Relative gene expression was determined by normalizing each sample to the endogenous control (18S) and comparing with a calibrator (vehicle). Relative gene expression was determined using the following equation: 2−ΔΔCt (where Ct=cycle threshold or the cycle number at which PCR product was first detected, ΔCt=normalized sample value, and ΔΔCt=normalized difference between dosed subjects and the vehicle). Five replicate gene expression determinations were conducted for each dose, within each study.

Figure 18A:
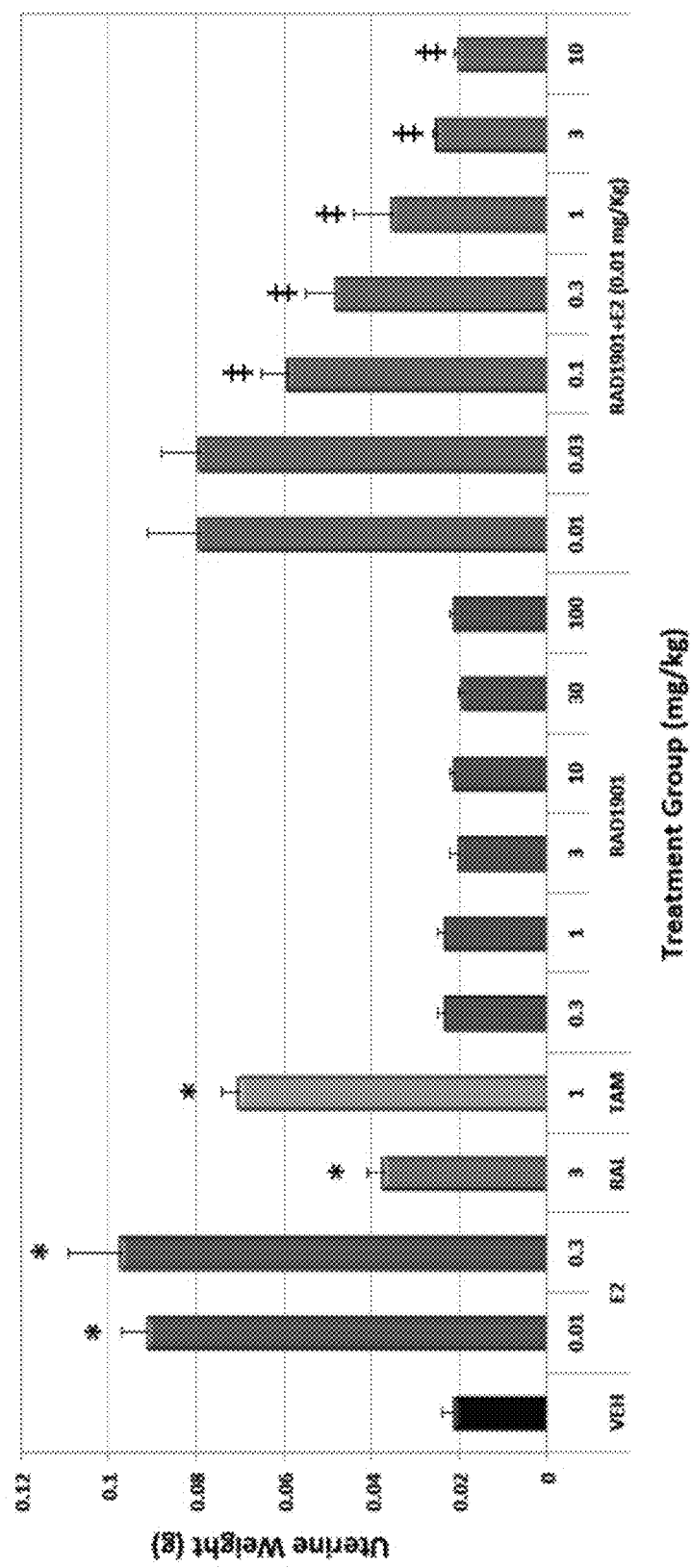

Treatment with E2 (0.01 mg/kg), raloxifene (RAL, 3 mg/kg) or tamoxifen (TAM, 1 mg/kg) resulted in significant increases in uterine wet weight compared to vehicle alone, whereas RAD1901 treatment at a range of doses between 0.3 and 100 mg/kg did not significantly affect uterine wet weight (FIG. 18A). Data shown (FIG. 18A) are means (±SEM); n=4 rats per group; P vs. vehicle: *<0.05; vs. E2: ‡<0.05. Further, when administered in combination with E2 (0.01 mg/kg), RAD1901 antagonized E2-mediated uterine stimulation in a dose-dependent manner, exhibiting significant inhibition of uterotropic activity at doses of 0.1 mg/kg and greater and complete inhibition at 3 mg/kg. The $EC_{50}$ for RAD1901 was approximately 0.3 mg/kg. Similar results were obtained in mice where RAD1901 doses 0.03 to 100 mg/kg also had no effect on uterine wet weight or epithelial thickness (data not shown).

Figure 18B:
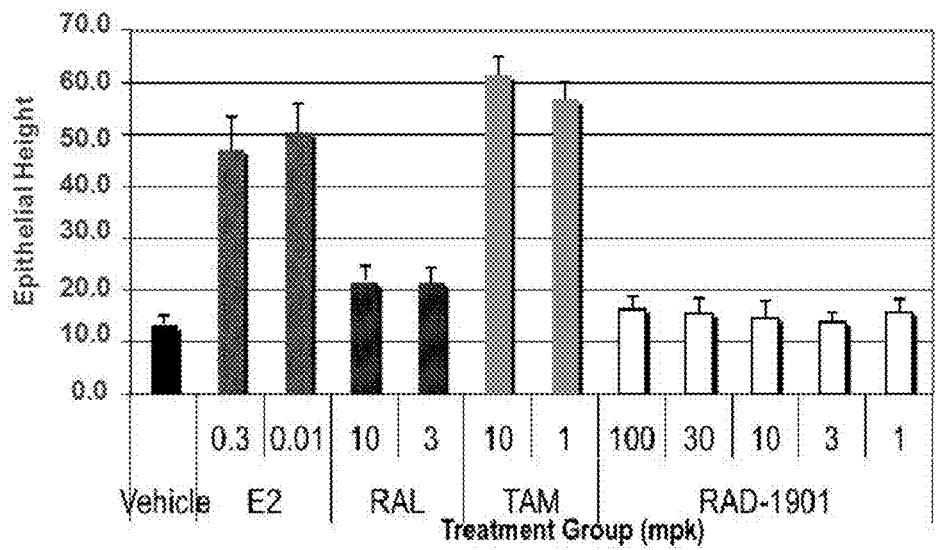
Figure 18C:
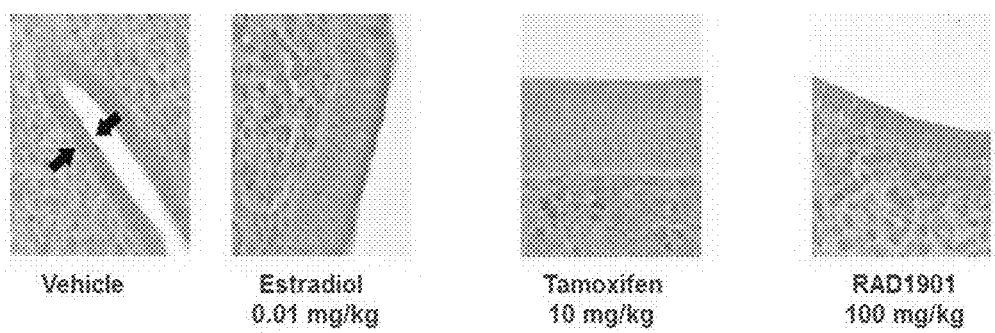

Treatment-dependent changes in uterine tissue were further investigated by quantitative microscopic histology. There was a statistically significant increase in endometrial epithelial thickness after treatment with E2 at both 0.01 and 0.3 mg/kg (FIG. 18B). A significant increase in epithelial thickness was also observed after treatment with tamoxifen (1 mg/kg) or raloxifene (3 mg/kg). In contrast, RAD1901 treatment did not increase endometrial epithelial thickness up to the highest evaluated dose of 100 mg/kg. Representative images of the endometrial epithelium are shown in FIG. 18C.

Figure 18D:
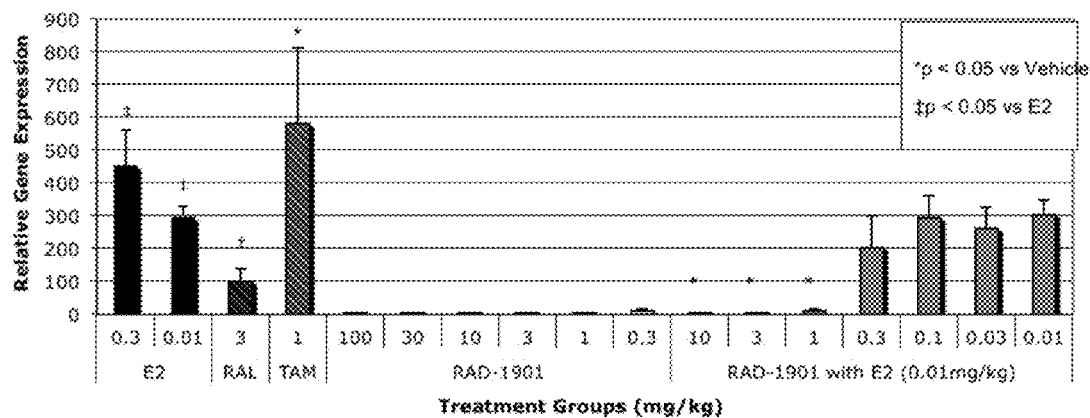

Consistent with the changes in both uterine weight and endometrial epithelial thickness, E2, tamoxifen, and raloxifene all significantly increased the expression of the estrogen-regulated complement gene, C3 (FIG. 18D). In contrast, RAD1901 did not increase C3 gene expression at any of the doses tested (0.3 to 100 mg/kg). Furthermore, RAD1901 at 1, 3 and 10 mg/kg significantly suppressed E2-stimulated C3 gene expression.

RAD1901 Did not Stimulate the Uterus of Immature Female Rats

Immature female rats were administered (orally) once daily, for 3 consecutive days with vehicle (VEH), estradiol (E2), Raloxifene (RAL), Tamoxifen (TAM), RAD1901 or RAD1901+E2. Wet uterine weights were measured. Data shown (FIG. 18) are means (±SEM); n=4 rats per group; P vs. vehicle: *<0.05; vs. E2: ‡<0.05.

Example II(A)(2). Treatment with RAD1901 Protected Against Bone Loss in Ovariectomized Rats The bone-specific effects of RAD1901 was examined in ovariectomized rats.

As a model of postmenopausal bone loss, ovariectomy was performed on anesthetized adult female Sprague-Dawley rats, with sham surgery as a control. Following surgery, ovariectomized rats were treated once daily for 4 weeks with vehicle, E2 (0.01 mg/kg), or RAD1901 (0.1, 0.3, 1, 3 mg/kg), administered as described above, with 20 animals per group. Animals in the sham surgery group were vehicle treated. All animals were euthanized by carbon dioxide inhalation 24 hours after the final dose. Bone mineral density was assessed at baseline and again after 4 weeks of treatment using PIXImus dual emission x-ray absorptiometry.

At necropsy, the left femur of each animal was removed, dissected free of soft tissue and stored in 70% ethanol before analysis. A detailed qualitative and quantitative 3-D evaluation was performed using a micro-CT40 system (Scanco Systems, Wayne, PA). For each specimen, 250 image slices of the distal femur metaphysis were acquired. Morphometric parameters were determined using a direct 3-D approach in pre-selected analysis regions. Parameters determined in the trabecular bone included bone volume density, bone surface density, trabecular number, trabecular thickness, trabecular spacing, connectivity density, and apparent bone density.

Following ovariectomy, untreated (vehicle control) rats experienced a decrease in bone mineral density both in the whole full femur and in the lumbar spine compared to baseline (Table 4). Treatment with E2 was associated with prevention of bone loss in both the femur and spine. Treatment with RAD1901 resulted in a dose-dependent and statistically significant suppression of ovariectomy-induced bone loss (data shown for the 3 mg/kg treatment group). At doses of 0.1 mg/kg to 3 mg/kg, bone mineral density in RAD1901-treated rats was complete, with no statistically significant difference from the E2-treated group.

Micro-CT analysis of the distal femur (Table 5) demonstrated that ovariectomy induced significant changes in a number of key micro-architectural parameters when compared to sham surgery animals. These changes were consistent with a decrease in bone mass and include decreased bone volume, reduced trabecular number, thickness and density, and increased trabecular separation. Consistent with the preservation of bone mineral density observed after treatment with RAD1901, significant preservation of trabecular architecture was observed in key micro-structural parameters (Table 5)

Example IV(B): Phase 1 Dose Escalation Study of RAD101 in Healthy Postmenopausal Women In the phase 1 study, safety, tolerability and pharmacokinetics were evaluated in 44 healthy postmenopausal females. No dose limiting toxicities (DLT) were observed, maximum tolerated dose (MTD) was not established. Plasma exposure increased more than dose proportionally over the dose range tested.

Subjects 44 healthy postmenopausal females were enrolled as subjects for this phase 1 study. The subjects had an amenorrhea duration of at least 12 months and serum FSH consistent with menopause. The subjects were 40-75 years old with BMI of 18.0-30 $kg/m^2$. Subjects having evidence of clinically relevant pathology, increased risk of stroke or of history venous thromboembolic events, or use of concomitant medication less than 14 days prior to admission to clinical research center (paracetamol allowed up to 3 days prior) were excluded.

Dosing

The subjects were treated with placebo or at least one oral dose daily after a light breakfast for 7 days at dose levels of 200 mg, 500 mg, 750 mg and 1000 mg, respectively. The key baseline demographics of the 44 healthy postmenopausal females enrolled in the phase 1 study are summarized in Table 6.

Treatment Emergent Adverse Events (TEAEs)

TEAEs were recorded, and the most frequent (>10% of patients in the total active group who had any related TEAEs) adverse events (AEs) are summarized in Table 7, "n" is number of subjects with at least one treatment-related AE in a given category, AEs graded as per the Common Terminology Criteria for Adverse Events (CTCAE) v4.0, and any patient with multiple scenarios of a same preferred term was counted only once to the most severe grade. No dose limiting toxicities were observed, maximum tolerated dose (MTD) was not established.

Pharmacokinetic Evaluations

A series of blood samples were taken during the study for the analysis of RAD1901 in plasma. Blood samples of 5 mL each were taken via an indwelling IV catheter or by direct venipuncture into tubes containing $K_3$-EDTA as anticoagulant. Steady state was achieved by day 5 of treatment. Geometric Mean (Geo-Mean) plasma concentration-time profiles of RAD1901 were evaluated. Plasma pharmacokinetic results of the groups treated with RAD1901 (200, 500, 750 or 1,000 mg) on Day 7 (N=35) in the study are provided in Table 8 and FIG. 19, as an example. The median $t_{1/2}$ was between 37.5-42.3 hours (Table 8). After multiple dose administration of RAD1901, median $t_{max}$ ranged between 3-4 hours post-dose.

Example V(A)-1. Modeling of RAD1901-ERα Binding Using Select Published ER Structures Unless specified otherwise, when structures are shown by their stick model, each end of a bond is colored with the same color as the atom to which it is attached, wherein grey is carbon, red is oxygen, blue is nitrogen and white is hydrogen.

Fourteen published structures (i.e., models) of ERα ligand-binding domain (LBD) complexed with various ER ligands were selected from 96 published models by careful evaluation. One of these fourteen models was 3ERT (human ERα LBD bound to 4-hydroxytamoxifen (OHT)). OHT is the active metabolite of tamoxifen and a first generation SERM that functions as an antagonist in breast tissue.

In 3ERT (FIGS. 20 and 21), the ERα binding site adopts a three layer "helical sandwich" forming a hydrophobic pocket which includes Helix 3 (H3), Helix 5 (H5), and Helix 11 (H11) (FIG. 20). The dotted box in FIG. 21 represents the binding site and residues within the binding site that are important or are effected by OHT binding. OHT functions as an antagonist by displacing H12 into the site where LXXLL coactivator(s) binds. OHT occupies the space normally filled by L540 and modifies the conformation of four residues on the C-terminal of Helix 11 (G521, H524, L525, and M528). OHT also forms a salt bridge with D351, resulting in charge neutralization.

The other thirteen ERα LBD-ER ligand models were compared to 3ERT. Differences in their residue poses are summarized in Table 10. Superimposition of the ERα structures of the fourteen models (FIG. 22) shows that these structures differed significantly at residues E380, M421, G521, M522, H524, Y526, S527, M528, P535, Y537, L540, and various combinations thereof.

Root-mean-square deviation (RMSD) calculations of any pair of the fourteen models are summarized in Table 11. Structures were considered to be overlapping when their RMSD was <2 Å. Table 11 shows that all fourteen models had a RMSD<1.5 Å. Using conditional formatting analysis suggested that 1R5K and 3UUC were the least similar to the other models (analysis not shown). Therefore, 1R5K and 3UUC were considered a unique, separate structural cluster to be examined.

ERα residues bound by ligand in the fourteen models are summarized in Table 12. Table 12 also shows the $EC_{50}$ in the ERα LBD-antagonist complexes. Out of the fourteen models, thirteen showed H-bond interactions between the ligand and E353; twelve showed pi interactions between the ligand and F404; five showed H-bond interactions between the ligand and D351; six showed H-bond interactions between the ligand and H524; four showed H-bond interactions between the ligand and R394; and one (3UUC) showed interactions between the ligand and T347.

Each of the fourteen models was used to dock a random library of 1,000 compounds plus the ligand the model was published with (the known antagonist) to determine whether the model could identify and prioritize the known antagonist. If the model could identify the known antagonist, the model was determined to be able to predict the pose of its own published ligand. $EF_{50}$ was then calculated to quantify the model's strength to see how much better it was than a random selection. RAD1901 was docked in the selected models (e.g., FIGS. 23A&B-27A&B). Docking scores of the published ligand and RAD1901 in the models were determined. $EC_{50}$ was also determined. Visual inspection of RAD1901 showed that it "obeyed" the interactions shown with the published ligands in 1R5K, 1SJ0, 2JFA, 2BJ4, and 2OUZ. No spatial clashes were noticed. In certain embodiments, e.g., in 1R5k and 2BJ4, RAD1901 had a higher docking score than the published ligand.

The evaluation results of nine models (1ERR, 3ERT, 3UCC, 2IOK, 1R5K, 1SJ0, 2JFA, 2BJ4, and 2OUZ) are summarized in Table 13.

1ERR and 3ERT could not predict the correct pose of their crystallized ligand. RAD1901 did not dock in 3UCC. The tetrahydronaphtalene in 2IOK-RAD1901 bound in a non-traditional manner.

The major differences between the models 1R5K, 1SJ0, 2JFA, 2BJ4, and 2OUZ were the residues in the C-term of Helix 11 (G521-M528).

FIGS. 23A&B shows the modeling of RAD1901-1R5K (A) and GW5-1R5K (B). RAD1901 bound with H-bond interactions to E353, R394, and L536; and with p-interaction with F404.

FIGS. 24A&B shows the modeling of RAD1901-1SJ0 (A) and E4D-1SJ0 (B). RAD1901 bound with H-bond interactions to E353, and D351; and with p-interaction with F404.

FIGS. 25A&B shows the modeling of RAD1901-2JFA (A) and RAL-2JFA (B). RAD1901 bound with p-interaction with F404.

FIGS. 26A&B shows the modeling of RAD1901-2BJ4 (A) and OHT-2BJ4 (B). RAD1901 bound with H-bond interactions with E353 and R394; and p-interaction with F404.

FIGS. 27A&B shows the modeling of RAD1901-2IOK (A) and IOK-2IOK (B). RAD1901 bound with H-bond interactions with E353, R394, and D351; and p-interaction with F404.

The published ligands in the models have the following structures:

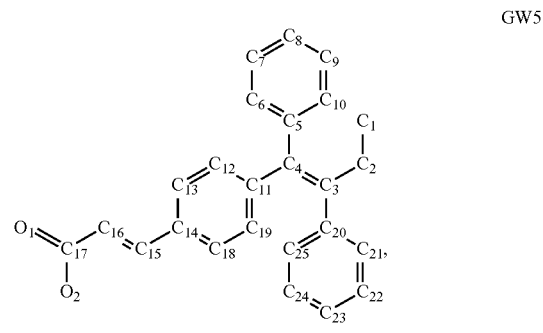

(2E)-3-{4-[(1E)-1,2-DIPHENYLBUT-1-ENYL]PHENYL}ACRYLIC ACID

-continued

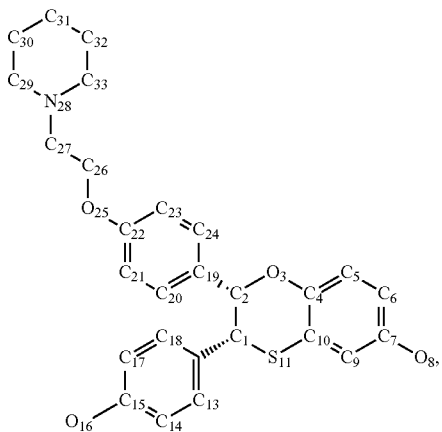

(2S,3R)-2-(4-(2-PIPERIDIN-1-YL)ETHOXY)PHENYL)-
2,3-DIHYDRO-3-(4-HYDROXYPHENYL)BENZO[B]
[1,4]OXATHIIN-6-OL

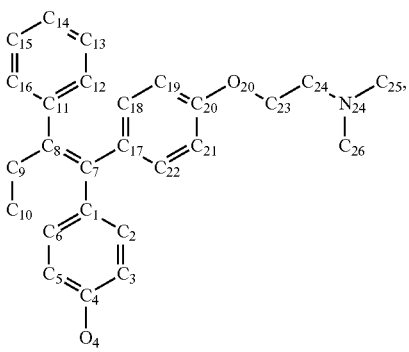

4-HYDROXYTAMOXIFEN

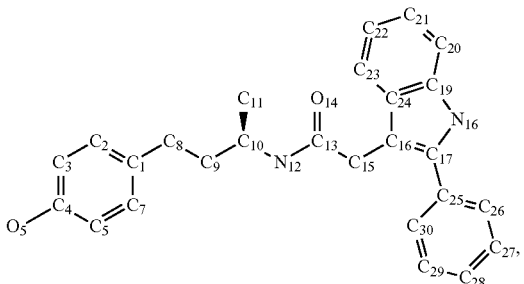

N-[(1R)-3-(4-HYDROXYPHENYL)-1-METHYLPROPYL]-
2-(2-PHENYL-1H-INDOL-3-YL)ACETAMIDE

Example V(A)-2. Induced Fit Docking (IFD) of
ERα with RAD1901 and Fulvestrant

Binding conformation of RAD1901 in ERα was further optimized by IFD analysis of the five ERα crystal structures 1R5K, 1SJ0, 2JFA, 2BJ4, and 2OUZ. IFD analysis accounted for the receptor flexibility (upon ligand binding) to accommodate its correct binding conformation.

A library of different conformations for each ligand (e.g., RAD1901 and fulvestrant) was generated by looking for a local minima as a function of rotations about rotatable bonds. The library for RAD1901 had 25 different conformations.

The five ERα crystal structures were prepared and minimized. The corresponding ligand in the published X-ray structures were used to define the ERα binding pocket.

RAD1901 conformations were docked into the prepared ERα structures wherein they were allowed to induce side-chain or back-bone movements to residues located in the binding pocket. Those movements allowed ERα to alter its binding site so that it was more closely conformed to the shape and binding mode of the RAD1901 conformation. In some examples, small backbone relaxations in the receptor structure and significant side-chain conformation changes were allowed in the IFD analysis.

An empirical scoring function was used to approximate the ligand binding free energy to provide a docking score or Gscore. Gscore is also known as GlideScore, which may be used interchangeably with docking score in this example. The docking score was an estimate of the binding affinity. Therefore, the lower the value of the docking score, the "better" a ligand bound to its receptor. A docking score of −13 to −14 corresponded to a very good binding interaction.

The RAD1901 conformations resulted from the IFD analysis with 1R5K, 1SJ0, 2JFA, 2BJ4, and 2OUZ respectively were superimposed to show their differences (FIGS. 28-30A&B, shown in stick model). All bonds in each RAD1901 conformation were shown in the same color in FIGS. 28, 29 and 30A.

The RAD1901 conformations resulted from the IFD analysis with 1R5K (blue) and 2OUZ (yellow) had N-benzyl-N-ethylaniline group of RAD1901 on the front (FIG. 28). The RAD1901 conformations resulted from the IFD analysis with 2BJ4 (green) and 2JFA (pink) had N-benzyl-N-ethylaniline group of RAD1901 on the back (FIG. 29). The RAD1901 conformations resulted from the IFD analysis with 2BJ4 (green), 2JFA (pink) and 1SJ0 (brown) were quite similar as shown by their superimpositions (FIGS. 30A and 30B). The RAD1901 IFD docking scores are summarized in Table 14.

The IFD of RAD1901 with 2BJ4 showed hydrogen bond interactions with E353 and D351 and pi-interactions with F404 (FIGS. 31A-31C). FIG. 31A showed regions within the binding site suitable for H-bond acceptor group (red), H-bond donor group (blue) and hydrophobic group (yellow). In FIGS. 31A and 31B, light blue was for carbon for RAD1901. FIGS. 32A-32C show a protein-surface interactions of the IFD of RAD1901 with 2BJ4. FIGS. 32A and 32B are the front view, and FIG. 32C is the side view. The molecular surface of RAD1901 was blue in FIG. 32A, and green in FIG. 32C. FIGS. 32B and 32C are electrostatic representation of the solvent accessible surface of ERα, wherein red represented electronegative and blue represented electropositive.

Similar IFD analysis was carried out for fulvestrant with 2BJ4 as described supra. The fulvestrant-2BJ4 IFD resulted in a Gscore of −14.945 and showed hydrogen bond interactions with E353, Y526, and H524 and pi-interactions with F404 (FIGS. 33A-33C). FIG. 33A showed regions within the binding site suitable for H-bond acceptor group (red), H-bond donor group (blue) and hydrophobic group (yellow). In FIG. 33A, light blue was for carbon for RAD1901.

FIGS. 34A and 34B showed RAD1901 and fulvestrant docked in 2BJ4 by IFD both had pi-interactions with F404 and hydrogen bond interactions with E353. Furthermore, RAD1901 had hydrogen bond interaction with D351 (blue representing RAD1901 molecular surface, FIG. 34B), while fulvestrant had hydrogen bond interactions with Y526, and H524 (green representing fulvestrant molecular surface, FIG. 34C). Superimpositions of 2BJ4 docked with RAD1901 and fulvestrant are shown in FIGS. 35A and 35B. In FIG. 35A, green represents fulvestrant molecular surface and blue represents RAD1901 molecular surface. In FIG. 35B, the brown structure is fulvestrant and the blue structure is RAD1901.

Example V(A)-3. Modeling Evaluation of Select ERα Mutations

Effects of various ERα mutations on the C-terminal ligand-binding domain were evaluated. Specific ERα mutations evaluated were Y537X mutant wherein X was S, N, or C; D538G; and S463P.

Y537 resides in Helix 12. It may regulate ligand binding, homodimerization, and DNA binding once it is phosphorylated, and may allow ERα to escape phosphorylation-mediated controls and provide a cell with a potential selective tumorigenic advantage. In addition, it may cause conformational changes that makes the receptor constitutively active.

The Y537S mutation favors the transcriptionally active closed pocket conformation, whether occupied by ligand or not. The closed but unoccupied pocket may account for ERα's constitutive activity (Carlson et al. Biochemistry 36:14897-14905 (1997)). Ser537 establishes a hydrogen-bonding interaction with Asp351 resulting in an altered conformation of the helix 11-12 loop and burial of Leu536 in a solvent-inaccessible position. This may contribute to constitutive activity of the Y537S mutant protein. The Y537S surface mutation has no impact on the structure of the LBD pocket.

Y537N is common in ERα-negative metastatic breast cancer. A mutation at this site may allow ERα to escape phosphorylation-mediated controls and provide a cell with a potential selective tumorigenic advantage. Specifically, Y537N substitution induces conformational changes in the ERα that might mimic hormone binding, not affecting the ability of the receptor to dimerize, but conferring a constitutive transactivation function to the receptor (Zhang et al. Cancer Res 57:1244-1249 (1997)).

Y537C has a similar effect to Y537N.

D538G may shift the entire energy landscape by stabilizing both the active and inactive conformations, although more preferably the active. This may lead to constitutive activity of this mutant in the absence of hormones as observed in hormone-resistant breast cancer (Huang et al., "A newfound cancer-activating mutation reshapes the energy landscape of estrogen-binding domain," *J. Chem. Theory Comput.* 10:2897-2900 (2014)).

None of these mutations are expected to impact the ligand binding domain nor specifically hinder RAD1901 binding. Y537 and D538 may cause conformational changes that leads to constitutive receptor activation independent of ligand binding.

Example V(B). In Vitro Binding Assay of ERα Constructs of Wildtype and LBD Mutant with RAD1901 and Other Compounds In vitro binding assay of ERα constructs of wildtype (WT) and LBD mutant with RAD1901 showed that RAD1901 bound to mutant ERα with a similar affinity as to WT ERα.

ERα constructs of WT and LBD mutant were prepared by expressing and purifying the corresponding LBD residues 302-552 with N-terminal thioredoxin and 6×His tags which were cleaved by TEV protease.

Fluorescence polarization (FP) was used to determine binding of test compounds (RAD1901, fulvestrant, bazedoxifene, raloxifene, tamoxifene, and AZD9496) to ERα as per manufacturer's instructions (Polar Screen, Invitrogen) with 2 nM fluoromone, 100 nM ERα construct of WT or LBD mutant. Each set was carried out in duplicate and tested one test compound to determine the $IC_{50}$ for different ERα constructs (FIG. 36 for RAD1901 binding essay).

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

TABLE 1

RAD1901 levels in plasma, tumor and brain of mice implanted with MCF7 cells after treated for 40 days.

| | Dose (mg/kg) | Plasma (ng/mL) | Tumor (ng/mL) | Brain (ng/mL) | B/P Ratio | T/P Ratio |
|---|---|---|---|---|---|---|
| Vehicle | | BLQ* | BLQ | BLQ | — | — |
| RAD1901 | 0.3 | 2 | 11 | BLQ | — | |
| RAD1901 | 1 | 3 | 45 | BLQ | — | |
| RAD1901 | 3 | 9 | 169 | 7 | 0.78 | 18.78 |
| RAD1901 | 10 | 39 | 757 | 14 | 0.36 | 19.41 |
| RAD1901 | 30 | 137 | 3875 | 72 | 0.53 | 28.28 |
| RAD1901 | 60 | 334 | 11117 | 201 | 0.60 | 33.28 |

*BLQ: below the limit of quantitation

TABLE 2

SUV for uterus, muscle, and bone for a human subject treated with 200 mg dose PO once/day for six days

| Dose | Uterus SUV % Change | Bone SUV % Change | Muscle SUV % Change |
|---|---|---|---|
| 200 mg | −85% | 16% | 0% |

TABLE 3

SUV for uterus, muscle, and bone for human subjects (n = 4) treated with 500 mg dose PO once/day for six days.

| Subject # | Scan | Mean Uterus SUV | Uterus SUV Change (%) | Mean Muscle SUV | Muscle SUV Change (%) | Mean Bone SUV | Bone SUV Change (%) |
|---|---|---|---|---|---|---|---|
| 1 | Baseline | 3.88 | | 0.33 | | 0.36 | |
|   | Day 6 | 0.58 | −85 | 0.31 | −6 | 0.48 | 33 |
| 2 | Baseline | 6.47 | | 0.25 | | 0.49 | |
|   | Day 6 | 0.33 | −86 | 0.42 | 68 | 0.55 | 12 |
| 3 | Baseline | 3.66 | | 0.50 | | 0.41 | |
|   | Day 6 | 0.58 | −84 | 0.31 | −38 | 0.47 | −23 |
| 4 | Baseline | 3.35 | | 0.30 | | 0.40 | |
|   | Day 6 | 0.41 | −88 | 0.24 | −20 | 0.52 | 30 |
| Mean | | | −86 | | 1 | | 13 |

TABLE 4

Effect of RAD1901 on BMD in ovariectomized rats.[a]

| Treatment | Femur BMD (% change) | Lumbar Spine BMD (% change) |
|---|---|---|
| Sham | 3.1 ± 2.4* | 2.7 ± 5.0* |
| OVX + veh | −5.4 ± 5.1 | −10.2 ± 12.8 |
| OVX + E2 | −0.5 ± 2.6* | −2.1 ± 12.2* |
| OVX + RAD1901 | 0.4 ± 2.8* | −1.1 ± 7.9* |

[a]Adult female rats underwent either sham or ovariectomy surgery before treatment initiation with vehicle, E2 (0.01 mg/kg) or RAD1901 (3 mg/kg) once daily (n = 20 per treatment group). BMD was measured by dual emission x-ray absorptiometry at baseline and after 4 weeks of treatment. Data are expressed as mean ± SD.
*$P < 0.05$ versus the corresponding OVX + Veh control. BMD, bone mineral density; E2, beta estradiol; OVX, ovariectomized; Veh, vehicle.

TABLE 5

Effect of RAD1901 on femur microarchitecture in ovariectomized rats[a]

| Treatment | BV/TV (%) | ConnD (1/mm$^3$) | TbN (1/mm) | TbTh (mm) | TbSp (mm) | ABD (mgHA/ccm) |
|---|---|---|---|---|---|---|
| Sham | 0.394 ± 0.069* | 138 ± 21* | 5.2 ± 0.6* | 0.095 ± 0.008* | 0.175 ± 0.029* | 456 ± 61* |
| OVX + Veh | 0.234 ± 0.065 | 91 ± 32 | 3.5 ± 0.9 | 0.085 ± 0.011 | 0.307 ± 0.086 | 301 ± 69 |
| OVX + E2 | 0.309 ± 0.079* | 125 ± 25* | 4.8 ± 0.8* | 0.086 ± 0.008 | 0.204 ± 0.054* | 379 ± 75* |
| OVX + RAD1901 | 0.300 ± 0.066* | 113 ± 22* | 4.5 ± 0.8* | 0.088 ± 0.008 | 0.218 ± 0.057* | 370 ± 66* |

[a]Adult female rats underwent either sham or ovariectomy surgery before treatment initiation with vehicle, E2 (0.01 mg/kg) or RAD1901 (3 mg/kg) once daily (n = 20 per treatment group). After 4 weeks, Bone microarchitecture was evaluated using microcomputed tomography. Data are expressed as mean ± SD.
*$P < 0.05$ versus the corresponding OVX + Veh control. ABD, apparent bone density; BV/TV, bone volume density; ConnD, connectivity density; E2, beta estradiol; OVX, ovariectomized; TbN, trabecular number; TbTh, trabecular thickness; TbSp, trabecular spacing; Veh, vehicle.

TABLE 6

Key baseline demographics of Phase 1 dose escalation study of RAD1901

| | Placebo (N = 8) | RAD1901 200 mg (N = 15) | RAD1901 500 mg (N = 14) | RAD1901 750 mg (N = 8) | RAD1901 1,000 mg (N = 7) |
|---|---|---|---|---|---|
| Race white (% of the cohort) | 8(100) | 14(93) | 10(71) | 8(100) | 7(100) |
| Mean age, years | 64 | 62 | 59 | 64 | 64 |
| Mean BMI, kg/m$^2$ | 26.1 | 25 | 24.4 | 24.9 | 26.7 |

TABLE 7

Most frequent (>10%) treatment related AEs in a Phase 1 dose escalation study of RAD1901

| | Placebo N = 8 n(%) | | | 200 mg N = 15 n(%) | | | 500 mg N = 14 n(%) | | | 750 mg N = 8 n(%) | | | 1000 mg N = 7 n(%) | | | Total Active N = 44 n(%) | | | Total TEAE N = 44 |
|---|---|---|---|---|---|---|---|---|---|---|---|---|---|---|---|---|---|---|---|
| | Gr1 | Gr2 | Gr3 | Gr1 | Gr2 | Gr3 | Gr1 | Gr2 | Gr3 | Gr1 | Gr2 | Gr3 | Gr1 | Gr2 | Gr3 | Gr1 | Gr2 | Gr3 | All |
| Nausea | 2 (25) | 0 | 0 | 5 (33) | 0 | 0 | 3 (21) | 2 (14) | 0 | 2 (25) | 1 (13) | 0 | 4 (57) | 2 (29) | 0 | 14 (32) | 5 (11) | 0 | 19 (43) |
| Dyspepsia | 1 (13) | 0 | 0 | 3 (20) | 0 | 0 | 5 (36) | 2 (14) | 0 | 4 (50) | 0 | 0 | 1 (14) | 1 (14) | 0 | 13 (30) | 3 (7) | 0 | 16 (36) |
| Vomiting | 0 | 0 | 0 | 2 (13) | 0 | 0 | 1 (7) | 5 (36) | 1 (7) | 0 | 2 (25) | 0 | 0 | 3 (43) | 0 | 3 (7) | 10 (23) | 1 (2) | 14 (32) |
| Hot flush | 1 (13) | 0 | 0 | 2 (13) | 0 | 0 | 6 (43) | 0 | 0 | 2 (25) | 0 | 0 | 1 (14) | 0 | 0 | 11 (25) | 0 | 0 | 11 (25) |
| Abdominal pain | 1 (13) | 0 | 0 | 2 (13) | 2 (13) | 0 | 3 (21) | 0 | 0 | 1 (13) | 0 | 0 | 1 (14) | 1 (14) | 0 | 7 (16) | 3 (7) | 0 | 10 (23) |
| Oesophageal pain | 0 | 0 | 0 | 0 | 2 (13) | 0 | 1 (7) | 3 (21) | 0 | 1 (13) | 0 | 0 | 1 (14) | 1 (14) | 1 (14) | 3 (7) | 6 (14) | 1 (2) | 10 (23) |
| Headache | 0 | 0 | 0 | 3 (20) | 0 | 0 | 1 (7) | 1 (7) | 0 | 3 (38) | 0 | 0 | 2 (29) | 0 | 0 | 9 (20) | 1 (2) | 0 | 10 (23) |
| Hiccups | 0 | 0 | 0 | 1 (7) | 0 | 0 | 4 (29) | 0 | 0 | 2 (25) | 0 | 0 | 2 (29) | 0 | 0 | 9 (20) | 0 | 0 | 9 (20) |
| Salivary hypersecretion | 0 | 0 | 0 | 2 (13) | 0 | 0 | 2 (14) | 0 | 0 | 2 (25) | 0 | 0 | 2 (29) | 0 | 0 | 8 (18) | 0 | 0 | 8 (18) |
| Diarrhoea | 1 (13) | 0 | 0 | 0 | 0 | 0 | 3 (21) | 0 | 0 | 0 | 0 | 0 | 3 (43) | 1 (14) | 0 | 6 (14) | 1 (2) | 0 | 7 (16) |
| Dysphagia | 0 | 0 | 0 | 0 | 0 | 0 | 1 (7) | 2 (14) | 0 | 3 (38) | 1 (13) | 0 | 0 | 0 | 0 | 4 (9) | 3 (7) | 0 | 7 (16) |
| Sensation of a foreign body | 0 | 0 | 0 | 2 (13) | 0 | 0 | 1 (7) | 0 | 0 | 0 | 0 | 0 | 4 (57) | 0 | 0 | 7 (16) | 0 | 0 | 7 (16) |
| Abdominal distension | 0 | 0 | 0 | 1 (7) | 1 (7) | 0 | 1 (7) | 0 | 0 | 1 (13) | 0 | 0 | 2 (29) | 0 | 0 | 5 (11) | 1 (2) | 0 | 6 (14) |
| Odynophagia | 0 | 0 | 0 | 2 (13) | 0 | 0 | 1 (7) | 1 (7) | 0 | 0 | 0 | 0 | 1 (14) | 1 (14) | 0 | 4 (9) | 2 (5) | 0 | 6 (14) |
| Dizziness | 2 (25) | 0 | 0 | 1 (7) | 0 | 0 | 2 (14) | 0 | 0 | 1 (13) | 0 | 0 | 1 (14) | 0 | 0 | 5 (11) | 0 | 0 | 5 (11) |
| Abdominal discomfort | 0 | 0 | 0 | 3 (20) | 0 | 0 | 0 | 0 | 0 | 1 (13) | 1 (13) | 0 | 0 | 0 | 0 | 4 (9) | 1 (2) | 0 | 5 (11) |
| Flatulance | 0 | 0 | 0 | 2 (13) | 0 | 0 | 2 (14) | 0 | 0 | 1 (13) | 0 | 0 | 0 | 0 | 0 | 5 (11) | 0 | 0 | 5 (11) |
| Myalgia | 1 (13) | 0 | 0 | 2 (13) | 1 (7) | 0 | 0 | 1 (7) | 0 | 1 (13) | 0 | 0 | 0 | 0 | 0 | 3 (7) | 2 (5) | 0 | 5 (11) |

TABLE 8

Pharmacokinetic parameters in a Phase 1 dose escalation study of RAD1901 (Day 7)

| Parameter | Statistic | 200 mg N = 15 | 500 mg N = 11 | 750 mg N = 6 | 1000 mg N = 3 |
|---|---|---|---|---|---|
| $C_{max}$ (ng/mL) | Geo-Mean | 49.8 | 197 | 322 | 540 |
| | Min, Max | 30.6, 85.5 | 105, 316 | 248, 420 | 481, 602 |
| $t_{max}$ (h) | Median | 3.00 | 4.00 | 3.00 | 4.00 |
| | Min, Max | 2.00, 6.00 | 2.00-6.02 | 3.00, 4.00 | 3.00, 6.00 |
| $AUC_{0-tau}$ (h*ng/mL) | Geo-Mean | 670 | 2927 | 4614 | 8292 |
| | Min, Max | 418, 1181 | 1562, 5460 | 3209, 7183 | 7281, 8947 |
| $t_{1/2}$ (h) | Geo-Mean | 38.3 | 37.5 | 38.4 | 42.3 |
| | Min, Max | 27.7, 51.4 | 33.8, 41.3 | 34.6, 46.4 | 38.7, 49.4 |

TABLE 9

Frequency of LBD mutations

| | Frequency (%) |
|---|---|
| D538G | 29.5 |
| Y537S | 25.0 |
| Y537N | 13.6 |
| Y537C | 9.1 |
| E380Q | 6.8 |
| S463P | 4.5 |
| L536R | 2.3 |
| L536Q | 2.3 |
| P535H | 2.3 |
| V392I | 2.3 |
| V534E | 2.3 |

TABLE 10

Differences of ER-α LBD-antagonist complexes in residue poses versus 3ERT

| Residue | L1-3/Helix 8 | | Helix 11 | | | | | | | Helix 5 | Helix 12 | |
|---|---|---|---|---|---|---|---|---|---|---|---|---|
| #/PDB | M421 | I424 | E521 | M522 | H524 | L525 | Y526 | S527 | M528 | E380 | Y537 | L540 |
| 2BJ4 | x | x | | x | x | | x | | x | x | NA | |
| 2JFA | x | x | | x | x | | x | x | x | | NA | |
| 1SJ0 | x | x | x | x | x | | x | x | x | | | |
| 2JF9 | | x | | x | x | x | x | x | x | | NA | |
| 1YIM | x | x | | x | x | | x | | x | | | |
| 1R5K | x | x | | x | x | | x | x | X | | x | x |
| 1UOM | x | x | | x | x | | | | | | | |
| 1ERR | x | x | | | x | x | x | x | | | | |
| 2IOK | x | x | | x | | | x | x | x | | x | x |
| 3UUC | x | x | | x | | | x | x | x | x | x | |
| 1YIN | x | x | x | X | x | x | x | x | x | | | |
| 2AYR | x | | | X | x | | | | x | | | |
| 2OUZ | x | x | | | | | x | | x | | | |

TABLE 11

Evaluation of structure overlap of ER-α LBD-antagonist complexes by RMSD calculations:

| RMSD | 3ERT | 2BJ4 | 2JFA | ISJ0 | 2JF9 | 1Y1M | 1R5K | 1UOM | 1ERR | 2IOK | 3UUC | 1Y1N | 2AYR |
|---|---|---|---|---|---|---|---|---|---|---|---|---|---|
| 3ERT | | | | | | | | | | | | | |
| 2BJ4 | 0.804 | | | | | | | | | | | | |
| 2JFA | 1.196 | 0.554 | | | | | | | | | | | |
| 1SJ0 | 0.786 | 0.637 | 1.115 | | | | | | | | | | |
| 2JF9 | 1.177 | 0.411 | 0.415 | 1.186 | | | | | | | | | |
| 1Y1M | 0.978 | 0.687 | 1.118 | 0.276 | 1.072 | | | | | | | | |
| 1R5K | 1.483 | 0.759 | 0.52 | 1.307 | 0.892 | 1.342 | | | | | | | |
| 1UOM | 0.739 | 0.761 | 0.723 | 0.489 | 0.909 | 0.499 | 1.115 | | | | | | |
| 1ERR | 1.12 | 0.483 | 0.595 | 1.016 | 0.851 | 1.112 | 1.208 | 0.918 | | | | | |
| 2IOK | 0.824 | 0.689 | 0.787 | 0.899 | 0.897 | 0.854 | 1.208 | 0.736 | 0.838 | | | | |
| 3UUC | 1.024 | 0.915 | 0.896 | 1.03 | 0.888 | 1.036 | 1.228 | 1.012 | 0.873 | 0.929 | | | |
| 1Y1N | 0.749 | 0.683 | 1.105 | 0.432 | 1.061 | 0.318 | 1.293 | 0.557 | 1.076 | 0.744 | 1.015 | | |
| 2AYR | 0.659 | 0.682 | 0.95 | 0.792 | 1.124 | 0.777 | 1.391 | 0.491 | 1.118 | 0.071 | 1.031 | 0.581 | |

TABLE 12

Analysis of ligand binding in ER-α LBD-antagonist complexes

| | Ligand: Binding to | EC$_{50}$ (μM) | Comments |
|---|---|---|---|
| 3ERT | OHT: E353, R394 | 0.010 | Flipped amine, F404 was too far from the phenol thus there were no pi-interactions |
| 2BJ4 | OHT: E353, R394, pi F404 | 0.010 | |
| 2JF9 | OHT: E353, D351, H524, pi F404 | 0.010 | |
| 2JFA | RAL: E353, D351, H524 and pi F404 x2 | 0.002 | |
| 1ERR | RAL: E353, D351, R394 and pi F404 x2 | 0.002 | Phenol flipped for H524 |
| 1YIM | CM3: E353, H524 D351 pi F404 | 0.0015(IC$_{50}$) | D351-carboxyle oriented well with pyrrolidine |
| 1YIN | CM3: E535, H524 pi F404 | 0.001 | |
| 1SJ0 | E4D: E353, H524, pi F404 x 2 | 0.0008(IC$_{50}$) | |
| 1R5K | GW5: D351 pi F404 | 0.039(IC$_{50}$) | No anchor bond with E353 |
| IUOM | PTI: E353, H524 pi F404 | NA | |
| 2IOK | IOK: E353 pi F404 | 0.001 | |
| 3UUC | OD1: E353, R394, T347 | NA | Very small compound |
| 2OUZ | C3D: E353, pi F404 | 0.003 | |
| 2AYR | L4G: E353, pi F404 x2 | 0.0107 | |

TABLE 13

Model evaluation for RAD1901 docking

| | EC$_{50}$(μM) | EF$_{50}$ (=predictive power) | Can model predict crystal structure? | Ligand docking score | RAD1901 docking score |
|---|---|---|---|---|---|
| 1ERR | 0.001 | | No | −11.452 | −7.912 |
| 3ERT | 0.002 | | No | −12.175 | −8.151 |
| 3UCC | NA | 8474 | Yes | −9.278 | NA |
| 2IOK | 0.001 | | Yes | −11.952 | −10.478 |
| 1R5K | 0.039 | 6100 | Yes | −11.518 | −12.102 |
| 1SJ0 | 0.001 | 7511 | Yes | −12.507 | −9.816 |
| 2JFA | 0.001 | 6780 | Yes | −11.480 | −11.055 |
| 2BJ4 | 0.002 | 5642 | Yes | −9.727 | −11.971 |
| 2OUZ | 0.003 | — | Yes | −11.789 | −9.611 |

TABLE 14

Induced Fit Docking Score of RAD1901 with 1R5K, 1SJ0, 2JFA, 2BJ4 and 2OUZ

| ER-α Crystal Structure | RAD1901 IFD Docking Score |
|---|---|
| 1R5K | −14.1 |
| 1SJ0 | −13.1 |
| 2JFA | −13.9 |
| 2BJ4 | −13.8 |
| 2OUZ | −13.4 |

What is claimed is:

1. A method of treating breast cancer in a subject having an estrogen receptor alpha-positive cancer that has a Y537S mutant estrogen receptor alpha comprising administering to said subject a therapeutically effective amount of a combination of an m-TOR inhibitor selected from the group consisting of sirolimus, temsirolimus, everolimus, and ridaforolimus, and RAD1901 having the structure:

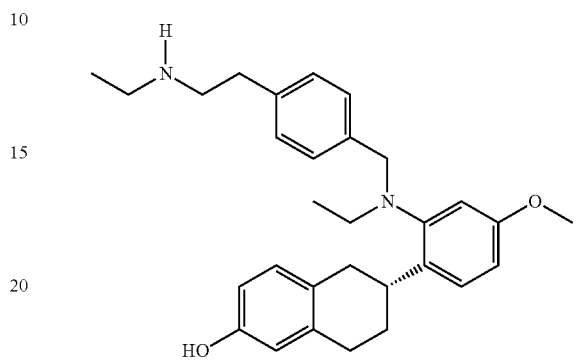

or a salt or solvate thereof.

2. The method of claim 1 wherein said breast cancer is a drug resistant breast cancer and is resistant to one or more antiestrogen and/or or aromatase inhibitor therapies.

3. The method of claim 2 wherein said one or more antiestrogens are selected from the group consisting of tamoxifen, toremifene and fulvestrant and said one or more aromatase inhibitors are selected from the group consisting of aromasin, letrozole and anastrozole.

4. The method according to claim 1 wherein said RAD1901 is administered in a total daily dosage of from between 100 mg and 1,000 mg.

5. The method according to claim 4 wherein said RAD1901 is administered in a total daily dosage of 100 mg, 200 mg, 300 mg, 400 mg, 500 mg, 600 mg, 700 mg, 800 mg, 900 mg or 1,000 mg.

6. The method according to claim 4, wherein said daily dosage is delivered in two separate doses.

7. The method according to claim 6 wherein said separate doses are equal doses.

8. The method according to claim 1 wherein said subject is a post-menopausal woman.

9. The method according to claim 1 wherein said m-TOR inhibitor is dosed from between 1 mg and 500 mg daily.

10. The method according to claim 9 wherein said m-TOR inhibitor is dosed at from between 5 mg and 100 mg daily.

11. The method according to claim 1, wherein said m-TOR inhibitor is everolimus.

12. The method according to claim 11 wherein said everolimus is dosed at a daily dose of 10 mg.

13. The method according to claim 11 wherein said everolimus is dosed at a daily dose from between 2.5 mg and 7.5 mg.

14. The method according to claim 1 wherein said m-TOR inhibitor is dosed once per day.

* * * * *